(12) United States Patent
Ma et al.

(10) Patent No.: US 9,796,967 B2
(45) Date of Patent: Oct. 24, 2017

(54) COMPOSITIONS RELATED TO CONTROLLABLE INTERVENING PROTEIN SEQUENCES (CIPS) COMPRISING REVERSIBLE ZINC-BINDING MOTIFS AND INTEINS

(71) Applicant: THE OHIO STATE UNIVERSITY, Columbus, OH (US)

(72) Inventors: Buyong Ma, Frederick, MD (US); David F. Nellis, Frederick, MD (US); Jianwei S. Zhu, Frederick, MD (US); David W. Wood, Dublin, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 166 days.

(21) Appl. No.: 14/418,858

(22) PCT Filed: Aug. 1, 2013

(86) PCT No.: PCT/US2013/053195
§ 371 (c)(1),
(2) Date: Jan. 30, 2015

(87) PCT Pub. No.: WO2014/022648
PCT Pub. Date: Feb. 6, 2014

(65) Prior Publication Data
US 2015/0197734 A1    Jul. 16, 2015

Related U.S. Application Data

(60) Provisional application No. 61/678,303, filed on Aug. 1, 2012, provisional application No. 61/777,068, filed on Mar. 12, 2013.

(51) Int. Cl.
*C12N 9/16* (2006.01)
*C07K 14/47* (2006.01)
*C07K 1/22* (2006.01)
*C07K 17/14* (2006.01)
*C07K 19/00* (2006.01)
*C12P 21/02* (2006.01)

(52) U.S. Cl.
CPC ............ *C12N 9/16* (2013.01); *C07K 1/22* (2013.01); *C07K 14/4702* (2013.01); *C12P 21/02* (2013.01); *C07K 2319/20* (2013.01); *C07K 2319/92* (2013.01)

(58) Field of Classification Search
CPC .. C07K 1/22; C07K 2319/92; C07K 14/4702; C07K 2319/20; C12N 9/16; C12P 21/02
See application file for complete search history.

(56) References Cited

U.S. PATENT DOCUMENTS

2006/0030007 A1   2/2006   Byrd et al.
2009/0098611 A1   4/2009   Wood et al.
2011/0172391 A1   7/2011   Liu et al.

FOREIGN PATENT DOCUMENTS

WO    01/12820 A1   2/2001

OTHER PUBLICATIONS

Mills et al., The Journal of Biological Chemistry 276(14):10832-10838, 2001.*
International Search Report of the International Searching Authority/US, issued in related application PCT/US2013/053195 on Mar. 11, 2014.

* cited by examiner

*Primary Examiner* — Delia Ramirez
(74) *Attorney, Agent, or Firm* — Meunier Carlin & Curfman LLC

(57) ABSTRACT

Disclosed are compositions comprising an engineered intein designed such that the self-cleaving activity of the intein can be modulated by a zinc-binding motif as well as methods and systems for making and using the compositions.

13 Claims, 35 Drawing Sheets

| Gene | N-Extein | Intein Sequence | C-Extein |
|---|---|---|---|
| Sce VMA | AILYVG | CFAKGT −(454AA)− NQVVVHN | CGERGN |
| Ctr VMA | VIIYVG | CFTKGT −(471AA)− NMALVHN | CGERGN |
| Mtu recA | KVVKNK | CLAEGT −(440AA)− EGVVVHN | CSPPFK |
| Mle recA | IGVMFG | CMNYST −(365AA)− DGVMVHN | SPETTT |
| Tli pol I2 | KVLYAD | SVSGES −(390AA)− NNILVHN | TDGFYA |
| Tli pol I1 | IKLLAN | SILPNE −(538AA)− GLLYAHN | SYYGYM |
| Psp pol | IKILAN | SILPEE −(537AA)− GFLYAHN | SYYGYY |

FIG. 3

| ZBM | Intein Sequence Peptide | Intein Sequence DNA | Zinc Binding Motif+ Intein Peptide | Zinc Binding Motif+ Intein DNA | Source |
|---|---|---|---|---|---|
| Original Al-CM intein | ALAEGTRIFDPVT GTTHRIEDVVGCR KPIHVAAAKDGT LHARPVSWFDQ GTRDVIGLRIABG AILWATPDHKVLT EYGWRAAGELRK GQRVAQPRRFDGF GDSAPIPARVQAL ADALDDKFLHDW LAEELRYSVIREVL PTRRARTFQLEVE ELHTLVAEGVVH N (SEQ ID NO: 7) | GGGCTGGCAGAGGGCAC TCGGATCTTCGATCCGG TCACCGGTACAACGCAT CCGATCGAGGATGTTGT CGGTGCCGCCAAGCCTA TTCATGTGTGGCTGCT GCCAAGACGGAAGGC TGCATGCGGGCGCGGTG GTGTCCTGGTTCGACCA GGGAACGCGGGATGTG ATCGGGTTGCGGATCGG CGGTGCGCCATGCTGT GGGCAACGCGGATCAC AAGGTGCTGACAGAGTA CGGTCGGCGTGCCGCG GGGAACTCCGCAAGG AGACAGGGTGCCGCAA CCGGCAGGTTCATGG ATTCGGTGACAGTGCC CGATTCGGCGCGGTC CACGGCTCGCGATCC CCTGATGACAATTCC GAAGACATGCTGGCG CGTCATCGAGAAGTGC TCCAACGCGGGGGCCA CGAACGTTCGGCCTCGA | | | Original Al-CM intein |

| ZBM | Intein Sequence Peptide | Intein Sequence DNA | Zinc Binding Motif+ Intein Peptide | Zinc Binding Motif+ Intein DNA | Source |
|---|---|---|---|---|---|
| GEGH (SEQ ID NO: 1) | HLAEGTRIFDPVT GTTHRIEDVVGGR KPIHVVAAKDGT LHARPVVSWFDQ GTRDVIGLRIAGG AILWATPDHKVLT EYGWRAAGELRK GDRVAQPRFDG GDSAPIPARVQAL ADALDDKFLHDM LAEELRYSVIREVL PTRRARTFGLEYE ELHTLVAEGVVVH N (SEQ ID NO:9) | CACCTGGCAGAGGCAC TGGATCTTCGATCCG TGACGGTACAACGAT CGCATCGAGGATGTT CGGTGGGCGAAGGTA TTCATGTCGTGGTGCT GCCAAGGACGGAACGG TGCATCGGGCGCCGTG CTGTCCTGGTTCGACCA GGGAACGCGGGATGTG ATGGGCTTGCGATCGC CGGTGGCCAATCTGT GGGCAACCGGATCAC AAGGTGTGACAGAGTA CGGCTGGCGTGCCGG GGAACTCCGAAGG AGACAGGGTCGCCAA CCCGAGGTTCGATGG ATTCGGGGCGGTG CGATCGCCGTCCGATGC CAGGCGGTCGCAGGCG CTGCGGATGACAATTCC TGCAGGACATGCTGGCG | GCGAAGGCGACATCA CCTGGCAGAGGCCA CTGGATCTTCGATC CGGTCACCGGTACAA CGGCATCGGATCGAGG ATGTTCGTGGTCGCA TGCAAGGCTATTCATG TGTGGCTGCTGCCA AGGACGGAACGCTG CATGGCGGCCGCCGTG CTGTCCTGGTTCGAC CAGGGAACGCGGGA TGTCATCGGGTTGCG GATCGGCGGTGGCC ATCTGTGGGCGAC ACCCGACAAGGT GCTGACAGAGTAC GCTGGCGTGCCGGGAC GGCAACTCCGAAG GGAACAGGGTGGC GCATGGCGGACAGGCTT CGATGGATTCGGTGA CACTGGTGGCGGATTCC | LN-001 |

| ZBM | Intein Sequence Peptide | Intein Sequence DNA | Zinc Binding Motif+ Intein Peptide | Zinc Binding Motif+ Intein DNA | Source |
|---|---|---|---|---|---|
| GEGH (SEQ ID NO: 1) | GLAEGTRIFDPVTG TTHRIEDVVGGRK PTHVVAAAKDGTL HARPVVSWFDQG TRDVIGLRTAGCAI LWATPDHKVLTE YQWRAAGELRKC DRVAQPRRFDGFG DSAPTPARVQALA DALDKFLHDWL AEELRYSVIREVLP TRRARTFGLEVEE LHTLVAEGVVH N (SEQ ID NO: 13) | GAAGAACTCGCTATTC CGTATCCGAGAGTGC TGCCAAGCGGCGACA CGAAGTTCGGCTCGA CGTCAGGAACTCACA CCCTCGTCGCGAAGGG GTTGTGTACACAAC (SEQ ID NO:10) | | GGCGGGCGTCAG CGTCGGGATCGCC TGGATGACAAATCC TGCAGACATGCTGG CGGAAGAACTCGCT ATTCCGTATCCGAG AAGTGCTGCCAACC GGCGGCACGAAGG TTCGGCTCGAGTC GAGAACTGCACA CCTCGTCGCGAAGG GTTGTGTACACAA C (SEQ ID NO: 12) | |
| | | TGCCTCGCAGAGGCAC TCGGATCTTCGATCCG TCACCCGGTACAACCAT CCCATCCAGGATGTGT CGGTGGCCAAGCCTA TTCATGTCTGTGCTGCT GCCAAGCACGGGAACCC TGCATGCGCGGCCCGTG GTTCGTCGTGGTTCGACCA GGAACGCGGGATGTG ATCGGGTTGCGGATCGG CGGTGCGCCATCCTGT GGGGCGACACCCATCAC AAGGTGCTGACAGAGTA | GEGHCLAEGTRIFDPV TGTTHRIEDVVGGRK PTHVVAAKDGTLHA RPVVSWFDQGTRDVI GLRTAGCAILWATPD HKVLTEYQWRAAGE LRKCDRVAQPRRFDG FGDSAPTPARVQALAD ALDDKFLHDWLAEEL RYSVIREVLPTRRART FGLEVEELHTLVAEG VVHN (SEQ ID NO: 15) | GGAGAGGGACAATTG CCTCCAGAGGGCA CTCGGATCTTCGATC CGGTCACCCGGTACAA CCGATCGAGGAGGG ATGTTGCGGTGGCC AAGCCTATTCATG TCGTGGCTGCCAA AGGACGGAACCCTG CATGCGCGGCCGTG GTGTCGTGGTTCGAC CAGGAACGCGGGA TGTGATCGGGTTGCG GATCGGCGGTGCGG C | LN-002 |

FIG. 17 continued

| ZBM | Intein Sequence Peptide | Intein Sequence DNA | Zinc Binding Motif + Intein Peptide | Zinc Binding Motif + Intein DNA | Source |
|---|---|---|---|---|---|
| | | | | | |
| GEGHH (SEQ ID NO: 3) | ALAEGTRIFDPVT GTTHRIEDVVGGR KPIHVVAAKDGT LHARPVVSWFDQ | CGCCTCGCCGAGGGCAC TCGGATCTTCGATCCCG TCACCGGTACACGGCAT CGCATCGAGGATGTTGT CGGAGGACGGACATCA TCCGATCGAGGAGT CACTCGGATCTTCGA TCCGGTCACGGGTAC (SEQ ID NO: 14) | GEGHHALAEGTRIFDP VTGTTHRIEDVVGGR KPIHVVAAKDGTLH ARPVVSWFDQGTRDV | GGAGGGCGACATCA TGCCTCGCAGGGC CACTCGGATCTTCGA TCCGGTCACGGGTAC | LN-003 |

FIG. 17 continued

| ZBM | Intein Sequence Peptide | Intein Sequence DNA | Zinc Binding Motif+ Intein Peptide | Zinc Binding Motif+ Intein DNA | Source |
|---|---|---|---|---|---|
| | CTRDVTGLRIAGG AILWATPDHKVLT EYGWRAAGELRK GDRVAQPRRFDGF GDSAPIPARVQAL ADALDDKFLHDM LAEELRYSVIREVL PTRRARTFGLFYE ELHTLVAEGVVHN (SEQ ID NO: 17) | CGGTGGGCCAAGCCTA TTCATGTGGTGCT GCCAAGCGAACGC TGCATCGCGGCCGTG GTGTCCTGGTCGACCA GCGAACCGGCGATGTG ATCCGGGTTCGGCATCGC CGGTGGCGCATCCTGT GGGCGACACCGATCAC AAGTGCTGACAGAGTA CGGCTGGGTTGCCGCCC GGGAACTCCCAAGG AGACAGGGTGGCAA CCGGCAGCGTTCGATGC ATTCGGTCAGTGCCC CCATTCCGGGCGGTG CACGCGTCGCGGATCC CCTGGATGACAAATCC TCCACGACATGCTGCC GAAGAACTCCGCTATTC CCTGATCCGAGAGTGC TGCAAGGGGGGCCGA CGAACGTTCGGCCTCA GGTCGAGGAACTGCACA CCCTCCTGCGGAAGGG GTTGTTGTACACAAC (SEQ ID NO: 18) | TGLRTAGGAILWATPD HKVLTEYGWRAAGE LRKGDRVAQPRRFDG FGDSAPIPARVQALAD ALDDKFLHDMLAEEL RYSVIREVLPTRRART FGLEFEELHTLVAEG VVHN (SEQ ID NO: 19) | AACGCATCCGCATCGA GGATGTTGTGGTGG GCCAAGCCTATTCA TGTGGTGGTGCTGC CAAGCACGAACGC TGCATGCGGGCCGG TGGTCGCGGTTCG ACCAGGAACGGG GATGTCGATCGGATTG CGGATCGCCGGTGGC GCCATCGTGTCGGCC ACACCGGATCACAA CGTGCTGACAGAGT ACGGCTGGGTCGCC CCGGGAACTCCGC AAGGACACAGGGT GCGCAACCGGCAAC GCTTCGATGGATTCG GTAACAGTGCCGCC ATTCCGGCCCCGGTG CACGCCTCGGCGAT GCCCTGGATGACAA ATTCCTGCACGAAT GCTGGCCGAAGAAC TCCGTATTCCGTCA TCCAGAAGTGCTGCA CAAGGGGGGCA | |

FIG. 17 continued

| ZBM | Intein Sequence Peptide | Intein Sequence DNA | Zinc Binding Motif + Intein Peptide | Zinc Binding Motif + Intein DNA | Source |
|---|---|---|---|---|---|
| CDGHH (SEQ ID NO: 5) | ALAEGTRIFDPVT GTTHRIEDVVGGR KPIHVVAAKDGT LHARPVVSWFDQ GTRDVIGLRIAGG AILWATPDHKVLT EYOWRAAGELRK GDRVAQPRRFDGF GDSAPTPARVQAL ADALDDKFLHDM LAEELRYSVIREVL PTRRARTFCLEVE ELHTLVAEGVVHN (SEQ ID NO: 21) | GCGCTCGCAGAGGCAC TCGATCTTCGATCCG TCACGGTACGACGGT CGGATCGAGGATGTGT CGGTGGCGCAAGCTA TCATGTGGCTGCT GCCAAGGACGGAACGC TGCATGGCCCGGCCTG CGTGCTCGGTTGCACCA GGGAACGGGATGTC ATCGGTTGCGCATGGC CGGTGGCGCCATCCTGT GGGCACACCCGGATCAC AAGGTGCTGACGAGTA CCGGCTGGCGTTCATGG GGGACTCGCAAGGG ACAAGGTGCGCGCAA CCGGCAGCTTCGATCGG ATTCGGTGACAGTGCGC CGATTCCGGGGGCGTG CAGGCGCTCGGCGATGC | CDGHHALAEGTRIFD PVTGTTHRIEDVVGG RKPIHVVAAKDGTL HARPVVSWFDQGTRD VIGLRIAGAILWATP DHKVLTEYOWRAAG ELRKGDRVAQPRRFD GFGDSAPTPARVQALA DALDDKFLHDMLAEE LRYSVIREVLPTRRAR TFGLEVEELHTLVAE GVVHN (SEQ ID NO: 23) | CGACGTTCGGCCTC GAGTCGAGGAACT GCACACCCTCGTCGC CGAAGGGTTGTTGT ACACAAC (SEQ ID NO: 20) GCAGATGCAGATCA TGCCTCCGAGGGG CACTCGGATCTTCGA TCCGGTCACGGTAC AACGGATCGAGGATGTGG GATGTTGTCGGTGG GCCAAGCCTATTCA TCTCGTGGCTGCTGC CAAGGACGGAACGC TGCATGCCCGGCCG TGGTCGTCGGTTCGG ACCAGGGAACGCGG GATGTGATCGGTTG CGGATCCGCGGTGGC GCCATCCTGTGGGCG ACACCCGATCACA GGTGCTGACAAGT ACGGCTGGCGTGCG CCGGGAACTGCGG AAGGAGACAAGGT GGCCAACCGCGAC | LN-003B |

FIG. 17 continued

| ZBM | Intein Sequence Peptide | Intein Sequence DNA | Zinc Binding Motif + Intein Peptide | Zinc Binding Motif + Intein DNA | Source |
|---|---|---|---|---|---|
| | CLAEGTRIFDPVTG TTHRIEDVYGGRK PIHVAAAKDGTL HARPVVSWFDGC TRDVIGLRIAGGAI LWATPDHKVLTE YGWRAAGELRKG DRVAQPRRFDGFG DSAPTPARVQALA DALDDKFLHDWL | CCTGGATGACAAATTCC TGCACGATGCTGGCG GAAGAACTCCGCTATTC CGTGATCCGAGAAGTGC TCCAAGCCGCGGGCA CGAACGTTCGGCTCGA GGTCGAAGAACTGCACA CCCTCGTCGCCAAGGC GTTGTGTACACAAC (SEQ ID NO: 22) | | | |
| CEGHG (SEQ ID NO: 4) | | TGCCTCGAGAGGGCAC TCGGATCTTCGATCCGG TCACCGGTACAACGAT CGGATCAGGATGTTGT CGGTGGGCAAGCCTA TTCATGTGGTGGCTGCT GCCAAGGACGGAACGC TGCATGCCGGCCCGTG GTGTCGTGGTTCGACCA GGGAACGGGATGTG | CECHGCLAEGTRIFDP VTGTTHRIEDVYGGR KPIHVAAKDGTLH ARPVVSWFDGCTRDV IGLRIAGGAILWATPD HKVLTEYGWRAAGE LRKGDRVAQPRRFDG FGDSAPTPARVQALAD ALDDKFLHDWLAEEL RYSVIREVLPTRRART | CGAGAGGCACATGC ATCCTCGAGAGG GCACTCGGATCTTCC ATCCGGTCACCGGTA CAACGGATCGCATCG AGGATGTTGGGTG CGGCAAGCCTATTC ATGTCCTGGCTGCTG CCAAGGACGGAACC GTGCATGCCGGCCC | LN-0004 |

FIG. 17 continued

| ZBM | Intein Sequence Peptide | Intein Sequence DNA | Zinc Binding Motif+ Intein Peptide | Zinc Binding Motif+ Intein DNA | Source |
|---|---|---|---|---|---|
| | AEELRYSVIREVLP TRRARTFGLEVEE LHTLVAEGVVHN (SEQ ID NO: 25) | ATGGGTTCGGATGGC CGTGGGCCATCCTGT CGGCCACACCGATCAC AAGGTGCTGACAGTA CGCTGGGTGCCCCCG GGGAACTCGGAAGGG AGACAGGCTGCGCAA CCGGACGTTCGATGG ATTCGGTGACATGCGG CGATTCGGGCGGGGTG CAGGCGCTCGGATGC CCTGGATGACAAATTCC TCCACCACATGTCGCC GAAGAACTCGGCCGG CGTGATCGAGAAGTC TGCAAGGGGGGGGCA CGAACGTTCGGCTCGA GGTCGAGGAACTGCACA CCCTCGTCGCCGAAGCG GTTGTTGTACACAAC (SEQ ID NO: 26) | FGLEVEELHTLVAEG VVHN (SEQ ID NO: 27) | GTGGTGTCTGGTTC GACCAGGGAAGCGG GGATGTGATCGGGTT CGGGCATCCCGGGTG CGGCCATCCTGTGGG CGAACCGGATCACA AGGTGCTGACAGAC TACGGCTTGGCGTGCC CCCCGGAACTCCG CAAGGAGACAGGG TGGCAACCGCGA CGCTTCGATGGATTC GGTGACATGCGCC GATTCGGGCGGGCGT GCAGGCGCTCGCGG ATGCCCTGGATGACA AATTCCTCGACGACA TGCTGCCGAAGAA CTCGGCCTATTCCGTG ATCGGAGAAGTGCTG CCAAGCGGCGGGCC ACGAACGTTCGGAGGAAC TGCACACCCTCGTCG CCCAAGGGGTTGTTC TACACAAC (SEQ ID NO: 28) | |

FIG. 17 continued

| ZBM | Intein Sequence Peptide | Intein Sequence DNA | Zinc Binding Motif + Intein Peptide | Zinc Binding Motif + Intein DNA | Source |
|---|---|---|---|---|---|
| GDGHG (SEQ ID NO: 6) | CLAEGTRIFDPVTG THRIEDVGGRK PIHVAAKDGTL HARPVVSWFDGG TRDVIGLRIAGGAI LWATPDHKVLTE YGWRAAGELRKG DRVAQPRRFDGFG DSAPIPARVQALA DALDDKFLHDML AEELRYSVREVLP TRRARTFGLEVEE LHTLVAEGVVYH N (SEQ ID NO: 29) | TGCCTCGAGGGCAC TCGATCTTCGATCCG TCACCGGTACACGCAT CCGATCGAGGATGTTGT CGGTGGGCCAAGCCTA TTCAGTCGTCGCTGCT CCCAAGGACGAACGC TGCATGCCCGCCCGTG GTCTCCTGGTTCGACCA GGGAACGGGGATGTG ATCGGTCTGCGGATCGC CGGTGGCGCCATCCTGT GGGCACACCGACAGTA AAGGTCCTGACAGAGTA CGGGTGGCGTGCCGCG AGACAGGGTGGGCGCAA CCCGCACGGTTCGATGG CATTCCGGCGCGGGTG CAGGCGCTCGCGGATGC CCTGGATGACAAATTCC TGCACGACATGCTGGCG GAAGAACTCCGCTATTC CGTGATCGAAGTGC TGCCAACGCGGCGGGCA CGAAGTTCGGCTCGA | GDGHGCLAEGTRIFD PVTGTTHRIEDVGG RKPIHVAAKDGTL HARPVVSWFDGTRD VIGLRIAGGAILWATP DHKVLTEYGWRAAG ELRKGDRVAQPRRFD GFGDSAPIPARVQALA DALDDKFLHDMLAEE LRYSVIREVLPTRRAR TFGLEVEELHTLVAE GVVYHN (SEQ ID NO: 31) | GGAGATGGACATGG ATGGCTGCAAGG GGACTGGGATGTTCC ATCCGGTCACCGGTA CAACGCATCCGATCG AGGATGTGTTGGTG GGCCAAGCCTATTC AGTCGTCGCTGCTC CCCAAGGACGAACGC CTGCATGCCCGCCGC GTGTCCTGGTTC GACCAGGGAACGG GGATGTGATCGGTT GCGGATCGCCGGTG GCGCATCCTGTGGG CGCACCGACATACA AGGTCCTGACAGAG TACGGGTGGCGTGCC GCGGGAACTCCG CAAGGAGACAGGG TGGCCACCGCGA CGGTTCGATGGATTC GGTGACAGTGCCG CATTCCGGCGCGGGT GCAGGCGCTCGCGG ATGCCCTGATGACA AATTCCTGCACGACA | LN-0048 |

FIG. 17 continued

| ZBM | Intein Sequence Peptide | Intein Sequence DNA | Zinc Binding Motif+ Intein Peptide | Zinc Binding Motif+ Intein DNA | Source |
|---|---|---|---|---|---|
| | | GGTGGAGAAGTGCACA GCCTGCGTGCGGAAGGG GTTGTTGTACACAAC (SEQ ID NO: 30) | | TGCTGGCGAAGAA CTCCCCTATTCCGTG ATCCGAGAAGTGCTG CCAACGCGGCGGGC ACGAACGTTCGGCCT CGAGTCGAGCAAC TGCACCCTCGTCG CCGAAGGGTTGTTG TACACAAC (SEQ ID NO: 32) | |

FIG. 17 continued

United States Patent US 9,796,967 B2

```
                              SEQUENCE LISTING

<160> NUMBER OF SEQ ID NOS: 44

<210> SEQ ID NO 1
<211> LENGTH: 4
<212> TYPE: PRT
<213> ORGANISM: Artificial Sequence
<220> FEATURE:
<223> OTHER INFORMATION: synthetic construct; reversible zinc binding
      motif

<400> SEQUENCE: 1

Gly Glu Gly His
1

<210> SEQ ID NO 2
<211> LENGTH: 4
<212> TYPE: PRT
<213> ORGANISM: Artificial Sequence
<220> FEATURE:
<223> OTHER INFORMATION: synthetic construct; reversible zinc binding
      motif

<400> SEQUENCE: 2

Gly Asp Gly His
1

<210> SEQ ID NO 3
<211> LENGTH: 5
<212> TYPE: PRT
<213> ORGANISM: Artificial Sequence
<220> FEATURE:
<223> OTHER INFORMATION: synthetic construct; reversible zinc binding
      motif

<400> SEQUENCE: 3

Gly Glu Gly His His
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic construct; reversible zinc binding
      motif

<400> SEQUENCE: 4

Gly Glu Gly His Gly
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic construct; reversible zinc binding
      motif

<400> SEQUENCE: 5
```

```
Gly Asp Gly His His
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic construct; reversible zinc binding
      motif

<400> SEQUENCE: 6

Gly Asp Gly His Gly
1               5

<210> SEQ ID NO 7
<211> LENGTH: 168
<212> TYPE: PRT
<213> ORGANISM: Artificial Sequence
<220> FEATURE:
<223> OTHER INFORMATION: synthetic construct; intein peptide sequence

<400> SEQUENCE: 7

Ala Leu Ala Glu Gly Thr Arg Ile Phe Asp Pro Val Thr Gly Thr Thr
1               5                   10                  15

His Arg Ile Glu Asp Val Val Gly Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Leu Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Arg Val
            100                 105                 110

Gln Ala Leu Ala Asp Ala Leu Asp Asp Lys Phe Leu His Asp Met Leu
        115                 120                 125

Ala Glu Glu Leu Arg Tyr Ser Val Ile Arg Glu Val Leu Pro Thr Arg
    130                 135                 140

Arg Ala Arg Thr Phe Gly Leu Glu Val Glu Glu Leu His Thr Leu Val
145                 150                 155                 160

Ala Glu Gly Val Val Val His Asn
                165

<210> SEQ ID NO 8
<211> LENGTH: 504
<212> TYPE: DNA
<213> ORGANISM: Artificial Sequence
<220> FEATURE:
<223> OTHER INFORMATION: synthetic construct; intein sequence

<400> SEQUENCE: 8
gccctcgcag agggcactcg gatcttcgat ccggtcaccg gtacaacgca tcgcatcgag      60
gatgttgtcg gtgggcgcaa gcctattcat gtcgtggctg ctgccaagga cggaacgctg     120
catgcgcggc ccgtggtgtc ctggttcgac cagggaacgc gggatgtgat cgggttgcgg     180
atcgccggtg gcgccatcct gtgggcgaca cccgatcaca aggtgctgac agagtacggc     240
tggcgtgccg ccggggaact ccgcaaggga gacagggtgg cgcaaccgcg acgcttcgat     300
```

```
ggattcggtg acagtgcgcc gattccggcg cgcgtgcagg cgctcgcgga tgccctggat    360
gacaaattcc tgcacgacat gctggcgaaa gaactccgct attccgtgat ccgagaagtg    420
ctgccaacgc ggcgggcacg aacgttcggc ctcgaggtcg aggaactgca caccctcgtc    480
gccgaagggg ttgttgtaca caac                                            504
```

<210> SEQ ID NO 9
<211> LENGTH: 168
<212> TYPE: PRT
<213> ORGANISM: Artificial Sequence
<220> FEATURE:
<223> OTHER INFORMATION: synthetic construct; intein peptide sequence

<400> SEQUENCE: 9

```
His Leu Ala Glu Gly Thr Arg Ile Phe Asp Pro Val Thr Gly Thr Thr
1               5                   10                  15

His Arg Ile Glu Asp Val Val Gly Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Leu Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Arg Val
            100                 105                 110

Gln Ala Leu Ala Asp Ala Leu Asp Asp Lys Phe Leu His Asp Met Leu
        115                 120                 125

Ala Glu Glu Leu Arg Tyr Ser Val Ile Arg Glu Val Leu Pro Thr Arg
    130                 135                 140

Arg Ala Arg Thr Phe Gly Leu Glu Val Glu Glu Leu His Thr Leu Val
145                 150                 155                 160

Ala Glu Gly Val Val Val His Asn
                165
```

<210> SEQ ID NO 10
<211> LENGTH: 504
<212> TYPE: DNA
<213> ORGANISM: Artificial Sequence
<220> FEATURE:
<223> OTHER INFORMATION: synthetic construct; intein sequence

<400> SEQUENCE: 10

```
cacctcgcag agggcactcg gatcttcgat ccggtcaccg gtacaacgca tcgcatcgag     60
gatgttgtcg gtgggcgcaa gcctattcat gtcgtggctg ctgccaagga cggaacgctg    120
catgcgcggc ccgtggtgtc ctggttcgac cagggaacgc gggatgtgat cgggttgcgg    180
atcgccggtg gcgccatcct gtgggcgaca cccgatcaca aggtgctgac agagtacggc    240
tggcgtgccg ccggggaact ccgcaaggga gacagggtgg cgcaaccgcg acgcttcgat    300
ggattcggtg acagtgcgcc gattccggcg cgcgtgcagg cgctcgcgga tgccctggat    360
gacaaattcc tgcacgacat gctggcgaaa gaactccgct attccgtgat ccgagaagtg    420
ctgccaacgc ggcgggcacg aacgttcggc ctcgaggtcg aggaactgca caccctcgtc    480
gccgaagggg ttgttgtaca caac                                            504
```

<210> SEQ ID NO 11
<211> LENGTH: 172
<212> TYPE: PRT
<213> ORGANISM: Artificial Sequence
<220> FEATURE:
<223> OTHER INFORMATION: synthetic construct; zinc binding motif plus intein peptide

<400> SEQUENCE: 11

```
Gly Glu Gly His His Leu Ala Glu Gly Thr Arg Ile Phe Asp Pro Val
1               5                   10                  15

Thr Gly Thr Thr His Arg Ile Glu Asp Val Val Gly Gly Arg Lys Pro
            20                  25                  30

Ile His Val Ala Ala Ala Lys Asp Gly Thr Leu His Ala Arg Pro
        35                  40                  45

Val Val Ser Trp Phe Asp Gln Gly Thr Arg Asp Val Ile Gly Leu Arg
    50                  55                  60

Ile Ala Gly Gly Ala Ile Leu Trp Ala Thr Pro Asp His Lys Val Leu
65                  70                  75                  80

Thr Glu Tyr Gly Trp Arg Ala Ala Gly Glu Leu Arg Lys Gly Asp Arg
                85                  90                  95

Val Ala Gln Pro Arg Arg Phe Asp Gly Phe Gly Asp Ser Ala Pro Ile
            100                 105                 110

Pro Ala Arg Val Gln Ala Leu Ala Asp Ala Leu Asp Lys Phe Leu
        115                 120                 125

His Asp Met Leu Ala Glu Glu Leu Arg Tyr Ser Val Ile Arg Glu Val
    130                 135                 140

Leu Pro Thr Arg Arg Ala Arg Thr Phe Gly Leu Glu Val Glu Glu Leu
145                 150                 155                 160

His Thr Leu Val Ala Glu Gly Val Val Val His Asn
                165                 170
```

<210> SEQ ID NO 12
<211> LENGTH: 516
<212> TYPE: DNA
<213> ORGANISM: Artificial Sequence
<220> FEATURE:
<223> OTHER INFORMATION: synthetic construct; zinc binding motif plus intein sequence

<400> SEQUENCE: 12

```
ggagagggac atcacctcgc agagggcact cggatcttcg atccggtcac cggtacaacg    60
catcgcatcg aggatgttgt cggtgggcgc aagcctattc atgtcgtggc tgctgccaag   120
gacggaacgc tgcatgcgcg gcccgtggtg tcctggttcg accagggaac gcgggatgtg   180
atcgggttgc ggatcgccgg tggcgccatc ctgtgggcga cacccgatca caaggtgctg   240
acagagtacg gctggcgtgc cgccggggaa ctccgcaagg gagacagggt ggcgcaaccg   300
cgacgcttcg atggattcgg tgacagtgcg ccgattccgg cgcgcgtgca ggcgctcgcg   360
gatgccctgg atgacaaatt cctgcacgac atgctggcgg aagaactccg ctattccgtg   420
atccgagaag tgctgccaac gcggcgggca cgaacgttcg gcctcgaggt cgaggaactg   480
cacacccctcg tcgccgaagg ggttgttgta cacaac                            516
```

<210> SEQ ID NO 13
<211> LENGTH: 168
<212> TYPE: PRT
<213> ORGANISM: Artificial Sequence
<220> FEATURE:
<223> OTHER INFORMATION: synthetic construct; intein peptide sequence

<400> SEQUENCE: 13

```
Cys Leu Ala Glu Gly Thr Arg Ile Phe Asp Pro Val Thr Gly Thr Thr
 1               5                  10                  15

His Arg Ile Glu Asp Val Val Gly Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Leu Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Arg Val
            100                 105                 110

Gln Ala Leu Ala Asp Ala Leu Asp Asp Lys Phe Leu His Asp Met Leu
        115                 120                 125

Ala Glu Glu Leu Arg Tyr Ser Val Ile Arg Glu Val Leu Pro Thr Arg
    130                 135                 140

Arg Ala Arg Thr Phe Gly Leu Glu Val Glu Leu His Thr Leu Val
145                 150                 155                 160

Ala Glu Gly Val Val Val His Asn
                165
```

<210> SEQ ID NO 14
<211> LENGTH: 504
<212> TYPE: DNA
<213> ORGANISM: Artificial Sequence
<220> FEATURE:
<223> OTHER INFORMATION: synthetic construct; intein sequence

<400> SEQUENCE: 14

```
tgcctcgcag agggcactcg gatcttcgat ccggtcaccg gtacaacgca tcgcatcgag      60
gatgttgtcg gtgggcgcaa gcctattcat gtcgtggctg ctgccaagga cggaacgctg     120
catgcgcggc ccgtggtgtc ctggttcgac cagggaacgc gggatgtgat cgggttgcgg     180
atcgccggtg gcgccatcct gtgggcgaca cccgatcaca aggtgctgac agagtacggc     240
tggcgtgccg ccggggaact ccgcaaggga gacagggtgg cgcaaccgcg acgcttcgat     300
ggattcggtg acagtgcgcc gattccggcg cgcgtgcagg cgctcgcgga tgccctggat     360
gacaaattcc tgcacgacat gctggcggaa gaactccgct attccgtgat ccagaagtg      420
ctgccaacgc ggcgggcacg aacgttcggc ctcgaggtcg aggaactgca caccctcgtc     480
gccgaagggg ttgttgtaca caac                                           504
```

<210> SEQ ID NO 15
<211> LENGTH: 172
<212> TYPE: PRT
<213> ORGANISM: Artificial Sequence
<220> FEATURE:
<223> OTHER INFORMATION: synthetic construct; intein peptide plus zinc
      binding motif

<400> SEQUENCE: 15

```
Gly Glu Gly His Cys Leu Ala Glu Gly Thr Arg Ile Phe Asp Pro Val
 1               5                  10                  15
```

```
Thr Gly Thr Thr His Arg Ile Glu Asp Val Val Gly Gly Arg Lys Pro
            20                  25                  30

Ile His Val Val Ala Ala Ala Lys Asp Gly Thr Leu His Ala Arg Pro
         35                  40                  45

Val Val Ser Trp Phe Asp Gln Gly Thr Arg Asp Val Ile Gly Leu Arg
 50                  55                  60

Ile Ala Gly Gly Ala Ile Leu Trp Ala Thr Pro Asp His Lys Val Leu
 65                  70                  75                  80

Thr Glu Tyr Gly Trp Arg Ala Ala Gly Glu Leu Arg Lys Gly Asp Arg
                 85                  90                  95

Val Ala Gln Pro Arg Arg Phe Asp Gly Phe Gly Asp Ser Ala Pro Ile
                100                 105                 110

Pro Ala Arg Val Gln Ala Leu Ala Asp Ala Leu Asp Asp Lys Phe Leu
            115                 120                 125

His Asp Met Leu Ala Glu Glu Leu Arg Tyr Ser Val Ile Arg Glu Val
130                 135                 140

Leu Pro Thr Arg Arg Ala Arg Thr Phe Gly Leu Glu Val Glu Glu Leu
145                 150                 155                 160

His Thr Leu Val Ala Glu Gly Val Val Val His Asn
                165                 170

<210> SEQ ID NO 16
<211> LENGTH: 516
<212> TYPE: DNA
<213> ORGANISM: Artificial Sequence
<220> FEATURE:
<223> OTHER INFORMATION: synthetic construct; intein plus zinc binding
      motif sequence

<400> SEQUENCE: 16
ggagagggac attgcctcgc agagggcact cggatcttcg atccggtcac cggtacaacg        60
catcgcatcg aggatgttgt cggtgggcgc aagcctattc atgtcgtggc tgctgccaag       120
gacggaacgc tgcatgcgcg gcccgtggtg tcctggttcg accagggaac gcgggatgtg       180
atcgggttgc ggatcgccgg tggcgccatc ctgtgggcga cccgatca caaggtgctg         240 acagagtacg gctggcgtgc cgccggggaa ctccgcaagg gagacagggt ggcgcaaccg       300
cgacgcttcg atggattcgg tgacagtgcg ccgattccgg cgcgcgtgca ggcgctcgcg       360
gatgccctgg atgacaaatt cctgcacgac atgctggcgg aagaactccg ctattccgtg       420
atccgagaag tgctgccaac gcggcgggca cgaacgttcg gcctcgaggt cgaggaactg       480 cacacccttcg tcgccgaagg ggttgttgta cacaac                                516

<210> SEQ ID NO 17
<211> LENGTH: 168
<212> TYPE: PRT
<213> ORGANISM: Artificial Sequence
<220> FEATURE:
<223> OTHER INFORMATION: synthetic construct; intein peptide sequence

<400> SEQUENCE: 17

Ala Leu Ala Glu Gly Thr Arg Ile Phe Asp Pro Val Thr Gly Thr Thr
 1               5                  10                  15

His Arg Ile Glu Asp Val Val Gly Gly Arg Lys Pro Ile His Val Val
            20                  25                  30

Ala Ala Ala Lys Asp Gly Thr Leu His Ala Arg Pro Val Val Ser Trp
         35                  40                  45
```

```
Phe Asp Gln Gly Thr Arg Asp Val Ile Gly Leu Arg Ile Ala Gly Gly
    50                  55                  60
Ala Ile Leu Trp Ala Thr Pro Asp His Lys Val Leu Thr Glu Tyr Gly
65                  70                  75                  80
Trp Arg Ala Ala Gly Glu Leu Arg Lys Gly Asp Arg Val Ala Gln Pro
                85                  90                  95
Arg Arg Phe Asp Gly Phe Gly Asp Ser Ala Pro Ile Pro Ala Arg Val
            100                 105                 110
Gln Ala Leu Ala Asp Ala Leu Asp Asp Lys Phe Leu His Asp Met Leu
        115                 120                 125
Ala Glu Glu Leu Arg Tyr Ser Val Ile Arg Glu Val Leu Pro Thr Arg
    130                 135                 140
Arg Ala Arg Thr Phe Gly Leu Glu Val Glu Glu Leu His Thr Leu Val
145                 150                 155                 160
Ala Glu Gly Val Val Val His Asn
                165

<210> SEQ ID NO 18
<211> LENGTH: 504
<212> TYPE: DNA
<213> ORGANISM: Artificial Sequence
<220> FEATURE:
<223> OTHER INFORMATION: synthetic construct; intein sequence

<400> SEQUENCE: 18
gccctcgcag agggcactcg atcttcgat ccggtcaccg gtacaacgca tcgcatcgag      60
gatgttgtcg gtgggcgcaa gcctattcat gtcgtggctg ctgccaagga cggaacgctg     120
catgcgcggc ccgtggtgtc ctggttcgac cagggaacgc gggatgtgat cgggttgcgg     180
atcgccggtg gcgccatcct gtgggcgaca cccgatcaca aggtgctgac agagtacggc     240
tggcgtgccg ccggggaact ccgcaaggga gacagggtgg cgcaaccgcg acgcttcgat     300
ggattcggtg acagtgcgcc gattccggcg cgcgtgcagg cgctcgcgga tgccctggat     360
gacaaattcc tgcacgacat gctggcggaa gaactccgct attccgtgat ccgagaagtg     420
ctgccaacgc ggcgggcacg aacgttcggc ctcgaggtcg aggaactgca cccctcgtc     480
gccgaagggg ttgttgtaca caac                                           504

<210> SEQ ID NO 19
<211> LENGTH: 173
<212> TYPE: PRT
<213> ORGANISM: Artificial Sequence
<220> FEATURE:
<223> OTHER INFORMATION: synthetic construct; intein peptide plus zinc
      binding motif

<400> SEQUENCE: 19

Gly Glu Gly His His Ala Leu Ala Glu Gly Thr Arg Ile Phe Asp Pro
1               5                   10                  15
Val Thr Gly Thr Thr His Arg Ile Glu Asp Val Val Gly Gly Arg Lys
            20                  25                  30
Pro Ile His Val Val Ala Ala Lys Asp Gly Thr Leu His Ala Arg
        35                  40                  45
Pro Val Val Ser Trp Phe Asp Gln Gly Thr Arg Asp Val Ile Gly Leu
    50                  55                  60
Arg Ile Ala Gly Gly Ala Ile Leu Trp Ala Thr Pro Asp His Lys Val
65                  70                  75                  80
Leu Thr Glu Tyr Gly Trp Arg Ala Ala Gly Glu Leu Arg Lys Gly Asp
```

```
                       85                  90                  95
Arg Val Ala Gln Pro Arg Arg Phe Asp Gly Phe Gly Asp Ser Ala Pro
                100                 105                 110

Ile Pro Ala Arg Val Gln Ala Leu Ala Asp Ala Leu Asp Asp Lys Phe
            115                 120                 125

Leu His Asp Met Leu Ala Glu Glu Leu Arg Tyr Ser Val Ile Arg Glu
    130                 135                 140

Val Leu Pro Thr Arg Arg Ala Arg Thr Phe Gly Leu Glu Val Glu Glu
145                 150                 155                 160

Leu His Thr Leu Val Ala Glu Gly Val Val Val His Asn
                165                 170
```

<210> SEQ ID NO 20
<211> LENGTH: 519
<212> TYPE: DNA
<213> ORGANISM: Artificial Sequence
<220> FEATURE:
<223> OTHER INFORMATION: synthetic construct; intein plus zinc binding
      motif sequence

<400> SEQUENCE: 20

```
ggagagggac atcatgccct cgcagagggc actcggatct tcgatccggt caccggtaca      60
acgcatcgca tcgaggatgt tgtcggtggg cgcaagccta ttcatgtcgt ggctgctgcc     120
aaggacggaa cgctgcatgc gcggcccgtg gtgtcctggt tcgaccaggg aacgcgggat     180
gtgatcgggt tgcggatcgc cggtggcgcc atcctgtggg cgacacccga tcacaaggtg     240
ctgacagagt acggctggcg tgccgccggg gaactccgca agggagacag ggtggcgcaa     300
ccgcgacgct tcgatggatt cggtgacagt gcgccgattc cggcgcgcgt gcaggcgctc     360
gcggatgccc tggatgacaa attcctgcac gacatgctgg cggaagaact ccgctattcc     420
gtgatccgag aagtgctgcc aacgcggcgg gcacgaacgt tcggcctcga ggtcgaggaa     480
ctgcacaccc tcgtcgccga agggttgtt gtacacaac                             519
```

<210> SEQ ID NO 21
<211> LENGTH: 168
<212> TYPE: PRT
<213> ORGANISM: Artificial Sequence
<220> FEATURE:
<223> OTHER INFORMATION: synthetic construct; intein peptide

<400> SEQUENCE: 21

```
Ala Leu Ala Glu Gly Thr Arg Ile Phe Asp Pro Val Thr Gly Thr Thr
1               5                   10                  15

His Arg Ile Glu Asp Val Val Gly Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Leu Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Arg Val
            100                 105                 110

Gln Ala Leu Ala Asp Ala Leu Asp Asp Lys Phe Leu His Asp Met Leu
        115                 120                 125
```

Ala Glu Glu Leu Arg Tyr Ser Val Ile Arg Glu Val Leu Pro Thr Arg
            130                 135                 140

Arg Ala Arg Thr Phe Gly Leu Glu Val Glu Glu Leu His Thr Leu Val
145                 150                 155                 160

Ala Glu Gly Val Val Val His Asn
                165

<210> SEQ ID NO 22
<211> LENGTH: 504
<212> TYPE: DNA
<213> ORGANISM: Artificial Sequence
<220> FEATURE:
<223> OTHER INFORMATION: synthetic construct; intein sequence

<400> SEQUENCE: 22
gccctcgcag agggcactcg gatcttcgat ccggtcaccg gtacaacgca tcgcatcgag      60
gatgttgtcg gtgggcgcaa gcctattcat gtcgtggctg ctgccaagga cggaacgctg     120
catgcgcggc ccgtggtgtc ctggttcgac cagggaacgc gggatgtgat cgggttgcgg     180
atcgccggtg gcgccatcct gtgggcgaca cccgatcaca aggtgctgac agagtacggc     240
tggcgtgccg ccggggaact ccgcaaggga gacagggtgg cgcaaccgcg acgcttcgat     300
ggattcggtg acagtgcgcc gattccggcg cgcgtgcagg cgctcgcgga tgccctggat     360
gacaaattcc tgcacgacat gctggcggaa gaactccgct attccgtgat ccgagaagtg     420
ctgccaacgc ggcgggcacg aacgttcggc ctcgaggtcg aggaactgca caccctcgtc     480
gccgaagggg ttgttgtaca caac                                             504

<210> SEQ ID NO 23
<211> LENGTH: 173
<212> TYPE: PRT
<213> ORGANISM: Artificial Sequence
<220> FEATURE:
<223> OTHER INFORMATION: synthetic construct; intein peptide plus zinc
      binding motif

<400> SEQUENCE: 23

Gly Asp Gly His His Ala Leu Ala Glu Gly Thr Arg Ile Phe Asp Pro
1               5                   10                  15

Val Thr Gly Thr Thr His Arg Ile Glu Asp Val Val Gly Gly Arg Lys
            20                  25                  30

Pro Ile His Val Val Ala Ala Lys Asp Gly Thr Leu His Ala Arg
        35                  40                  45

Pro Val Val Ser Trp Phe Asp Gln Gly Thr Arg Asp Val Ile Gly Leu
    50                  55                  60

Arg Ile Ala Gly Gly Ala Ile Leu Trp Ala Thr Pro Asp His Lys Val
65                  70                  75                  80

Leu Thr Glu Tyr Gly Trp Arg Ala Ala Gly Glu Leu Arg Lys Gly Asp
                85                  90                  95

Arg Val Ala Gln Pro Arg Arg Phe Asp Gly Phe Gly Asp Ser Ala Pro
            100                 105                 110

Ile Pro Ala Arg Val Gln Ala Leu Ala Asp Ala Leu Asp Asp Lys Phe
        115                 120                 125

Leu His Asp Met Leu Ala Glu Glu Leu Arg Tyr Ser Val Ile Arg Glu
    130                 135                 140

Val Leu Pro Thr Arg Arg Ala Arg Thr Phe Gly Leu Glu Val Glu Glu
145                 150                 155                 160

Leu His Thr Leu Val Ala Glu Gly Val Val His Asn
            165                 170

<210> SEQ ID NO 24
<211> LENGTH: 519
<212> TYPE: DNA
<213> ORGANISM: Artificial Sequence
<220> FEATURE:
<223> OTHER INFORMATION: synthetic construct; intein plus zinc binding
      motif sequence

<400> SEQUENCE: 24

```
ggagatggac atcatgccct cgcagagggc actcggatct tcgatccggt caccggtaca     60
acgcatcgca tcgaggatgt tgtcggtggg cgcaagccta ttcatgtcgt ggctgctgcc    120
aaggacggaa cgctgcatgc gcggcccgtg gtgtcctggt tcgaccaggg aacgcgggat    180
gtgatcgggt tgcggatcgc cggtggcgcc atcctgtggg cgacacccga tcacaaggtg    240
ctgacagagt acggctggcg tgccgccggg gaactccgca agggagacag ggtggcgcaa    300
ccgcgacgct tcgatggatt cggtgacagt gcgccgattc cggcgcgcgt gcaggcgctc    360
gcggatgccc tggatgacaa attcctgcac gacatgctgg cggaagaact ccgctattcc    420
gtgatccgag aagtgctgcc aacgcggcgg gcacgaacgt tcggcctcga ggtcgaggaa    480
ctgcacaccc tcgtcgccga aggggttgtt gtacacaac                           519
```

<210> SEQ ID NO 25
<211> LENGTH: 168
<212> TYPE: PRT
<213> ORGANISM: Artificial Sequence
<220> FEATURE:
<223> OTHER INFORMATION: synthetic construct; intein peptide

<400> SEQUENCE: 25

Cys Leu Ala Glu Gly Thr Arg Ile Phe Asp Pro Val Thr Gly Thr Thr
1               5                   10                  15

His Arg Ile Glu Asp Val Val Gly Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Leu Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Arg Val
            100                 105                 110

Gln Ala Leu Ala Asp Ala Leu Asp Asp Lys Phe Leu His Asp Met Leu
        115                 120                 125

Ala Glu Glu Leu Arg Tyr Ser Val Ile Arg Glu Val Leu Pro Thr Arg
    130                 135                 140

Arg Ala Arg Thr Phe Gly Leu Glu Val Glu Glu Leu His Thr Leu Val
145                 150                 155                 160

Ala Glu Gly Val Val Val His Asn
            165

<210> SEQ ID NO 26
<211> LENGTH: 504
<212> TYPE: DNA

<213> ORGANISM: Artificial Sequence
<220> FEATURE:
<223> OTHER INFORMATION: synthetic construct; intein sequence

<400> SEQUENCE: 26

```
tgcctcgcag agggcactcg gatcttcgat ccggtcaccg gtacaacgca tcgcatcgag    60
gatgttgtcg gtgggcgcaa gcctattcat gtcgtggctg ctgccaagga cggaacgctg   120
catgcgcggc ccgtggtgtc ctggttcgac cagggaacgc gggatgtgat cgggttgcgg   180
atcgccggtg gcgccatcct gtgggcgaca cccgatcaca aggtgctgac agagtacggc   240
tggcgtgccg ccggggaact ccgcaaggga gacagggtgg cgcaaccgcg acgcttcgat   300
ggattcggtg acagtgcgcc gattccggcg cgcgtgcagg cgctcgcgga tgccctggat   360
gacaaattcc tgcacgacat gctggcgaaa gaactccgct attccgtgat ccgagaagtg   420
ctgccaacgc ggcgggcacg aacgttcggc ctcgaggtcg aggaactgca caccctcgtc   480
gccgaagggg ttgttgtaca caac                                         504
```

<210> SEQ ID NO 27
<211> LENGTH: 173
<212> TYPE: PRT
<213> ORGANISM: Artificial Sequence
<220> FEATURE:
<223> OTHER INFORMATION: synthetic construct; intein peptide plus zinc
      binding motif

<400> SEQUENCE: 27

```
Gly Glu Gly His Gly Cys Leu Ala Glu Gly Thr Arg Ile Phe Asp Pro
1               5                   10                  15

Val Thr Gly Thr Thr His Arg Ile Glu Asp Val Val Gly Gly Arg Lys
            20                  25                  30

Pro Ile His Val Val Ala Ala Lys Asp Gly Thr Leu His Ala Arg
        35                  40                  45

Pro Val Val Ser Trp Phe Asp Gln Gly Thr Arg Asp Val Ile Gly Leu
    50                  55                  60

Arg Ile Ala Gly Gly Ala Ile Leu Trp Ala Thr Pro Asp His Lys Val
65                  70                  75                  80

Leu Thr Glu Tyr Gly Trp Arg Ala Ala Gly Glu Leu Arg Lys Gly Asp
                85                  90                  95

Arg Val Ala Gln Pro Arg Arg Phe Asp Gly Phe Gly Asp Ser Ala Pro
            100                 105                 110

Ile Pro Ala Arg Val Gln Ala Leu Ala Asp Ala Leu Asp Asp Lys Phe
        115                 120                 125

Leu His Asp Met Leu Ala Glu Glu Leu Arg Tyr Ser Val Ile Arg Glu
    130                 135                 140

Val Leu Pro Thr Arg Arg Ala Arg Thr Phe Gly Leu Glu Val Glu Glu
145                 150                 155                 160

Leu His Thr Leu Val Ala Glu Gly Val Val Val His Asn
                165                 170
```

<210> SEQ ID NO 28
<211> LENGTH: 519
<212> TYPE: DNA
<213> ORGANISM: Artificial Sequence
<220> FEATURE:
<223> OTHER INFORMATION: synthetic construct; intein plus zinc binding
      motif sequence

<400> SEQUENCE: 28

```
ggagagggac atggatgcct cgcagagggc actcggatct tcgatccggt caccggtaca    60
acgcatcgca tcgaggatgt tgtcggtggg cgcaagccta ttcatgtcgt ggctgctgcc   120
aaggacggaa cgctgcatgc gcggcccgtg gtgtcctggt tcgaccaggg aacgcgggat   180
gtgatcgggt tgcggatcgc cggtggcgcc atcctgtggg cgacacccga tcacaaggtg   240
ctgacagagt acggctggcg tgccgccggg gaactccgca agggagacag ggtggcgcaa   300
ccgcgacgct tcgatggatt cggtgacagt gcgccgattc cggcgcgcgt gcaggcgctc   360
gcggatgccc tggatgacaa attcctgcac gacatgctgg cggaagaact ccgctattcc   420
gtgatccgag aagtgctgcc aacgcggcgg cacgaacgt tcggcctcga ggtcgaggaa    480
ctgcacaccc tcgtcgccga aggggttgtt gtacacaac                          519
```

<210> SEQ ID NO 29
<211> LENGTH: 168
<212> TYPE: PRT
<213> ORGANISM: Artificial Sequence
<220> FEATURE:
<223> OTHER INFORMATION: synthetic construct; intein peptide

<400> SEQUENCE: 29

```
Cys Leu Ala Glu Gly Thr Arg Ile Phe Asp Pro Val Thr Gly Thr Thr
1               5                   10                  15

His Arg Ile Glu Asp Val Val Gly Gly Arg Lys Pro Ile His Val Val
            20                  25                  30

Ala Ala Ala Lys Asp Gly Thr Leu His Ala Arg Pro Val Val Ser Trp
        35                  40                  45

Phe Asp Gln Gly Thr Arg Asp Val Ile Gly Leu Arg Ile Ala Gly Gly
    50                  55                  60

Ala Ile Leu Trp Ala Thr Pro Asp His Lys Val Leu Thr Glu Tyr Gly
65                  70                  75                  80

Trp Arg Ala Ala Gly Glu Leu Arg Lys Gly Asp Arg Val Ala Gln Pro
                85                  90                  95

Arg Arg Phe Asp Gly Phe Gly Asp Ser Ala Pro Ile Pro Ala Arg Val
            100                 105                 110

Gln Ala Leu Ala Asp Ala Leu Asp Asp Lys Phe Leu His Asp Met Leu
        115                 120                 125

Ala Glu Glu Leu Arg Tyr Ser Val Ile Arg Glu Val Leu Pro Thr Arg
    130                 135                 140

Arg Ala Arg Thr Phe Gly Leu Glu Val Glu Glu Leu His Thr Leu Val
145                 150                 155                 160

Ala Glu Gly Val Val Val His Asn
                165
```

<210> SEQ ID NO 30
<211> LENGTH: 504
<212> TYPE: DNA
<213> ORGANISM: Artificial Sequence
<220> FEATURE:
<223> OTHER INFORMATION: synthetic construct; intein sequence

<400> SEQUENCE: 30

```
tgcctcgcag agggcactcg gatcttcgat ccggtcaccg gtacaacgca tcgcatcgag    60
gatgttgtcg gtgggcgcaa gcctattcat gtcgtggctg ctgccaagga cggaacgctg   120
catgcgcggc ccgtggtgtc ctggttcgac cagggaacgc gggatgtgat cgggttgcgg   180
atcgccggtg gcgccatcct gtgggcgaca cccgatcaca aggtgctgac agagtacggc   240
```

```
tggcgtgccg ccggggaact ccgcaaggga gacagggtgg cgcaaccgcg acgcttcgat      300
ggattcggtg acagtgcgcc gattccggcg cgcgtgcagg cgctcgcgga tgccctggat      360
gacaaattcc tgcacgacat gctggcggaa gaactccgct attccgtgat ccgagaagtg      420
ctgccaacgc ggcgggcacg aacgttcggc ctcgaggtcg aggaactgca caccctcgtc      480
gccgaagggg ttgttgtaca caac                                             504
```

<210> SEQ ID NO 31
<211> LENGTH: 173
<212> TYPE: PRT
<213> ORGANISM: Artificial Sequence
<220> FEATURE:
<223> OTHER INFORMATION: synthetic construct; intein peptide plus zinc
      binding motif

<400> SEQUENCE: 31

```
Gly Asp Gly His Gly Cys Leu Ala Glu Gly Thr Arg Ile Phe Asp Pro
1               5                   10                  15

Val Thr Gly Thr Thr His Arg Ile Glu Asp Val Val Gly Gly Arg Lys
            20                  25                  30

Pro Ile His Val Val Ala Ala Ala Lys Asp Gly Thr Leu His Ala Arg
        35                  40                  45

Pro Val Val Ser Trp Phe Asp Gln Gly Thr Arg Asp Val Ile Gly Leu
    50                  55                  60

Arg Ile Ala Gly Gly Ala Ile Leu Trp Ala Thr Pro Asp His Lys Val
65                  70                  75                  80

Leu Thr Glu Tyr Gly Trp Arg Ala Ala Gly Glu Leu Arg Lys Gly Asp
                85                  90                  95

Arg Val Ala Gln Pro Arg Arg Phe Asp Gly Phe Gly Asp Ser Ala Pro
            100                 105                 110

Ile Pro Ala Arg Val Gln Ala Leu Ala Asp Ala Leu Asp Asp Lys Phe
        115                 120                 125

Leu His Asp Met Leu Ala Glu Glu Leu Arg Tyr Ser Val Ile Arg Glu
    130                 135                 140

Val Leu Pro Thr Arg Arg Ala Arg Thr Phe Gly Leu Glu Val Glu Glu
145                 150                 155                 160

Leu His Thr Leu Val Ala Glu Gly Val Val Val His Asn
                165                 170
```

<210> SEQ ID NO 32
<211> LENGTH: 519
<212> TYPE: DNA
<213> ORGANISM: Artificial Sequence
<220> FEATURE:
<223> OTHER INFORMATION: synthetic construct; intein plus zinc binding
      motif sequence

<400> SEQUENCE: 32

```
ggagatggac atggatgcct cgcagagggc actcggatct cgatccggt caccggtaca       60 acgcatcgca tcgaggatgt tgtcggtggg cgcaagccta ttcatgtcgt ggctgctgcc     120
aaggacggaa cgctgcatgc gcggcccgtg gtgtcctggt tcgaccaggg aacgcgggat     180
gtgatcgggt tgcggatcgc cggtggcgcc atcctgtggg cgacaccga tcacaaggtg     240 ctgacagagt acggctggcg tgccgccggg gaactccgca agggagacag ggtggcgcaa     300
ccgcgacgct tcgatggatt cggtgacagt gcgccgattc cggcgcgcgt gcaggcgctc     360
gcggatgccc tggatgacaa attcctgcac gacatgctgg cggaagaact ccgctattcc     420
```

```
gtgatccgag aagtgctgcc aacgcggcgg gcacgaacgt tcggcctcga ggtcgaggaa    480
ctgcacaccc tcgtcgccga aggggttgtt gtacacaac                           519
```

<210> SEQ ID NO 33
<211> LENGTH: 35
<212> TYPE: DNA
<213> ORGANISM: Artificial Sequence
<220> FEATURE:
<223> OTHER INFORMATION: synthetic construct; zinc binding domain and intein sequence

<400> SEQUENCE: 33

```
ggagagggac atcacctcgc agagggcact cggat                               35
```

<210> SEQ ID NO 34
<211> LENGTH: 35
<212> TYPE: DNA
<213> ORGANISM: Artificial Sequence
<220> FEATURE:
<223> OTHER INFORMATION: synthetic construct; zinc binding motif and intein sequence

<400> SEQUENCE: 34

```
ggagagggac attgcctcgc agagggcact cggat                               35
```

<210> SEQ ID NO 35
<211> LENGTH: 35
<212> TYPE: DNA
<213> ORGANISM: Artificial Sequence
<220> FEATURE:
<223> OTHER INFORMATION: synthetic construct; zinc binding motif and intein sequence

<400> SEQUENCE: 35

```
ggagagggac atcatgccct cgcagagggc actcg                               35
```

<210> SEQ ID NO 36
<211> LENGTH: 36
<212> TYPE: DNA
<213> ORGANISM: Artificial Sequence
<220> FEATURE:
<223> OTHER INFORMATION: synthetic construct; zinc binding motif and intein sequence

<400> SEQUENCE: 36

```
ggagagggac atggatgcct cgcagagggc actcgg                              36
```

<210> SEQ ID NO 37
<211> LENGTH: 37
<212> TYPE: DNA
<213> ORGANISM: Artificial Sequence
<220> FEATURE:
<223> OTHER INFORMATION: synthetic construct; zinc binding motif and intein sequence

<400> SEQUENCE: 37

```
ggagatggac atcatgccct cgcagagggc actcgga                             37
```

<210> SEQ ID NO 38
<211> LENGTH: 37
<212> TYPE: DNA
<213> ORGANISM: Artificial Sequence
<220> FEATURE:
<223> OTHER INFORMATION: synthetic construct; zinc binding motif and intein sequence

<400> SEQUENCE: 38

```
ggagatggac atggatgcct cgcagagggc actcgga                              37
```

<210> SEQ ID NO 39
<211> LENGTH: 10
<212> TYPE: PRT
<213> ORGANISM: Artificial Sequence
<220> FEATURE:
<223> OTHER INFORMATION: synthetic construct; zinc binding motif

<400> SEQUENCE: 39

Gly Glu Gly His His Leu Ala Glu Gly Thr
1               5                   10

<210> SEQ ID NO 40
<211> LENGTH: 10
<212> TYPE: PRT
<213> ORGANISM: Artificial Sequence
<220> FEATURE:
<223> OTHER INFORMATION: synthetic construct; zinc binding motif

<400> SEQUENCE: 40

Gly Glu Gly His Cys Leu Ala Glu Gly Thr
1               5                   10

<210> SEQ ID NO 41
<211> LENGTH: 11
<212> TYPE: PRT
<213> ORGANISM: Artificial Sequence
<220> FEATURE:
<223> OTHER INFORMATION: synthetic construct; zinc binding motif

<400> SEQUENCE: 41

Gly Glu Gly His His Ala Leu Ala Glu Gly Thr
1               5                   10

<210> SEQ ID NO 42
<211> LENGTH: 11
<212> TYPE: PRT
<213> ORGANISM: Artificial Sequence
<220> FEATURE:
<223> OTHER INFORMATION: synthetic construct; zinc binding motif

<400> SEQUENCE: 42

Gly Glu Gly His Gly Cys Leu Ala Glu Gly Thr
1               5                   10

<210> SEQ ID NO 43
<211> LENGTH: 11
<212> TYPE: PRT
<213> ORGANISM: Artificial Sequence
<220> FEATURE:
<223> OTHER INFORMATION: synthetic construct; zinc binding motif

<400> SEQUENCE: 43

Gly Asp Gly His Gly Cys Leu Ala Glu Gly Thr
1               5                   10

<210> SEQ ID NO 44
<211> LENGTH: 11
<212> TYPE: PRT
<213> ORGANISM: Artificial Sequence
<220> FEATURE:
<223> OTHER INFORMATION: synthetic construct; zinc binding motif -continued

```
<400> SEQUENCE: 44

Gly Asp Gly His Gly Cys Leu Ala Glu Gly Thr
1               5                   10
```

COMPOSITIONS RELATED TO CONTROLLABLE INTERVENING PROTEIN SEQUENCES (CIPS) COMPRISING REVERSIBLE ZINC-BINDING MOTIFS AND INTEINS

CROSS-REFERENCE TO RELATED APPLICATIONS

This application claims benefit of U.S. Provisional Application No. 61/678,303, filed Aug. 1, 2012, and U.S. Provisional Application No. 61/777,068, filed Mar. 12, 2013, each of which are hereby incorporated herein by reference in their entirety.

STATEMENT REGARDING FEDERALLY SPONSORED RESEARCH

This invention was made with government support under contract HHSN261200800001E awarded by the National Cancer Institute and the National Institutes of Health. The government has certain rights in the invention.

FIELD OF THE INVENTION

This invention relates to the field of molecular and protein biology including polypeptides and modified polypeptides. This application also relates to the field of protein purification. The present invention also relates generally to the field of protein preparation, protein recovery and protein purification.

BACKGROUND OF THE INVENTION

Inteins are naturally occurring, self-splicing protein subdomains that are capable of excising out their own protein subdomain from a larger protein structure while simultaneously joining the two formerly flanking peptide regions ("exteins") together to form a mature host protein.

The interesting behavior of inteins has led to an emerging area of research regarding the structural, mechanistic, and biological features of inteins. For instance, a variety of x-ray crystal structures, computational models, and mutational studies have led to a general consensus that inteins are distinct from common proteolytic enzymes in that they do not degrade peptide bonds other than the two bonds linking the intein to the flanking "exteins." This is highly useful because unwanted proteolytic damage to other proteins is mitigated when inteins are used as transient coupling elements within fusion proteins.

What is needed is a method for selectively and reversibly inactivating an intein. Such an approach could allow for affinity based purification of a wide variety of proteins. The availability of such a generic protein recovery and purification system would have significant applications in the areas of rapid anti-infectious disease vaccine manufacture, bioterrorism defense, and personalized anti-cancer antigen generation, as well as contributing to the acceleration of new drug evaluation and optimization.

SUMMARY

Disclosed herein are polypeptides, compositions, and methods of making and use of said polypeptides and compositions.

A critical application of inteins has been the development of self-cleaving affinity tags for protein purification. In these applications, the inteins are modified to exhibit isolated cleaving of the intein-extein bonds at either their N- or C-terminus, or both. By replacing one extein with an affinity tag, and the other extein with a desired target protein, the target protein can be easily purified by the tag, where tag removal is subsequently facilitated by the intein self-cleaving activity. Critical to this application, however, is the ability to suppress cleaving during expression of the tagged target protein, but induce rapid self-cleaving of the intein from the purified target protein. This ability had proven elusive, and is critical to the application of inteins to general protein purification methods of using affinity tags for protein purification. In this case critical application of inteins has been the development of self-cleaving activity.

Disclosed herein are modified peptides comprising a controllable intervening protein sequence (CIPS) wherein the modified peptide comprises the structure: X1-CIPS, wherein X1 is an affinity tag, and wherein the CIPS comprises a reversible zinc-binding motif and an intein.

Also disclosed herein are modified peptides comprising a CIPS wherein the modified peptides comprise the structure: X1-CIPS-X2, wherein X1 is an affinity tag, and wherein the CIPS comprises a reversible zinc-binding motif and an intein, and wherein X2 comprises a protein of interest.

Disclosed herein are controllable intervening protein sequences (CIPSs) comprising an intein and a reversible zinc-binding motif wherein the reversible zinc-binding motif comprises the structure: aa1-aa2-aa3-aa4, wherein aa1 is a non-polar amino acid, aa2 is a negatively-charged amino acid, aa3 is a non-polar amino acid and aa4 is a positively charged amino acid.

Disclosed herein are CIPSs comprising an intein and a reversible zinc-binding motif wherein the reversible zinc-binding motif comprises the structure: aa1-aa2-aa3-aa4-aa5, wherein aa1 is a non-polar amino acid, aa2 is a negatively-charged amino acid, aa3 is a non-polar amino acid, aa4 is a positively charged amino acid and aa5 is a non-polar amino acid.

Disclosed herein are isolated nucleic acids capable of encoding the peptides or CIPSs disclosed herein as well as plasmids, vectors, and cell lines comprising nucleic acids capable of encoding the peptides or CIPSs disclosed herein.

Disclosed herein are methods of producing a modified peptide comprising a CIPS, the method comprising: preparing a nucleic acid that encodes one or more peptides comprising a CIPS; transforming a host cell with the nucleic acid; and culturing the transformed host cell under conditions suitable for the expression of the modified peptide comprising a CIPS encoded by the nucleic acid. Such methods can further comprise isolating the modified peptide comprising a CIPS.

Disclosed herein are methods of producing a modified peptide comprising a CIPS, the method comprising: preparing a nucleic acid that encodes one or more peptides comprising a CIPS; transforming a host cell with the nucleic acid; and culturing the transformed host cell under conditions suitable for the expression of the modified peptide comprising a CIPS encoded by the nucleic acid and further comprising exposing the modified peptide comprising the CIPS to a chemical reagent which inhibits splicing or cleavage.

Disclosed herein are methods of producing a modified peptide comprising a CIPS, the method comprising: preparing a nucleic acid that encodes one or more peptides comprising a CIPS; transforming a host cell with the nucleic acid; and culturing the transformed host cell under conditions suitable for the expression of the modified peptide comprising a CIPS encoded by the nucleic acid and further comprising exposing the modified peptide to a chelating agent, a change in pH, a change in temperature, dialysis, or dilution.

Disclosed herein are methods of producing a protein of interest comprising: (a) preparing a nucleic acid that encodes a modified peptide comprising a CIPS wherein the modified peptide comprises the structure: X1-CIPS-X2, wherein X1 is an affinity tag, and wherein the CIPS comprises a reversible zinc-binding motif and an intein, and wherein X2 comprises the protein of interest; (b) transforming a host cell with the nucleic acid; (c) culturing the transformed host cell under conditions suitable for the expression of the modified peptide; (d) exposing the modified peptide to a concentration of zinc which inhibits splicing or cleavage by the CIPS; (e) isolating the modified peptide; and (f) removing the zinc, thereby allowing for splicing or cleavage of the protein of interest from the modified peptide, thereby producing the protein of interest.

Disclosed herein are methods for binding and eluting a phage-displayed polypeptide from a protein of interest comprising: producing a modified peptide comprising the structure X1-CIPS-X2 wherein X1 is an affinity tag, and wherein X2 is a protein of interest; binding the modified peptide to a solid support; contacting a phage-displayed polypeptide with the support-bound modified peptide, thereby permitting binding of the phage-displayed polypeptide with the modified peptide comprising the CIPS; removing unbound phage-displayed polypeptides; and eluting the bound phage-displayed polypeptide by inducing cleavage of the protein of interest by the CIPS.

Disclosed are kits comprising the peptides, vectors, nucleic acids or cells as disclosed herein. The disclosed kits can further comprise zinc.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is in no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF FIGURES

The accompanying figures and drawings, which are incorporated in and constitute a part of this specification, illustrate several aspects and together with the description serve to explain the principles of the invention. These are non-limiting examples.

FIG. 3 shows that inteins isolated from different sources share certain common features. Specifically, almost all inteins end in a histidine-asparagine dipeptide, which can be used to assist in binding metal ions. SEQ ID NOs:51-64 are present in FIG. 3. The sequences read from left to right and top to bottom. For example, SEQ ID NO:51 is AILYVGC-FAKGT and SEQ ID NO:52 is NQVVVHNCGERGN.

Active site configuration showing bound zinc ion. B) Repression of cleaving versus zinc concentration of several constructed mutants.

Figure 11:
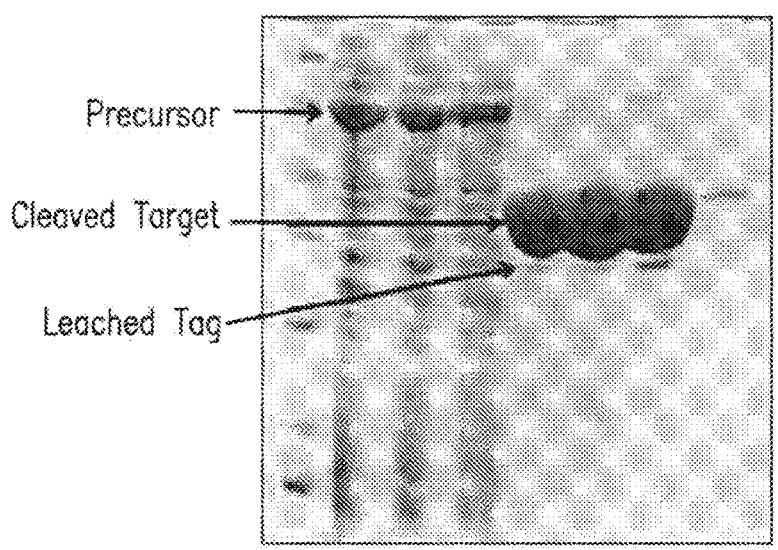

FIG. 11 is a representative single column purification of maltose binding protein (target protein) using a self-cleaving choline binding protein on Q-sepharose.

Figure 12:
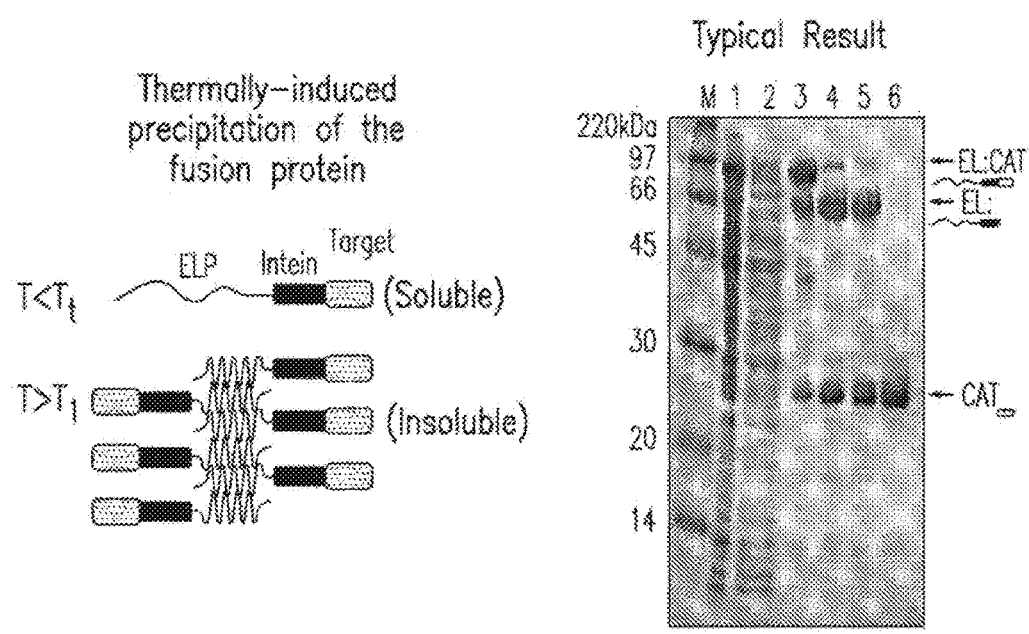

FIG. 12 shows protein purification by self-cleaving ELP precipitation tag.

Figure 13:
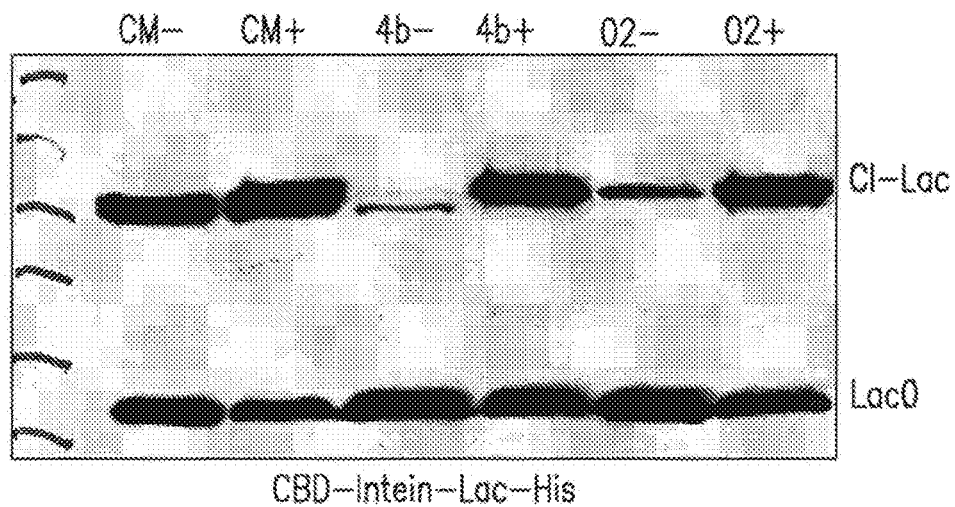

FIG. 13 is a western blot result showing the effect of zinc on premature cleavage in a cell-free expression system. The antibody in the blot is directed to the protein of interest (Lac, or beta-lactamase in this case). CM refers to the parent ΔI-CM intein, while 4b refers to the LN-004b intein and 02 refers to the LN-002 intein. In each case, the '+' symbol indicates expression of the tagged protein in the presence of 300 µM zinc ion, while the '−' symbol indicates the absence of zinc. As can be observed, the CM intein shows very little sensitivity to zinc, and exhibits significant cleavage of the CI-Lac precursor protein to produce cleaved Lac regardless of zinc presence. The 4b and 02 inteins cleave more quickly than the CM intein, and are almost completely cleaved in the absence of zinc, but their cleaving is significantly reduced in the presence of zinc ion.

Figure 14:
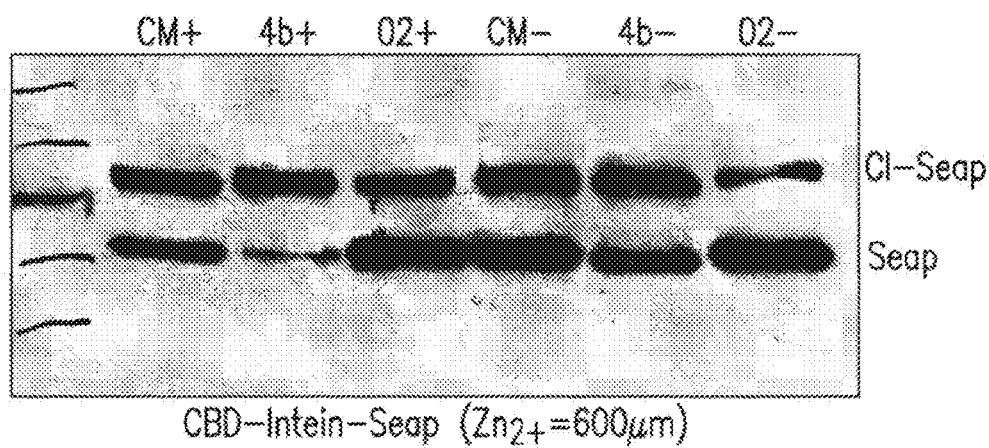

FIG. 14 is a western blot result showing the effect of zinc on premature cleavage in a cell-free expression system. The antibody in the blot is directed to the protein of interest (Seap; Secreted Alkaline Phosphatase). CM refers to the parent ΔI-CM intein, while 4b refers to the LN-004b intein and 02 refers to the LN-002 intein. In each case, the '+' symbol indicates expression of the tagged protein in the presence of 600 µM zinc ion, while the '−' symbol indicates the absence of zinc. As can be observed, the CM intein shows very little sensitivity to zinc, and exhibits significant cleavage of the CI-Seap precursor protein to produce cleaved Seap regardless of zinc presence. The designed inteins are more sensitive to zinc ion, and the 4b intein in particular is almost completely inactivated in the presence of zinc at this concentration. The controllability of the intein is expected to increase with optimized pH and temperature of expression.

Figure 15:
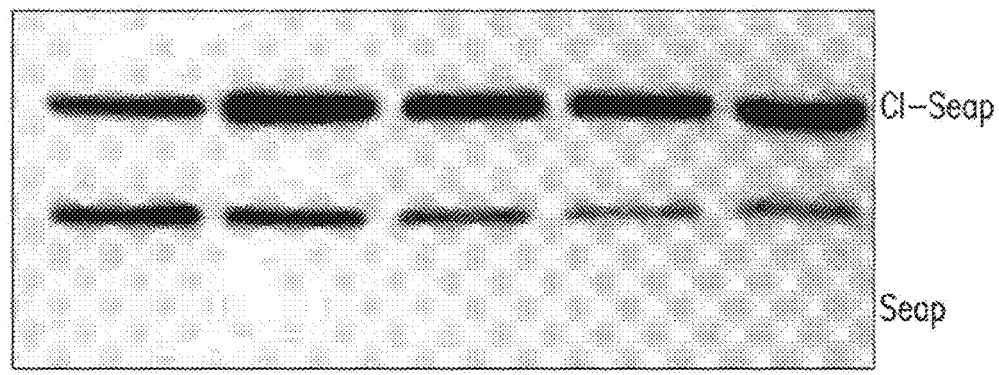

FIG. 15 is a western blot result showing the effect of different zinc concentrations on premature cleavage of the LN-004b intein in a cell-free expression system. The antibody in the blot is directed to the protein of interest (Seap; Secreted Alkaline Phosphatase). In each case, the zinc concentration is noted above each lane. As can be observed, the amount of premature cleaving is reduced as the zinc concentration increases. It is anticipated that a higher degree of control will be attained through optimization of pH and temperature of expression.

Figure 16:
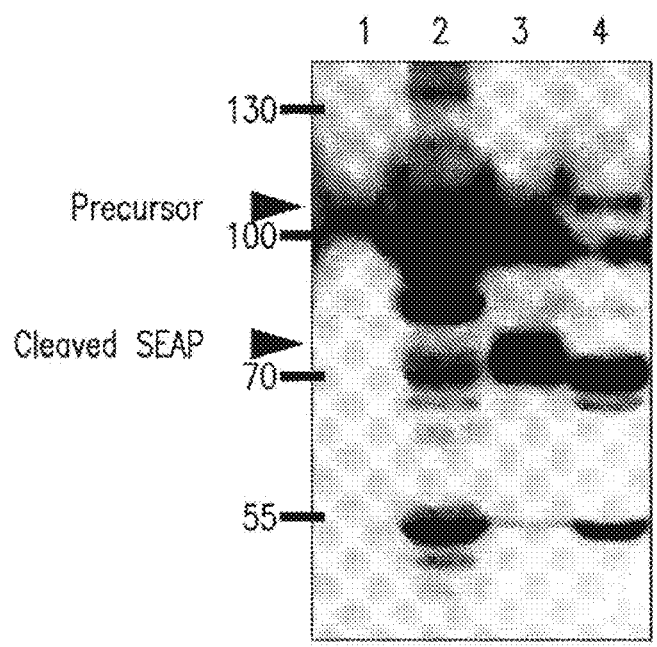

FIG. 16 shows results of CHO expression of Fc-Intein-SEAP at 37° C., 5% CO2 incubation, and harvested 72 h after transfection. Lane 1: The secreted form of Fc-I-SEAP precursor in the presence of 200 µM of Zinc. Lane 2: The intracellular Fc-I-SEAP precursor and cleaved SEAP in the presence of 200 µM of Zinc. Lane 3: The secreted form of Fc-I-SEAP precursor in the absence of 200 µM of Zinc. Lane 4: The intracellular Fc-I-SEAP precursor and cleaved SEAP in the absence of 200 µM of Zinc. Numbers to the left of the gel indicate molecular weights of the predicted species. Note the presence of significant cleaved SEAP in the absence of zinc (lane 3), while no cleaved SEAP is observed in the secreted products in the presence of zinc (lane 1).

FIG. 17 is a table showing the Zinc Binding Motifs (ZBMs), Intein Sequences, and ZBM plus Intein Sequences.

Figure 18:

FIG. 18 is a ribbon diagram of ΔI-CM mini intein.

Figure 19:
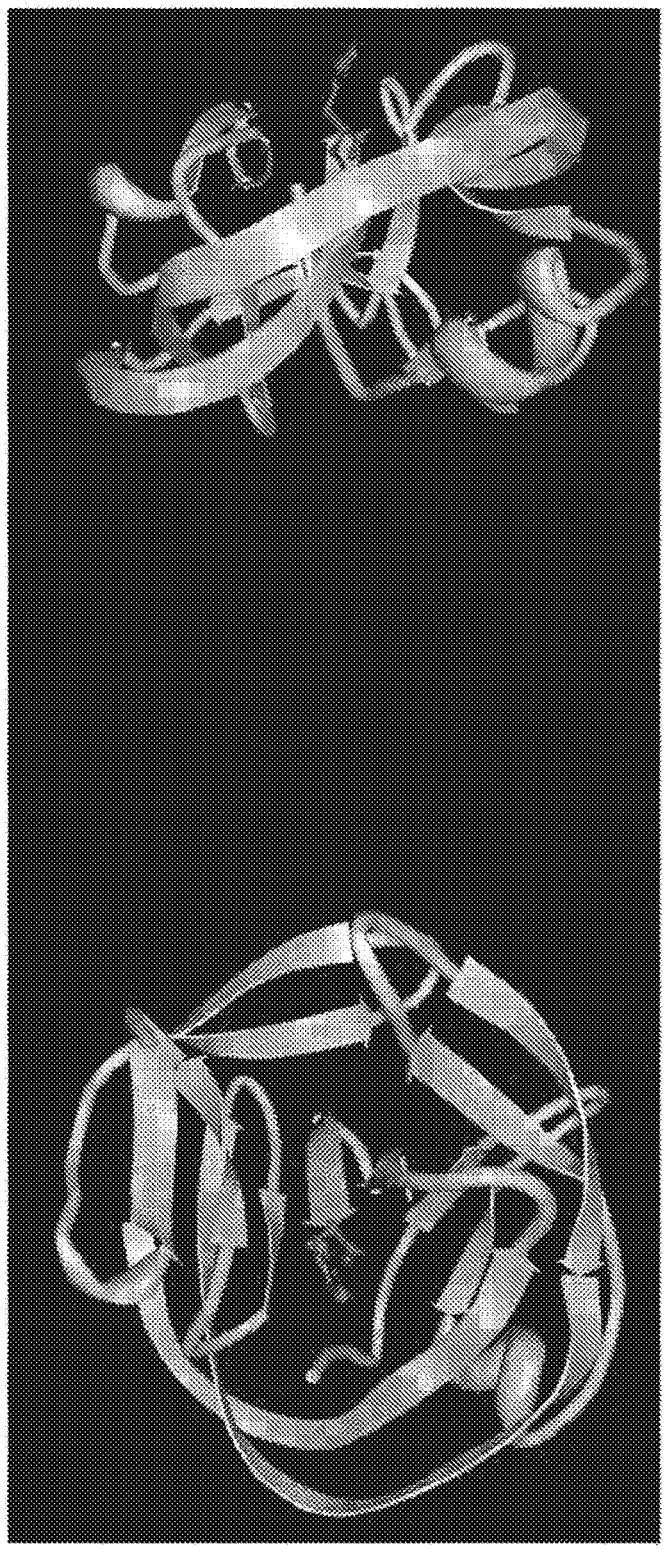

FIG. 19 is a ribbon diagram of ΔI-CM mini intein with the conserved His residue shown in ball-and-stick.

Figure 20:
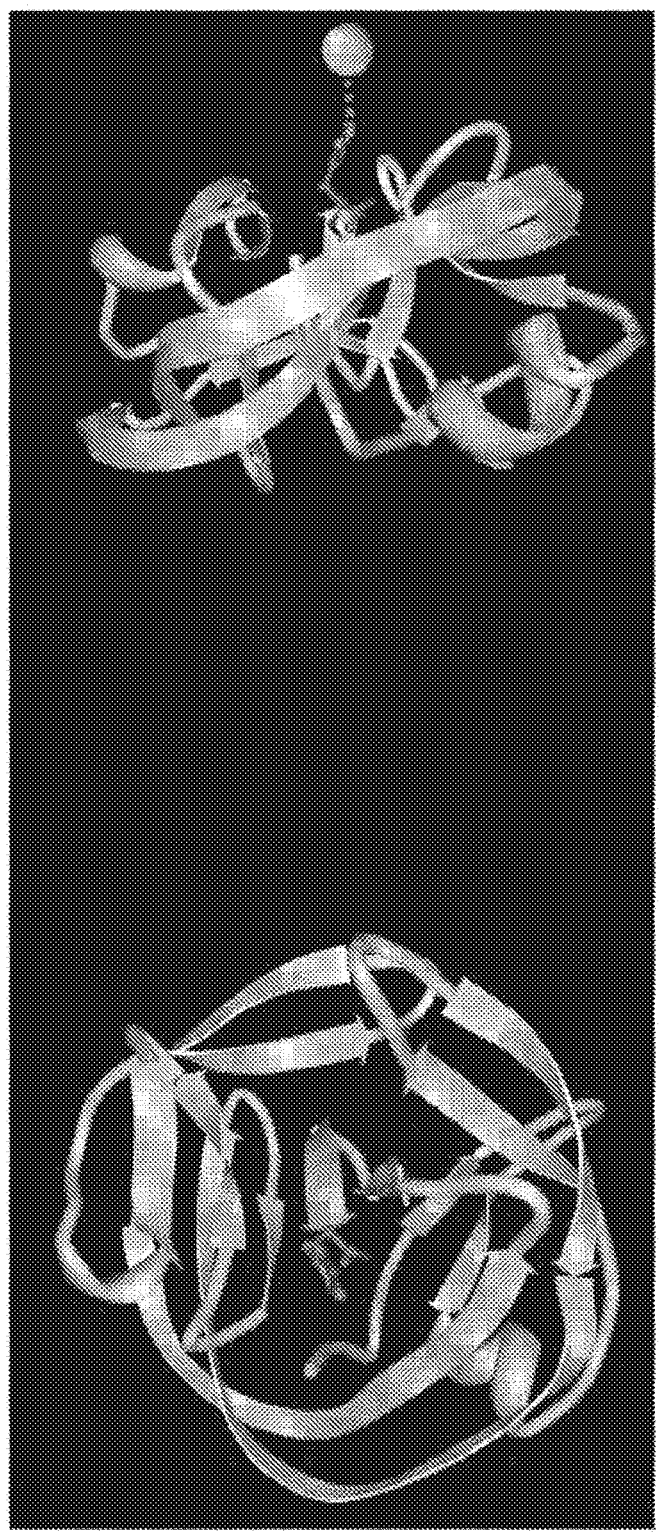

FIG. 20 is a ribbon diagram of ΔI-CM mini intein with the conserved His residue shown in ball-and-stick along with zinc.

Figure 21:
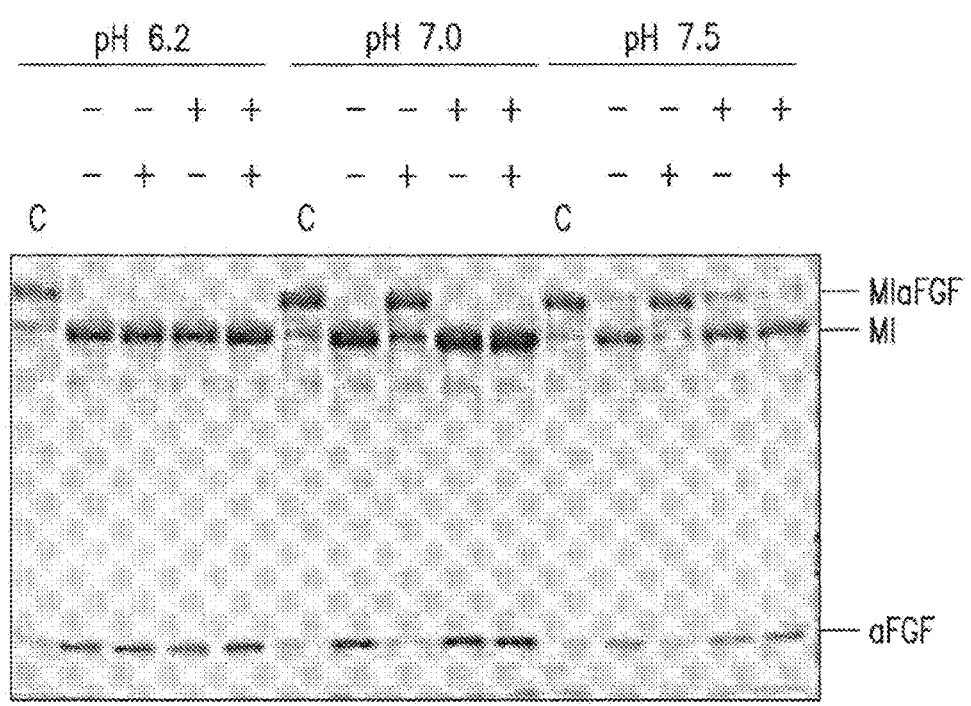

FIG. 21 is a protein gel showing the zinc control of parent ΔI-CM Intein cleaving.

Figure 22A:
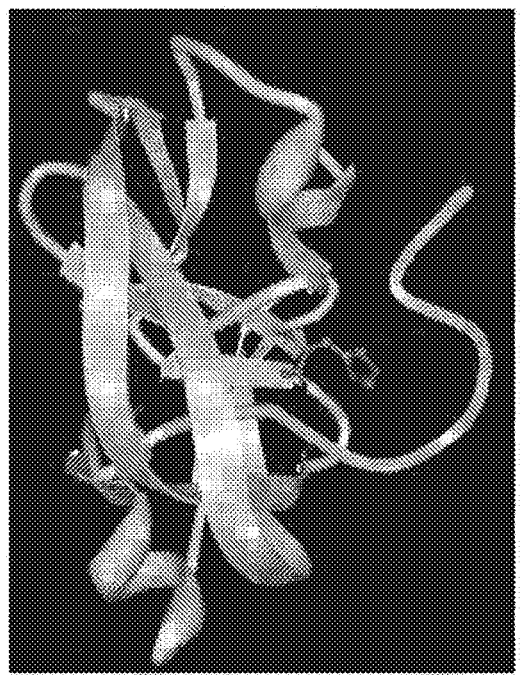
Figure 22B:
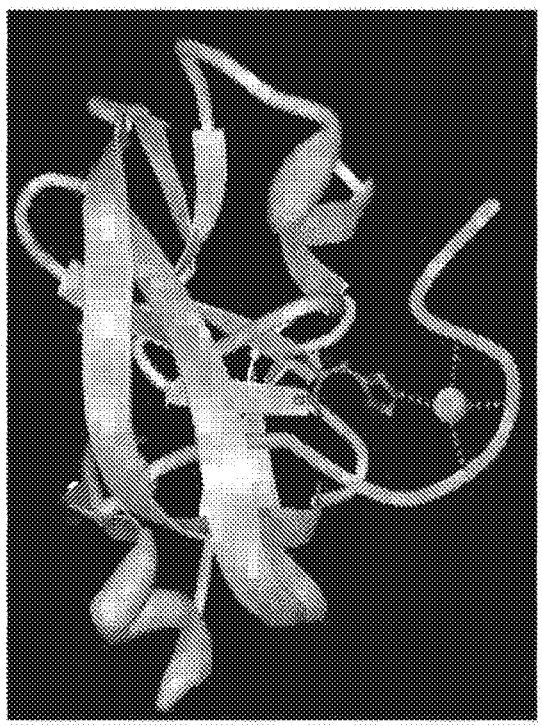

FIGS. 22A and 22B are ribbon diagrams of ΔI-CM mini intein with the conserved His residue shown in ball-and-stick. A) Shows the zinc binding motif added to the N-terminus of the intein. B) Shows zinc interacting with zinc binding motif and His residue.

Figure 23A:
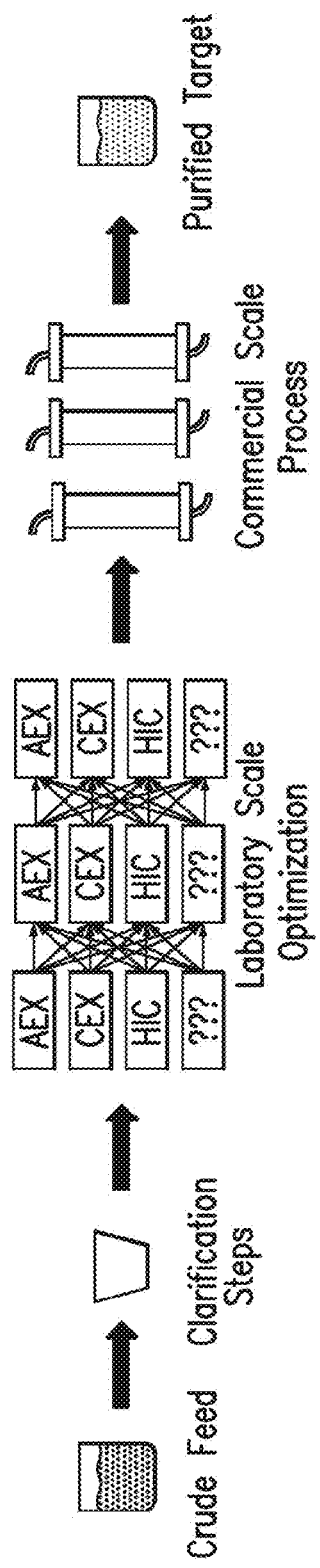
Figure 23B:
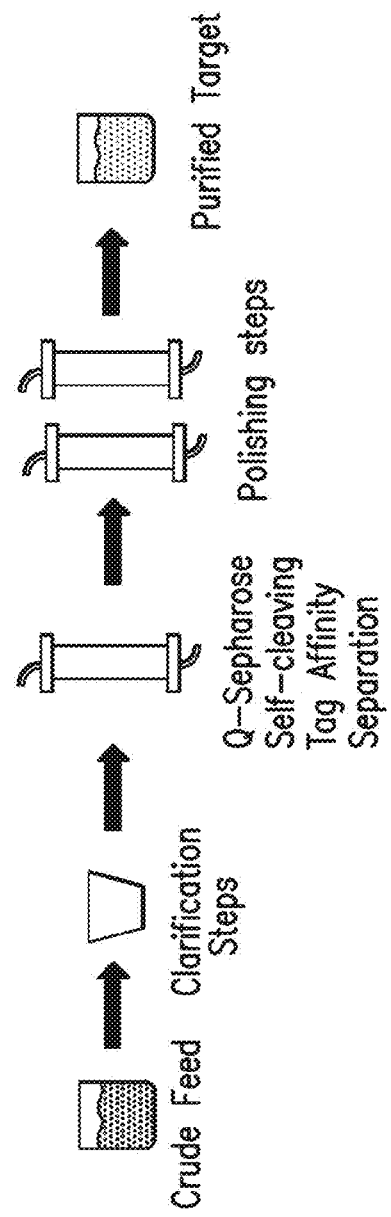

FIGS. 23A and 23B are schematic diagrams of a conventional (A) and a self-cleaving tag-based (B) purification method for comparison.

Additional advantages of the disclosed compositions and methods will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

All patents, patent applications, and publications cited herein, whether supra or infra, are hereby incorporated by reference in their entireties into this application in order to more fully describe the state of the art as known to those skilled therein as of the date of the invention described and claimed herein.

It is to be understood that this invention is not limited to specific synthetic methods, or to specific recombinant biotechnology methods unless otherwise specified, or to particular reagents unless otherwise specified, to specific pharmaceutical carriers, or to particular pharmaceutical formulations or administration regimens, as such may, of course, vary. It is also to be understood that the terminology used herein is for the purpose of describing particular embodiments only and is not intended to be limiting.

Definitions and Nomenclature

The terminology used herein is for the purpose of describing particular embodiments only and is not intended to be limiting. Unless defined otherwise, all technical and scientific terms used herein have the meaning commonly understood by a person skilled in the art.

As used in the specification and the appended claims, the singular forms "a," "an" and "the" can include plural referents unless the context clearly dictates otherwise. Thus, for example, reference to "a compound" includes mixtures of compounds, reference to "a pharmaceutical carrier" includes mixtures of two or more such carriers, and the like.

Ranges may be expressed herein as from "about" one particular value, and/or to "about" another particular value. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, the term "amino acid sequence" refers to a list of abbreviations, letters, characters or words representing amino acid residues. The amino acid abbreviations used herein are conventional one letter codes for the amino acids and are expressed as follows: A, alanine; C, cysteine; D aspartic acid; E, glutamic acid; F, phenylalanine; G, glycine; H histidine; I isoleucine; K, lysine; L, leucine; M, methionine; N, asparagine; P, proline; Q, glutamine; R, arginine; S, serine; T, threonine; V, valine; W, tryptophan; Y, tyrosine.

"Peptide" as used herein refers to any peptide, oligopeptide, polypeptide, gene product, expression product, or protein. A peptide is comprised of consecutive amino acids. The term "peptide" encompasses naturally occurring or synthetic molecules.

In addition, as used herein, the term "peptide" refers to amino acids joined to each other by peptide bonds or modified peptide bonds, e.g., peptide isosteres, etc. and may contain modified amino acids other than the 20 gene-encoded amino acids. The peptides can be modified by either natural processes, such as post-translational processing, or by chemical modification techniques which are well known in the art. Modifications can occur anywhere in the peptide, including the peptide backbone, the amino acid side-chains and the amino or carboxyl termini. The same type of modification can be present in the same or varying degrees at several sites in a given polypeptide. Also, a given peptide can have many types of modifications. Modifications include, without limitation, linkage of distinct domains or motifs, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation, GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983)).

As used herein, "isolated peptide" or "purified peptide" is meant to mean a peptide (or a fragment thereof) that is substantially free from the materials with which the peptide is normally associated in nature. The peptides disclosed herein, or fragments thereof, can be obtained, for example, by extraction from a natural source (for example, a mammalian cell), by expression of a recombinant nucleic acid encoding the peptide (for example, in a cell or in a cell-free translation system), or by chemically synthesizing the peptide. In addition, peptide fragments may be obtained by any of these methods, or by cleaving full length proteins and/or peptides.

The word "or" as used herein means any one member of a particular list and also includes any combination of members of that list.

The phrase "nucleic acid" as used herein refers to a naturally occurring or synthetic oligonucleotide or polynucleotide, whether DNA or RNA or DNA-RNA hybrid, single-stranded or double-stranded, sense or antisense, which is capable of hybridization to a complementary nucleic acid by Watson-Crick base-pairing. Nucleic acids of the invention can also include nucleotide analogs (e.g., BrdU), and non-phosphodiester internucleoside linkages (e.g., peptide nucleic acid (PNA) or thiodiester linkages). In particular, nucleic acids can include, without limitation, DNA, RNA, cDNA, gDNA, ssDNA, dsDNA or any combination thereof.

As used herein, "isolated nucleic acid" or "purified nucleic acid" is meant to mean DNA that is free of the genes that, in the naturally-occurring genome of the organism from which the DNA of the invention is derived, flank the gene. The term therefore includes, for example, a recombinant DNA which is incorporated into a vector, such as an autonomously replicating plasmid or virus; or incorporated into the genomic DNA of a prokaryote or eukaryote (e.g., a transgene); or which exists as a separate molecule (for example, a cDNA or a genomic or cDNA fragment produced by PCR, restriction endonuclease digestion, or chemical or in vitro synthesis). It also includes a recombinant DNA which is part of a hybrid gene encoding additional polypeptide sequences. The term "isolated nucleic acid" also refers to RNA, e.g., an mRNA molecule that is encoded by an isolated DNA molecule, or that is chemically synthesized, or that is separated or substantially free from at least some cellular components, for example, other types of RNA molecules or peptide molecules.

As used herein, "extein" refers to the portion of an intein-modified protein that is not part of the intein and which can be spliced or cleaved upon excision of the intein.

"Intein" refers to an in-frame intervening sequence in a protein. An intein can catalyze its own excision from the protein through a post-translational protein splicing process to yield the free intein and a mature protein. An intein can also catalyze the cleavage of the intein-extein bond at either the intein N-terminus, or the intein C-terminus, or both of the intein-extein termini. As used herein, "intein" encompasses mini-inteins, modified or mutated inteins, and split inteins.

As used herein, "protein of interest" or "peptide of interest" is a protein or peptide sought to be produced, made or purified. A protein or peptide of interest can be attached to an intein in one or more of the peptides disclosed herein comprising a CIPS. A "peptide of interest" can be a protein, such as an enzyme. The terms "protein of interest" and "peptide of interest" can be used interchangeably throughout the specification.

As used herein, "zinc-sensitive" means that a given peptide is responsive to or influenced by the presence of zinc. For example, a "zinc-sensitive" intein responds differently in the presence of zinc than in the absence of zinc.

As used herein, "variant" refers to a molecule that retains a biological activity that is the same or substantially similar to that of the original sequence. The variant may be from the same or different species or be a synthetic sequence based on a natural or prior molecule. Moreover, as used herein, "variant" refers to a molecule having a structure attained from the structure of a parent molecule (e.g., a protein or peptide disclosed herein) and whose structure or sequence is sufficiently similar to those disclosed herein that based upon that similarity, would be expected by one skilled in the art to exhibit the same or similar activities and utilities compared to the parent molecule. For example, substituting specific amino acids in a given peptide can yield a variant peptide with similar activity to the parent.

Nucleic acids, nucleotide sequences, proteins or amino acid sequences referred to herein can be isolated, purified, synthesized chemically, or produced through recombinant DNA technology. All of these methods are well known in the art.

As used herein, the terms "modified" or "mutated," as in "modified intein" or "mutated intein," refer to one or more modifications in either the nucleic acid or amino acid sequence being referred to, such as an intein, when compared to the native, or naturally occurring structure. Such modification can be a substitution, addition, or deletion. The modification can occur in one or more amino acid residues or one or more nucleotides of the structure being referred to, such as an intein.

As used herein, the term "modified peptide", "modified protein" or "modified protein of interest" or "modified target protein" refers to a protein which has been modified. For example a modified peptide can be a peptide modified by the insertion of a CIPS. A modified peptide can also comprise a CIPS as well as a protein of interest and/or an affinity tag.

As used herein, "operably linked" refers to the association of two or more biomolecules in a configuration relative to one another such that the normal function of the biomolecules can be performed. In relation to nucleotide sequences, "operably linked" refers to the association of two or more nucleic acid sequences, by means of enzymatic ligation or otherwise, in a configuration relative to one another such that the normal function of the sequences can be performed. For example, the nucleotide sequence encoding a pre-sequence or secretory leader is operably linked to a nucleotide sequence for a polypeptide if it is expressed as a pre-protein that participates in the secretion of the polypeptide; a promoter or enhancer is operably linked to a coding sequence if it affects the transcription of the coding sequence; and a ribosome binding site is operably linked to a coding sequence if it is positioned so as to facilitate translation of the sequence.

"Sequence homology" can refer to the situation where nucleic acid or protein sequences are similar because they have a common evolutionary origin. "Sequence homology" can indicate that sequences are very similar. Sequence similarity is observable; homology can be based on the observation. "Very similar" can mean at least 70% identity, homology or similarity; at least 75% identity, homology or similarity; at least 80% identity, homology or similarity; at least 85% identity, homology or similarity; at least 90% identity, homology or similarity; such as at least 93% or at least 95% or even at least 97% identity, homology or similarity. The nucleotide sequence similarity or homology or identity can be determined using the "Align" program of Myers et al. (1988) CABIOS 4:11-17 and available at NCBI. Additionally or alternatively, amino acid sequence similarity or identity or homology can be determined using the BlastP program (Altschul et al. Nucl. Acids Res. 25:3389-3402), and available at NCBI. Alternatively or additionally, the terms "similarity" or "identity" or "homology," for instance, with respect to a nucleotide sequence, are intended to indicate a quantitative measure of homology between two sequences.

Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipman algorithm. (1983) Proc. Natl. Acad. Sci. USA 80:726. For example, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity with DNA sequences, thymidine (T) in the DNA sequence is considered equal to uracil (U) in the RNA sequence. The following references also provide algorithms for comparing the relative identity or homology or similarity of amino acid residues of two proteins, and additionally or alternatively with respect to the foregoing, the references can be used for determining percent homology or identity or similarity. Needleman et al. (1970) J. Mol. Biol. 48:444-453; Smith et al. (1983) Advances App. Math. 2:482-489; Smith et al. (1981) Nuc. Acids Res. 11:2205-2220; Feng et al. (1987) J. Molec. Evol. 25:351-360; Higgins et al. (1989) CABIOS 5:151-153; Thompson et al. (1994) Nuc. Acids Res. 22:4673-480; and Devereux et al. (1984) 12:387-395. "Stringent hybridization conditions" is a term which is well known in the art; see, for example, Sambrook, "Molecular Cloning, A Laboratory Manual" second ed., CSH Press, Cold Spring Harbor, 1989; "Nucleic Acid Hybridization, A Practical Approach", Hames and Higgins eds., IRL Press, Oxford, 1985; see also FIG. 2 and description thereof herein wherein there is a sequence comparison.

The terms "plasmid" and "vector" and "cassette" refer to an extra chromosomal element often carrying genes which are not part of the central metabolism of the cell and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. Typically, a "vector" is a modified plasmid that contains additional multiple insertion sites for cloning and an "expression cassette" that contains a DNA sequence for a selected gene product (i.e., a transgene) for expression in the host cell. This "expression cassette" typically includes a 5' promoter region, the transgene ORF, and a 3' terminator region, with all necessary regulatory sequences required for transcription and translation of the ORF. Thus, integration of the expression cassette into the host permits expression of the transgene ORF in the cassette.

Controllable Intervening Protein Sequences

A variety of intein-mediated, affinity tagged intein systems are known in the art but critically suffer from a lack of a sufficient or industrially convenient control approach for the self-release step. Previous approaches have relied on pH or temperature as a triggering mechanism for the activation of intein self-cleavage, but these schemes require expression conditions that are not suitable for commercially relevant mammalian cell culture expression systems. Furthermore, these triggering mechanisms have historically suffered from premature intein activation, lengthened process time due to low temperature growth, incompatibility with certain naturally occurring protein bonds, and suboptimal target protein yields. These deficiencies have limited the practical application of inteins and as a consequence, the promise of the technology has not been fully realized.

Current self-cleaving intein systems fall into two categories: N-terminal cleaving systems, which require high concentrations of thiol compounds to induce cleaving, and C-terminal cleaving inteins, which are controlled by pH and temperature. N-terminal cleaving inteins cannot be used with target proteins that contain disulfide bonds due to the tendency of thiol compounds to break these bonds and destroy the target. C-terminal cleaving inteins are plagued with premature cleaving problems, where the tag self-cleaves before the target can actually be purified. These two limitations have effectively prevented intein technology from being applied to proteins expressed in mammalian cells, and these proteins comprise a large and growing majority of biopharmaceuticals.

Previously, inteins were engineered through the application of directed evolution methods. One of these inteins, derived from the Mtu-RecA intein, commonly referred to as the ΔI-CM mini intein, was optimized to obtain 1) a small physical size, 2) significant cleaving activity, and 3) selective activation under modulated solution temperature and pH conditions. The ΔI-CM intein (FIG. 17, in the Examples section) has been successfully applied to the expression of intact tag-intein-payload fusion proteins in E. coli. However, premature intein activation is a significant drawback, and low temperature protein expression (below 25° C.) is used to maximize the proportion of intact fusion protein available for affinity capture. However, this condition substantially lengthens process time. Further, and most critically, this need for low-temperature expression conditions prevents the use of the ΔI-CM intein in the most commercially relevant mammalian cell culture based expression systems, which require growth and expression at temperatures above 32° C. and neutral pH. Clearly, a method for selectively and reversibly inactivating an intein is needed. Such methods and compositions are provided herein.

Disclosed herein are controllable intervening protein sequences (CIPS), which comprise an intein engineered to possess an appended (or internal) zinc-binding control subdomain (also referred to herein as a "zinc-binding motif," or "ZBM"). These CIPS can be used to modify or in modified peptides and are useful for a variety of methods including, but not limited to, protein production and purification. For example, disclosed herein are modified peptides comprising a CIPS. Also disclosed herein are modified peptides comprising a CIPS wherein the modified peptide comprises the structure: X1-CIPS, wherein X1 is an affinity tag, and wherein the CIPS comprises a reversible zinc-binding motif and an intein.

Disclosed herein are modified peptides comprising a CIPS. Also disclosed herein are modified peptides comprising a CIPS wherein the modified peptide comprises the structure: X1-CIPS, wherein X1 is an affinity tag, and wherein the CIPS comprises a reversible zinc-binding motif and an intein, wherein the intein is a naturally occurring intein, a modified intein, Mtu-RecA or one of the inteins listed in Table 2.

Disclosed herein are modified peptides comprising a CIPS.

Disclosed herein are modified peptides comprising a CIPS wherein the modified peptide comprises the structure: X1-CIPS, wherein X1 is an affinity tag, and wherein the CIPS comprises a reversible ZBM and an intein, wherein the intein comprises additional amino acids at the N-terminus of a naturally occurring intein. For example, the modified intein can comprise four or more additional amino acids at the N-terminus of the naturally occurring intein. In some aspects, the modified intein can comprise four or more additional amino acids at the N-terminus of the naturally occurring intein, wherein the first amino acid at the N-terminal end of the intein is alanine, histidine, cysteine or glycine.

Also disclosed herein are modified peptides comprising a CIPS wherein the modified peptide comprises the structure: X1-CIPS-X2, wherein X1 is an affinity tag, and wherein the CIPS comprises a reversible ZBM and an intein, and wherein X2 comprises a protein of interest.

Additional examples of CIPS can be further found in FIG. 17, as well as in the Examples section below. For example, the CIPS can comprise SEQ ID NOS: 11, 15, 19, 23, 27, or 31. A nucleic acid encoding a CIPS can comprise SEQ ID NOS: 12, 16, 20, 24, 28, or 32.

Also disclosed herein are splicing-intein variants of the described system that can be used to alter the tropism of viral, bacterial, or yeast vectors through the introduction of interrupting switched inteins into key vector surfaces or targeting proteins, thereby making the vectors inhibited by the presence of zinc and activated by chelating agents which bind zinc.

As discussed herein, the CIPSs disclosed herein comprise a reversible ZBM linked to an intein. The ZBM can be attached to the N-terminus or the C-terminus of the intein, or can be within the intein.

The ZBM can allow for the pulling away of the active site histidine into a metal-nitrogen chelation arrangement such that it is no longer available to activate the labile peptide bond for cission.

Disclosed herein are modified peptides comprising a ZBM which allows for enhanced binding of zinc when compared to an intein without a ZBM in which enhanced binding of zinc allows the bound zinc to interact with one or the other of two critical active site histidine residues.

The ZBM can be reversible. By "reversible" it is meant that the motif binds zinc when it is present, which can alter the behavior of the intein to which the ZBM is attached. This behavior of the intein, however, is reversible when zinc is removed. For example, an intein may cleave or splice when zinc is not present. However, this action can be inhibited in the presence of zinc. When the zinc is removed, however, because the action is reversible, the intein will continue to perform the activity which it would have done, had zinc not been present, such as cleaving or splicing. In some aspects, other divalent metals within the fourth row transition element series, other than zinc, can be used in the disclosed methods. Examples of other divalent metals within the fourth row transition element include, but are not limited to, titanium, vanadium, chromium, nickel, copper, manganese, iron, and cobalt.

The ZBMs disclosed herein can be designed such that when appended to, for example, the N-terminal portion of an intein, such as the Mtu-RecA intein, they introduce a zinc-binding, active-site modulating subdomain capable of reversibly switching the intein off. This sensitivity to zinc has enabled the successful use of the inteins under conditions that are compatible with commercially relevant mammalian cell culture expression platforms. For example, a reversible ZBM can be fused directly to the N-terminal end of the intein, with no linkers or additional amino acids separating the intein from the ZBM.

Disclosed herein are modified peptides comprising a CIPS. Also disclosed herein are peptides comprising a CIPS wherein the modified peptide comprises the structure:

X1-CIPS, wherein X1 is an affinity tag, and wherein the CIPS comprises a reversible zinc-binding motif and an intein.

Disclosed herein are CIPSs comprising an intein and a reversible ZBM, wherein the reversible ZBM comprises the structure: aa1-aa2-aa3-aa4, wherein aa1 is a non-polar amino acid, aa2 is a negatively-charged amino acid, aa3 is a non-polar amino acid and aa4 is a positively charged amino acid. For example, aa1 can be glycine, alanine, isoleucine, leucine, methionine, phenylalanine, proline, tryptophan, or valine; aa2 can be aspartic acid or glutamic acid; aa3 can be glycine, alanine, isoleucine, leucine, methionine, phenylalanine, proline, tryptophan, or valine; and aa4 can be arginine or lysine.

Disclosed herein are CIPSs comprising an intein and a reversible ZBM, wherein the reversible ZBM comprises the sequence: G-E-G-H (SEQ ID NO: 1) or G-D-G-H (SEQ ID NO: 2).

Disclosed herein are CIPSs comprising an intein and a reversible ZBM, wherein the reversible ZBM comprises the structure: aa1-aa2-aa3-aa4-aa5, wherein aa1 is a non-polar amino acid, aa2 is a negatively-charged amino acid, aa3 is a non-polar amino acid, aa4 is a positively charged amino acid and aa5 is a non-polar amino acid. For example, aa1 can be glycine, alanine, isoleucine, leucine, methionine, phenylalanine, proline, tryptophan, or valine; aa2 can be aspartic acid or glutamic acid or cysteine; aa3 can be glycine, alanine, isoleucine, leucine, methionine, phenylalanine, proline, tryptophan, or valine; aa4 can be arginine or lysine; and aa5 can be glycine, alanine, isoleucine, leucine, methionine, phenylalanine, proline, tryptophan, or valine.

Disclosed herein are CIPSs comprising an intein and a reversible ZBM, wherein the reversible ZBM comprises the sequence G-E-G-H-H (SEQ ID NO: 3), G-E-G-H-G (SEQ ID NO: 4), G-D-G-H-H (SEQ ID NO: 5), or G-D-G-H-G (SEQ ID NO: 6).

The corresponding nucleic acid sequences for the above ZBMs follow. Note that the underlined portion of the nucleic acid encodes the reversible ZBM, as well as the nucleic acid which codes for the first amino acid of the intein.

```
                                      (SEQ ID NO: 1)
GEGH (SEQ ID NO: 33)
GGAGAGGGACATCACCTCGCAGAGGGCACTCGGAT (SEQ ID NO: 1)
GEGH (alternate sequence encoding first amino
acid of intein)

(SEQ ID NO: 34)
GGAGAGGGACATTGCCTCGCAGAGGGCACTCGGAT (SEQ ID NO: 3)
GEGHH (SEQ ID NO: 35)
GGAGAGGGACATCATGCCCTCGCAGAGGGCACTCG (SEQ ID NO: 4)
GEGHG (SEQ ID NO: 36)
GGAGAGGGACATGGATGCCTCGCAGAGGGCACTCGG (SEQ ID NO: 5)
GDGHH (SEQ ID NO: 37)
GGAGATGGACATCATGCCCTCGCAGAGGGCACTCGGA
```

```
-continued
                                      (SEQ ID NO: 6)
GDGHG (SEQ ID NO: 38)
GGAGATGGACATGGATGCCTCGCAGAGGGCACTCGGA
```

FIG. 17 shows examples of various reversible ZBMs, as well as these ZBMs linked to an intein.

The CIPSs described herein can be engineered to possess an intein wherein the appended zinc-binding motif is placed (1) at a specific location near the intein's enzyme active site or (2) at other similar sites that either can directly or allosterically control the intein's active site dynamics and conformations. In some aspects, the CIPS can be engineered in a way that when the CIPS is exposed to zinc, the splicing rate can be decreased by 5, 10, 15, 20, 25, 30, 35, 40, 45, 50, 55, 60, 65, 70, 75, 80, 85, 90, 95, or 100% when compared to an intein which has not been modified to comprise a zinc-binding domain. In the case where a Divalent Cation Binding Motif (DCBM) is used rather than a ZBM, the CIPS can be engineered in a way that when the CIPS is exposed to a divalent metal within the fourth row transition element series, the splicing rate can be decreased by 5, 10, 15, 20, 25, 30, 35, 40, 45, 50, 55, 60, 65, 70, 75, 80, 85, 90, 95, or 100% when compared to an intein which has not been modified to comprise a DCBM.

Because the ZBM can be reversible, when the peptide comprising the CIPS is exposed to a chelating agent, a change in pH, dialysis, or dilution, thereby removing zinc, the CIPS can excise the intein portion out by protein splicing, or cleavage in the absence of splicing. In some aspects, the modified peptide (comprising a CIPS, an affinity tag, and/or a protein of interest) can be subjected to these conditions. The CIPS may also be inserted into a region that substantially inhibits the activity of the protein of interest.

In some aspects, the zinc ion can be removed by a shift to a pH below 7.0, which can cause zinc loss via protonation of the chelating histidine residues. In some aspects, the zinc ion can be removed, for example, by addition of EDTA (Ethylenediaminetetraacetic acid) or EGTA (ethylene glycol tetraacetic acid) to directly chelate the zinc ion. In some aspects, the zinc ion can be removed by dilution to a concentration below that required for intein inhibition, or by dialysis to remove the zinc ion from the intein. In some aspects, the zinc ion can be removed by buffer wash with an immobilized CIPS in a column chromatography format.

In some aspects, a CIPS can be engineered such that when zinc is present at a concentration of 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 750, 800, 850, 900, 1000, 1100, 1200, 1300, 1400, 1500, or more µM, the CIPS splicing activity can be prevented or reduced. One of skill in the art can readily ascertain the appropriate amount of zinc required to prevent specific intein portions of the CIPS from splicing or cleaving.

In some aspects, the CIPSs disclosed herein comprise a reversible DCBM linked to an intein. The DCBM can be attached to the N-terminus or the C-terminus of the intein, or can be within the intein. For example, disclosed herein are modified peptides comprising a CIPS wherein the modified peptide comprises the structure: X1-CIPS, wherein X1 is an affinity tag, and wherein the CIPS comprises a reversible DCBM and an intein, wherein the intein comprises additional amino acids at the N-terminus of a naturally occurring intein. As used herein, a DCBM can be used instead of a ZBM, thereby allowing for other divalent metal ions to control the intein function.

As discussed herein, the CIPSs disclosed herein can comprise a reversible DCBM linked to an intein. The DCBM can be attached to the N-terminus or the C-terminus of the intein, or can be within the intein.

The DCBM can allow for the pulling away of the active site histidine into a metal-nitrogen chelation arrangement such that it is no longer available to activate the labile peptide bond for cission.

The DCBM can allow for enhanced binding of divalent metals within the fourth row transition element series when compared to an intien without a DCBM in which enhanced binding of a divalent metal within the fourth row transition element series allows the bound divalent metals within the fourth row transition element series to interact with one or the other of two critical active site histidine residues.

As described throughout, the DCBM and the corresponding divalent metal within the fourth row transition element series can be used as described herein for the ZBM and zinc so far as they relate to the methods and compositions described herein.

In Table 1, below, is a list of the various amino acids, their abbreviations, as well as their polarity and charge. Using this table, one of skill in the art can readily ascertain which amino acids can be used in the peptide compositions disclosed herein.

As discussed herein, the CIPSs disclosed herein comprise an intein. One way to control protein activity is through the use of inteins which can allow expression of an intein modified protein with a predefined activity level. As discussed herein, inteins are self-cleaving and self-ligating peptides. The collective attributes of being both self-cleaving and self-ligating are referred to as "self-splicing" or "splicing." An intein cleaves from the protein and mediates ligation of the protein sequences (exteins) from which it cleaves to splice the protein. An intein may be inserted within the protein sequence or fused terminally to the protein. An intein insertion in a protein may allow control of a protein by yielding a modified protein that has one activity when the intein is present and another activity after intein cleavage or splicing. In some cases, the intein splicing reaction can be controlled by one or more of a variety of induction conditions, such as zinc, when the proper modification has been made to the intein. When an activity normally detrimental to the host is reduced, the intein protects the expression host from detrimental growth, physiological, or yield effects of the protein. After expression of the protein, the activity can be changed by exposing the modified protein to reaction conditions that induce intein splicing (such as removal of zinc by the methods disclosed herein). In one aspect, the modified protein that results after splicing has increased activity. Inteins can also be used in protein purification systems, described below.

TABLE 1

| Amino Acids | | | | |
| --- | --- | --- | --- | --- |
| Amino Acid | 3-Letter Code | 1-Letter Code | Polarity | Charge |
| Alanine | Ala | A | nonpolar | neutral |
| Arginine | Arg | R | Basic polar | positive |
| Asparagine | Asn | N | polar | neutral |
| Aspartic acid | Asp | D | acidic polar | negative |
| Cysteine | Cys | C | nonpolar | neutral |
| Glutamic acid | Glu | E | acidic polar | negative |
| Glutamine | Gln | Q | polar | neutral |
| Glycine | Gly | G | nonpolar | neutral |
| Histidine | His | H | Basic polar | Positive (10%) Neutral (90%) |
| Isoleucine | Ile | I | nonpolar | neutral |
| Leucine | Leu | L | nonpolar | neutral |
| Lysine | Lys | K | Basic polar | positive |
| Methionine | Met | M | nonpolar | neutral |
| Phenylalanine | Phe | F | nonpolar | neutral |
| Proline | Pro | P | nonpolar | neutral |
| Serine | Ser | S | polar | neutral |
| Threonine | Thr | T | polar | neutral |
| Tryptophan | Trp | W | nonpolar | neutral |
| Tyrosine | Tyr | Y | polar | neutral |
| Valine | Val | V | nonpolar | neutral |

Any intein can be used with the compositions and methods disclosed herein. For example, an intein can be used in the context of a CIPS.

Examples of inteins can be found in Perler, F. B. (2002) InBase, the Intein Database. Nucleic Acids Res. 30, 383-384, hereby incorporated by reference in its entirety for teaching examples of inteins that can be used with the compositions and methods disclosed herein. Additional examples of naturally occurring inteins include, but are not limited to, those found in Table 2. In one example, the intein can be Mtu-RecA. In some aspects, the inteins consist of two functionally and structurally distinct domains, a protein-splicing domain and an endonuclease domain.

TABLE 2

| Naturally Occurring Inteins | | |
| --- | --- | --- |
| Intein Name | Organism Name | Organism Description |
| Eucarya | | |
| APMV Pol | Acanthomoeba polyphaga Mimivirus | isolate = "Rowbotham-Bradford", Virus, infects Amoebae, taxon: 212035 |
| Abr PRP8 | Aspergillus brevipes FRR2439 | Fungi, ATCC 16899, taxon: 75551 |
| Aca-G186AR PRP8 | Ajellomyces capsulatus G186AR | Taxon: 447093, strain G186AR |
| Aca-H143 PRP8 | Ajellomyces capsulatus H143 | Taxon: 544712 |

TABLE 2-continued

Naturally Occurring Inteins

| Intein Name | Organism Name | Organism Description |
| --- | --- | --- |
| Aca-JER2004 PRP8 | *Ajellomyces capsulatus* (anamorph: *Histoplasma capsulatum*) | strain = JER2004, taxon: 5037, Fungi |
| Aca-NAm1 PRP8 | *Ajellomyces capsulatus* NAm1 | strain = "NAm1", taxon: 339724 |
| Ade-ER3 PRP8 | *Ajellomyces dermatitidis* ER-3 | Human fungal pathogen.taxon: 559297 |
| Ade-SLH14081 PRP8 | *Ajellomyces dermatitidis* SLH14081, | Human fungal pathogen |
| Afu-Af293 PRP8 | *Aspergillus fumigatus* var. *ellipticus*, strain Af293 | Human pathogenic fungus, taxon: 330879 |
| Afu-FRR0163 PRP8 | *Aspergillus fumigatus* strain FRR0163 | Human pathogenic fungus, taxon: 5085 |
| Afu-NRRL5109 PRP8 | *Aspergillus fumigatus* var. *ellipticus*, strain NRRL 5109 | Human pathogenic fungus, taxon: 41121 |
| Agi-NRRL6136 PRP8 | *Aspergillus giganteus* Strain NRRL 6136 | Fungus, taxon: 5060 |
| Ani-FGSCA4 PRP8 | *Aspergillus nidulans* FGSC A | Filamentous fungus, taxon: 227321 |
| Avi PRP8 | *Aspergillus viridinutans* strain FRR0577 | Fungi, ATCC 16902, taxon: 75553 |
| Bci PRP8 | *Botrytis cinerea* (teleomorph of *Botryotinia fuckeliana* B05.10) | Plant fungal pathogen |
| Bde-JEL197 RPB2 | *Batrachochytrium dendrobatidis* JEL197 | Chytrid fungus, isolate = "AFTOL-ID 21", taxon: 109871 |
| Bde-JEL423 PRP8-1 | *Batrachochytrium dendrobatidis* JEL423 | Chytrid fungus, isolate JEL423, taxon 403673 |
| Bde-JEL423 PRP8-2 | *Batrachochytrium dendrobatidis* JEL423 | Chytrid fungus, isolate JEL423, taxon 403673 |
| Bde-JEL423 RPC2 | *Batrachochytrium dendrobatidis* JEL423 | Chytrid fungus, isolate JEL423, taxon 403673 |
| Bde-JEL423 eIF-5B | *Batrachochytrium dendrobatidis* JEL423 | Chytrid fungus, isolate JEL423, taxon 403673 |
| Bfu-B05 PRP8 | *Botryotinia fuckeliana* B05.10 | Taxon: 332648 |
| CIV RIR1 | *Chilo* iridescent virus | dsDNA eucaryotic virus, taxon: 10488 |
| CV-NY2A ORF212392 | *Chlorella* virus NY2A infects *Chlorella* NC64A, which infects *Paramecium bursaria* | dsDNA eucaryotic virus, taxon: 46021, Family Phycodnaviridae |
| CV-NY2A RIR1 | *Chlorella* virus NY2A infects *Chlorella* NC64A, which infects *Paramecium bursaria* | dsDNA eucaryotic virus, taxon: 46021, Family Phycodnaviridae |
| CZIV RIR1 | *Costelytra zealandica* iridescent virus | dsDNA eucaryotic virus, Taxon: 68348 |
| Cba-WM02.98 PRP8 | *Cryptococcus bacillisporus* strain WM02.98 (aka *Cryptococcus neoformans gattii*) | Yeast, human pathogen, taxon: 37769 |
| Cba-WM728 PRP8 | *Cryptococcus bacillisporus* strain WM728 | Yeast, human pathogen, taxon: 37769 |
| Ceu ClpP | *Chlamydomonas eugametos* (chloroplast) | Green alga, taxon: 3053 |
| Cga PRP8 | *Cryptococcus gattii* (aka *Cryptococcus bacillisporus*) | Yeast, human pathogen |
| Cgl VMA | *Candida glabrata* | Yeast, taxon: 5478 |
| Cla PRP8 | *Cryptococcus laurentii* strain CBS139 | Fungi, Basidiomycete yeast, taxon: 5418 |
| Cmo ClpP | *Chlamydomonas moewusii*, strain UTEX 97 | Green alga, chloroplast gene, taxon: 3054 |
| Cmo RPB2 (RpoBb) | *Chlamydomonas moewusii*, strain UTEX 97 | Green alga, chloroplast gene, taxon: 3054 |
| Cne-A PRP8 (Fne-A PRP8) | *Filobasidiella neoformans* (*Cryptococcus neoformans*) Serotype A, PHLS_8104 | Yeast, human pathogen |
| Cne-AD PRP8 (Fne-AD PRP8) | *Cryptococcus neoformans* (*Filobasidiella neoformans*), Serotype AD, CBS132). | Yeast, human pathogen, ATCC32045, taxon: 5207 |
| Cne-JEC21 PRP8 | *Cryptococcus neoformans* var. *neoformans* JEC21 | Yeast, human pathogen, serotype = "D" taxon: 214684 |
| Cpa ThrRS | *Candida parapsilosis*, strain CLIB214 | Yeast, Fungus, taxon: 5480 |
| Cre RPB2 | *Chlamydomonas reinhardtii* (nucleus) | Green algae, taxon: 3055 |
| CroV Pol | *Cafeteria roenbergensis* virus BV-PW1 | taxon: 693272, Giant virus infecting marine heterotrophic nanoflagellate |
| CroV RIR1 | *Cafeteria roenbergensis* virus BV-PW1 | taxon: 693272, Giant virus infecting marine heterotrophic nanoflagellate |

TABLE 2-continued

Naturally Occurring Inteins

| Intein Name | Organism Name | Organism Description |
|---|---|---|
| CroV RPB2 | *Cafeteria roenbergensis* virus BV-PW1 | taxon: 693272, Giant virus infecting marine heterotrophic nanoflagellate |
| CroV Top2 | *Cafeteria roenbergensis* virus BV-PW1 | taxon: 693272, Giant virus infecting marine heterotrophic nanoflagellate |
| Cst RPB2 | *Coelomomyces stegomyiae* | Chytrid fungus, isolate = "AFTOL-ID 18", taxon: 143960 |
| Ctr ThrRS | *Candida tropicalis* ATCC750 | Yeast |
| Ctr VMA | *Candida tropicalis* (nucleus) | Yeast |
| Ctr-MYA3404 VMA | *Candida tropicalis* MYA-3404 | Taxon: 294747 |
| Ddi RPC2 | *Dictyostelium discoideum* strain AX4 (nucleus) | Mycetozoa (a social amoeba) |
| Dhan GLT1 | *Debaryomyces hansenii* CBS767 | Fungi, Anamorph: *Candida famata*, taxon: 4959 |
| Dhan VMA | *Debaryomyces hansenii* CBS767 | Fungi, taxon: 284592 |
| Eni PRP8 | *Emericella nidulans* R20 (anamorph: *Aspergillus nidulans*) | taxon: 162425 |
| Eni-FGSCA4 PRP8 | *Emericella nidulans* (anamorph: *Aspergillus nidulans*) FGSC A4 | Filamentous fungus, taxon: 162425 |
| Fte RPB2 (RpoB) | *Floydiella terrestris*, strain UTEX 1709 | Green alga, chloroplast gene, taxon: 51328 |
| Gth DnaB | *Guillardia theta* (plastid) | Cryptophyte Algae |
| HaV01 Pol | *Heterosigma akashiwo* virus 01 | Algal virus, taxon: 97195, strain HaV01 |
| Hca PRP8 | *Histoplasma capsulatum* (anamorph: *Ajellomyces capsulatus*) | Fungi, human pathogen |
| IIV6 RIR1 | Invertebrate iridescent virus 6 | dsDNA eucaryotic virus, taxon: 176652 |
| Kex-CBS379 VMA | *Kazachstania exigua*, formerly *Saccharomyces exiguus*, strain CBS379 | Yeast, taxon: 34358 |
| Kla-CBS683 VMA | *Kluyveromyces lactis*, strain CBS683 | Yeast, taxon: 28985 |
| Kla-IFO1267 VMA | *Kluyveromyces lactis* IFO1267 | Fungi, taxon: 28985 |
| Kla-NRRLY1140 VMA | *Kluyveromyces lactis* NRRL Y-1140 | Fungi, taxon: 284590 |
| Lel VMA | *Lodderomyces elongisporus* | Yeast |
| Mca-CBS113480 PRP8 | *Microsporum canis* CBS 113480 | Taxon: 554155 |
| Nau PRP8 | *Neosartorya aurata* NRRL 4378 | Fungus, taxon: 41051 |
| Nfe-NRRL5534 PRP8 | *Neosartorya fennelliae* NRRL 5534 | Fungus, taxon: 41048 |
| Nfi PRP8 | *Neosartorya fischeri* | Fungi |
| Ngl-FR2163 PRP8 | *Neosartorya glabra* FRR2163 | Fungi, ATCC 16909, taxon: 41049 |
| Ngl-FRR1833 PRP8 | *Neosartorya glabra* FRR1833 | Fungi, taxon: 41049, (preliminary identification) |
| Nqu PRP8 | *Neosartorya quadricincta*, strain NRRL 4175 | taxon: 41053 |
| Nspi PRP8 | *Neosartorya spinosa* FRR4595 | Fungi, taxon: 36631 |
| Pabr-Pb01 PRP8 | *Paracoccidioides brasiliensis* Pb01 | Taxon: 502779 |
| Pabr-Pb03 PRP8 | *Paracoccidioides brasiliensis* Pb03 | Taxon: 482561 |
| Pan CHS2 | *Podospora anserina* | Fungi, Taxon 5145 |
| Pan GLT1 | *Podospora anserina* | Fungi, Taxon 5145 |
| Pbl PRP8-a | *Phycomyces blakesleeanus* | Zygomycete fungus, strain NRRL155 |
| Pbl PRP8-b | *Phycomyces blakesleeanus* | Zygomycete fungus, strain NRRL155 |
| Pbr-Pb18 PRP8 | *Paracoccidioides brasiliensis* Pb18 | Fungi, taxon: 121759 |
| Pch PRP8 | *Penicillium chrysogenum* | Fungus, taxon: 5076 |
| Pex PRP8 | *Penicillium expansum* | Fungus, taxon27334 |
| Pgu GLT1 | *Pichia (Candida) guilliermondii* | Fungi, Taxon 294746 |
| Pgu-alt GLT1 | *Pichia (Candida) guilliermondii* | Fungi |
| Pno GLT1 | *Phaeosphaeria nodorum* SN15 | Fungi, taxon: 321614 |
| Pno RPA2 | *Phaeosphaeria nodorum* SN15 | Fungi, taxon: 321614 |
| Ppu DnaB | *Porphyra purpurea* (chloroplast) | Red Alga |
| Pst VMA | *Pichia stipitis* CBS 6054, taxon: 322104 | Yeast |
| Ptr PRP8 | *Pyrenophora tritici*-repentis Pt-1C-BF | Ascomycete fungus, taxon: 426418 |
| Pvu PRP8 | *Penicillium vulpinum* (formerly *P. claviforme*) | Fungus |
| Pye DnaB | *Porphyra yezoensis* chloroplast, cultivar U-51 | Red alga, organelle = "plastid:chloroplast", "taxon: 2788 |
| Sas RPB2 | *Spiromyces aspiralis* NRRL 22631 | Zygomycete fungus, isolate = "AFTOL-ID 185", taxon: 68401 |

TABLE 2-continued

Naturally Occurring Inteins

| Intein Name | Organism Name | Organism Description |
|---|---|---|
| Sca-CBS4309 VMA | *Saccharomyces castellii*, strain CBS4309 | Yeast, taxon: 27288 |
| Sca-IFO1992 VMA | *Saccharomyces castellii*, strain IFO1992 | Yeast, taxon: 27288 |
| Scar VMA | *Saccharomyces cariocanus*, strain = "UFRJ 50791 | Yeast, taxon: 114526 |
| Sce VMA | *Saccharomyces cerevisiae* (nucleus) | Yeast, also in Sce strains OUT7163, OUT7045, OUT7163, IFO1992 |
| Sce-DH1-1A VMA | *Saccharomyces cerevisiae* strain DH1-1A | Yeast, taxon: 173900, also in Sce strains OUT7900, OUT7903, OUT7112 |
| Sce-JAY291 VMA | *Saccharomyces cerevisiae* JAY291 | Taxon: 574961 |
| Sce-OUT7091 VMA | *Saccharomyces cerevisiae* OUT7091 | Yeast, taxon: 4932, also in Sce strains OUT7043, OUT7064 |
| Sce-OUT7112 VMA | *Saccharomyces cerevisiae* OUT7112 | Yeast, taxon: 4932, also in Sce strains OUT7900, OUT7903 |
| Sce-YJM789 VMA | *Saccharomyces cerevisiae* strain YJM789 | Yeast, taxon: 307796 |
| Sda VMA | *Saccharomyces dairenensis*, strain CBS 421 | Yeast, taxon: 27289, Also in Sda strain IFO0211 |
| Sex-IFO1128 VMA | *Saccharomyces exiguus*, strain = "IFO1128" | Yeast, taxon: 34358 |
| She RPB2 (RpoB) | *Stigeoclonium helveticum*, strain UTEX 441 | Green alga, chloroplast gene, taxon: 55999 |
| Sja VMA | *Schizosaccharomyces japonicus* yFS275 | Ascomycete fungus, taxon: 402676 |
| Spa VMA | *Saccharomyces pastorianus* IFO11023 | Yeast, taxon: 27292 |
| Spu PRP8 | *Spizellomyces punctatus* | Chytrid fungus, |
| Sun VMA | *Saccharomyces unisporus*, strain CBS 398 | Yeast, taxon: 27294 |
| Tgl VMA | *Torulaspora globosa*, strain CBS 764 | Yeast, taxon: 48254 |
| Tpr VMA | *Torulaspora pretoriensis*, strain CBS 5080 | Yeast, taxon: 35629 |
| Ure-1704 PRP8 | *Uncinocarpus reesii* | Filamentous fungus |
| Vpo VMA | *Vanderwaltozyma polyspora*, formerly *Kluyveromyces polysporus*, strain CBS 2163 | Yeast, taxon: 36033 |
| WIV RIR1 | *Wiseana* iridescent virus | dsDNA eucaryotic virus, taxon: 68347 |
| Zba VMA | *Zygosaccharomyces bailii*, strain CBS 685 | Yeast, taxon: 4954 |
| Zbi VMA | *Zygosaccharomyces bisporus*, strain CBS 702 | Yeast, taxon: 4957 |
| Zro VMA | *Zygosaccharomyces rouxii*, strain CBS 688 | Yeast, taxon: 4956 |
| Eubacteria | | |
| AP-APSE1 dpol | *Acyrthosiphon pisum* secondary endosymbiot phage 1 | Bacteriophage, taxon: 67571 |
| AP-APSE2 dpol | Bacteriophage APSE-2, isolate = T5A | Bacteriophage of Candidatus *Hamiltonella defensa*, endosymbiot of Acyrthosiphon pisum, taxon: 340054 |
| AP-APSE4 dpol | Bacteriophage of Candidatus *Hamiltonella defensa* strain 5ATac, endosymbiot of *Acyrthosiphon pisum* | Bacteriophage, taxon: 568990 |
| AP-APSE5 dpol | Bacteriophage APSE-5 | Bacteriophage of Candidatus *Hamiltonella defensa*, endosymbiot of *Uroleucon rudbeckiae*, taxon: 568991 |
| AP-Aaphi23 MupF | Bacteriophage Aaphi23, *Haemophilus phage* Aaphi23 | *Actinobacillus actinomycetemcomitans* Bacteriophage, taxon: 230158 |
| Aae RIR2 | *Aquifex aeolicus* strain VF5 | Thermophilic chemolithoautotroph, taxon: 63363 |
| Aave-AAC001 Aave1721 | *Acidovorax avenae* subsp. *citrulli* AAC00-1 | taxon: 397945 |
| Aave-AAC001 RIR1 | *Acidovorax avenae* subsp. *citrulli* AAC00-1 | taxon: 397945 |
| Aave-ATCC19860 RIR1 | *Acidovorax avenae* subsp. *avenae* ATCC 19860 | Taxon: 643561 |

TABLE 2-continued

Naturally Occurring Inteins

| Intein Name | Organism Name | Organism Description |
| --- | --- | --- |
| Aba Hyp-02185 | *Acinetobacter baumannii* ACICU | taxon: 405416 |
| Ace RIR1 | *Acidothermus cellulolyticus* 11B | taxon: 351607 |
| Aeh DnaB-1 | *Alkalilimnicola ehrlichei* MLHE-1 | taxon: 187272 |
| Aeh DnaB-2 | *Alkalilimnicola ehrlichei* MLHE-1 | taxon: 187272 |
| Aeh RIR1 | *Alkalilimnicola ehrlichei* MLHE-1 | taxon: 187272 |
| AgP-S1249 MupF | *Aggregatibacter phage* S1249 | Taxon: 683735 |
| Aha DnaE-c | *Aphanothece halophytica* | Cyanobacterium, taxon: 72020 |
| Aha DnaE-n | *Aphanothece halophytica* | Cyanobacterium, taxon: 72020 |
| Alvi-DSM180 GyrA | *Allochromatium vinosum* DSM 180 | Taxon: 572477 |
| Ama MADE823 | phage uncharacterized protein [*Alteromonas macleodii* 'Deep ecotype'] | Probably prophage gene, taxon: 314275 |
| Amax-CS328 DnaX | *Arthrospira maxima* CS-328 | Taxon: 513049 |
| Aov DnaE-c | *Aphanizomenon ovalisporum* | Cyanobacterium, taxon: 75695 |
| Aov DnaE-n | *Aphanizomenon ovalisporum* | Cyanobacterium, taxon: 75695 |
| Apl-C1 DnaX | *Arthrospira platensis* | Taxon: 118562, strain C1 |
| Arsp-FB24 DnaB | *Arthrobacter* species FB24 | taxon: 290399 |
| Asp DnaE-c | *Anabaena* species PCC7120, (*Nostoc* sp. PCC7120) | Cyanobacterium, Nitrogen-fixing, taxon: 103690 |
| Asp DnaE-n | *Anabaena* species PCC7120, (*Nostoc* sp. PCC7120) | Cyanobacterium, Nitrogen-fixing, taxon: 103690 |
| Ava DnaE-c | *Anabaena variabilis* ATCC29413 | Cyanobacterium, taxon: 240292 |
| Ava DnaE-n | *Anabaena variabilis* ATCC29413 | Cyanobacterium, taxon: 240292 |
| Avin RIR1 BIL | *Azotobacter vinelandii* | taxon: 354 |
| Bce-MCO3 DnaB | *Burkholderia cenocepacia* MC0-3 | taxon: 406425 |
| Bce-PC184 DnaB | *Burkholderia cenocepacia* PC184 | taxon: 350702 |
| Bse-MLS10 TerA | *Bacillus selenitireducens* MLS10 | Probably prophage gene, Taxon: 439292 |
| BsuP-M1918 RIR1 | *B. subtilis* M1918 (prophage) | Prophage in *B. subtilis* M1918. taxon: 157928 |
| BsuP-SPBc2 RIR1 | *B. subtilis* strain 168 Sp beta c2 prophage | *B. subtilis* taxon 1423. SPbeta c2 phage, taxon: 66797 |
| Bvi IcmO | *Burkholderia vietnamiensis* G4 | plasmid = "pBVIE03". taxon: 269482 |
| CP-P1201 Thy1 | *Corynebacterium* phage P1201 | lytic bacteriophage P1201 from *Corynebacterium glutamicum* NCHU 87078. Viruses; dsDNA viruses, taxon: 384848 |
| Cag RIR1 | *Chlorochromatium aggregatum* | Motile, phototrophic consortia |
| Cau SpoVR | *Chloroflexus aurantiacus* J-10-fl | Anoxygenic phototroph, taxon: 324602 |
| CbP-C-St RNR | *Clostridium botulinum* phage C-St | Phage, specific_host = "*Clostridium botulinum* type C strain C-Stockholm, taxon: 12336 |
| CbP-D1873 RNR | *Clostridium botulinum* phage D | Ssp. phage from *Clostridium botulinum* type D strain, 1873, taxon: 29342 |
| Cbu-Dugway DnaB | *Coxiella burnetii* Dugway 5J108-111 | Proteobacteria; Legionellales; taxon: 434922 |
| Cbu-Goat DnaB | *Coxiella burnetii* 'MSU Goat Q177' | Proteobacteria; Legionellales; taxon: 360116 |
| Cbu-RSA334 DnaB | *Coxiella burnetii* RSA 334 | Proteobacteria; Legionellales; taxon: 360117 |
| Cbu-RSA493 DnaB | *Coxiella burnetii* RSA 493 | Proteobacteria; Legionellales; taxon: 227377 |
| Cce Hyp1-Csp-2 | *Cyanothece* sp. ATCC 51142 | Marine unicellular diazotrophic cyanobacterium, taxon: 43989 |
| Cch RIR1 | *Chlorobium chlorochromatii* CaD3 | taxon: 340177 |
| Ccy Hyp1-Csp-1 | *Cyanothece* sp. CCY0110 | Cyanobacterium, taxon: 391612 |
| Ccy Hyp1-Csp-2 | *Cyanothece* sp. CCY0110 | Cyanobacterium, taxon: 391612 |
| Cfl-DSM20109 DnaB | *Cellulomonas flavigena* DSM 20109 | Taxon: 446466 |
| Chy RIR1 | *Carboxydothermus hydrogenoformans* Z-2901 | Thermophile, taxon = 246194 |
| Ckl PTerm | *Clostridium kluyveri* DSM 555 | plasmid = "pCKL555A", taxon: 431943 |
| Cra-CS505 DnaE-c | *Cylindrospermopsis raciborskii* CS-505 | Taxon: 533240 |
| Cra-CS505 DnaE-n | *Cylindrospermopsis raciborskii* CS-505 | Taxon: 533240 |

TABLE 2-continued

Naturally Occurring Inteins

| Intein Name | Organism Name | Organism Description |
|---|---|---|
| Cra-CS505 GyrB | *Cylindrospermopsis raciborskii* CS-505 | Taxon: 533240 |
| Csp-CCY0110 DnaE-c | *Cyanothece* sp. CCY0110 | Taxon: 391612 |
| Csp-CCY0110 DnaE-n | *Cyanothece* sp. CCY0110 | Taxon: 391612 |
| Csp-PCC7424 DnaE-c | *Cyanothece* sp. PCC 7424 | Cyanobacterium, taxon: 65393 |
| Csp-PCC7424 DnaE-n | *Cyanothece* sp. PCC7424 | Cyanobacterium, taxon: 65393 |
| Csp-PCC7425 DnaB | *Cyanothece* sp. PCC 7425 | Taxon: 395961 |
| Csp-PCC7822 DnaE-n | *Cyanothece* sp. PCC 7822 | Taxon: 497965 |
| Csp-PCC8801 DnaE-c | *Cyanothece* sp. PCC 8801 | Taxon: 41431 |
| Csp-PCC8801 DnaE-n | *Cyanothece* sp. PCC 8801 | Taxon: 41431 |
| Cth ATPase BIL | *Clostridium thermocellum* | ATCC27405, taxon: 203119 |
| Cth-ATCC27405 TerA | *Clostridium thermocellum* ATCC27405 | Probable prophage, ATCC27405, taxon: 203119 |
| Cth-DSM2360 TerA | *Clostridium thermocellum* DSM 2360 | Probably prophage gene, Taxon: 572545 |
| Cwa DnaB | *Crocosphaera watsonii* WH 8501 (*Synechocystis* sp. WH 8501) | taxon: 165597 |
| Cwa DnaE-c | *Crocosphaera watsonii* WH 8501 (*Synechocystis* sp. WH 8501) | Cyanobacterium, taxon: 165597 |
| Cwa DnaE-n | *Crocosphaera watsonii* WH 8501 (*Synechocystis* sp. WH 8501) | Cyanobacterium, taxon: 165597 |
| Cwa PEP | *Crocosphaera watsonii* WH 8501 (*Synechocystis* sp. WH 8501) | taxon: 165597 |
| Cwa RIR1 | *Crocosphaera watsonii* WH 8501 (*Synechocystis* sp. WH 8501) | taxon: 165597 |
| Daud RIR1 | *Candidatus Desulforudis audaxviator* MP104C | taxon: 477974 |
| Dge DnaB | *Deinococcus geothermalis* DSM11300 | Thermophilic, radiation resistant |
| Dha-DCB2 RIR1 | *Desulfitobacterium hafniense* DCB-2 | Anaerobic dehalogenating bacteria, taxon: 49338 |
| Dha-Y51 RIR1 | *Desulfitobacterium hafniense* Y51 | Anaerobic dehalogenating bacteria, taxon: 138119 |
| Dpr-MLMS1 RIR1 | delta proteobacterium MLMS-1 | Taxon: 262489 |
| Dra RIR1 | *Deinococcus radiodurans* R1, TIGR strain | Radiation resistant, taxon: 1299 |
| Dra Snf2-c | *Deinococcus radiodurans* R1, TIGR strain | Radiation and DNA damage resistent, taxon: 1299 |
| Dra Snf2-n | *Deinococcus radiodurans* R1, TIGR strain | Radiation and DNA damage resistent, taxon: 1299 |
| Dra-ATCC13939 Snf2 | *Deinococcus radiodurans* R1, ATCC13939/Brooks & Murray strain | Radiation and DNA damage resistent, taxon: 1299 |
| Dth UDP GD | *Dictyoglomus thermophilum* H-6-12 | strain = "H-6-12; ATCC 35947, taxon: 309799 |
| Dvul ParB | *Desulfovibrio vulgaris* subsp. *vulgaris* DP4 | taxon: 391774 |
| EP-Min27 Primase | Enterobacteria phage Min27 | bacteriophage of host = "*Eschericia coli* O157:H7 str. Min27" |
| Fal DnaB | *Frankia alni* ACN14a | Plant symbiot, taxon: 326424 |
| Fsp-CcI3 RIR1 | *Frankia* species CcI3 | taxon: 106370 |
| Gob DnaE | *Gemmata obscuriglobus* UQM2246 | Taxon 114, TIGR genome strain, budding bacteria |
| Gob Hyp | *Gemmata obscuriglobus* UQM2246 | Taxon 114, TIGR genome strain, budding bacteria |
| Gvi DnaB | *Gloeobacter violaceus*, PCC 7421 | taxon: 33072 |
| Gvi RIR1-1 | *Gloeobacter violaceus*, PCC 7421 | taxon: 33072 |
| Gvi RIR1-2 | *Gloeobacter violaceus*, PCC 7421 | taxon: 33072 |
| Hhal DnaB | *Halorhodospira halophila* SL1 | taxon: 349124 |
| Kfl-DSM17836 DnaB | *Kribbella flavida* DSM 17836 | Taxon: 479435 |
| Kra DnaB | *Kineococcus radiotolerans* SRS30216 | Radiation resistant |
| LLP-KSY1 PolA | *Lactococcus* phage KSY1 | Bacteriophage, taxon: 388452 |
| LP-phiHSIC Helicase | *Listonella pelagia* phage phiHSIC | taxon: 310539, a pseudotemperate marine phage of *Listonella pelagia* |
| Lsp-PCC8106 GyrB | *Lyngbya* sp. PCC 8106 | Taxon: 313612 |
| MP-Be DnaB | Mycobacteriophage Bethlehem | Bacteriophage, taxon: 260121 |
| MP-Be gp51 | Mycobacteriophage Bethlehem | Bacteriophage, taxon: 260121 |
| MP-Catera gp206 | Mycobacteriophage Catera | Mycobacteriophage, taxon: 373404 |
| MP-KBG gp53 | *Mycobacterium* phage KBG | Taxon: 540066 |
| MP-Mcjw1 DnaB | Mycobacteriophage CJW1 | Bacteriophage, taxon: 205869 |
| MP-Omega DnaB | Mycobacteriophage Omega | Bacteriophage, taxon: 205879 |
| MP-U2 gp50 | Mycobacteriophage U2 | Bacteriophage, taxon: 260120 |

TABLE 2-continued

Naturally Occurring Inteins

| Intein Name | Organism Name | Organism Description |
|---|---|---|
| Maer-NIES843 DnaB | *Microcystis aeruginosa* NIES-843 | Bloom-forming toxic cyanobacterium, taxon: 449447 |
| Maer-NIES843 DnaE-c | *Microcystis aeruginosa* NIES-843 | Bloom-forming toxic cyanobacterium, taxon: 449447 |
| Maer-NIES843 DnaE-n | *Microcystis aeruginosa* NIES-843 | Bloom-forming toxic cyanobacterium, taxon: 449447 |
| Mau-ATCC27029 GyrA | *Micromonospora aurantiaca* ATCC 27029 | Taxon: 644283 |
| Mav-104 DnaB | *Mycobacterium avium* 104 | taxon: 243243 |
| Mav-ATCC25291 DnaB | *Mycobacterium avium* subsp. *avium* ATCC 25291 | Taxon: 553481 |
| Mav-ATCC35712 DnaB | *Mycobacterium avium* | ATCC35712, taxon 1764 |
| Mav-PT DnaB | *Mycobacterium avium* subsp. *paratuberculosis* str. k10 | taxon: 262316 |
| Mbo Pps1 | *Mycobacterium bovis* subsp. *bovis* AF2122/97 | strain = "AF2122/97", taxon: 233413 |
| Mbo RecA | *Mycobacterium bovis* subsp. *bovis* AF2122/97 | taxon: 233413 |
| Mbo SufB (Mbo Pps1) | *Mycobacterium bovis* subsp. *bovis* AF2122/97 | taxon: 233413 |
| Mbo-1173P DnaB | *Mycobacterium bovis* BCG Pasteur 1173P | strain = BCG Pasteur 1173P2,, taxon: 410289 |
| Mbo-AF2122 DnaB | *Mycobacterium bovis* subsp. *bovis* AF2122/97 | strain = "AF2122/97", taxon: 233413 |
| Mca MupF | *Methylococcus capsulatus* Bath, prophage MuMc02 | prophage MuMc02, taxon: 243233 |
| Mca RIR1 | *Methylococcus capsulatus* Bath | taxon: 243233 |
| Mch RecA | *Mycobacterium chitae* | IP14116003, taxon: 1792 |
| Mcht-PCC7420 DnaE-1 | *Microcoleus chthonoplastes* PCC7420 | Cyanobacterium, taxon: 118168 |
| Mcht-PCC7420 DnaE-2c | *Microcoleus chthonoplastes* PCC7420 | Cyanobacterium, taxon: 118168 |
| Mcht-PCC7420 DnaE-2n | *Microcoleus chthonoplastes* PCC7420 | Cyanobacterium, taxon: 118168 |
| Mcht-PCC7420 GyrB | *Microcoleus chthonoplastes* PCC 7420 | Taxon: 118168 |
| Mcht-PCC7420 RIR1-1 | *Microcoleus chthonoplastes* PCC 7420 | Taxon: 118168 |
| Mcht-PCC7420 RIR1-2 | *Microcoleus chthonoplastes* PCC 7420 | Taxon: 118168 |
| Mex Helicase | *Methylobacterium extorquens* AM1 | *Alphaproteobacteria* |
| Mex TrbC | *Methylobacterium extorquens* AM1 | *Alphaproteobacteria* |
| Mfa RecA | *Mycobacterium fallax* | CITP8139, taxon: 1793 |
| Mfl GyrA | *Mycobacterium flavescens* Fla0 | taxon: 1776, reference #930991 |
| Mfl RecA | *Mycobacterium flavescens* Fla0 | strain = Fla0, taxon: 1776, ref. #930991 |
| Mfl-ATCC14474 RecA | *Mycobacterium flavescens*, ATCC14474 | strain = ATCC14474, taxon: 1776, ref #930991 |
| Mfl-PYR-GCK DnaB | *Mycobacterium flavescens* PYR-GCK | taxon: 350054 |
| Mga GyrA | *Mycobacterium gastri* | HP4389, taxon: 1777 |
| Mga RecA | *Mycobacterium gastri* | HP4389, taxon: 1777 |
| Mga SufB (Mga Pps1) | *Mycobacterium gastri* | HP4389, taxon: 1777 |
| Mgi-PYR-GCK DnaB | *Mycobacterium gilvum* PYR-GCK | taxon: 350054 |
| Mgi-PYR-GCK GyrA | *Mycobacterium gilvum* PYR-GCK | taxon: 350054 |
| Mgo GyrA | *Mycobacterium gordonae* | taxon: 1778, reference number 930835 |
| Min-1442 DnaB | *Mycobacterium intracellulare* | strain 1442, taxon: 1767 |
| Min-ATCC13950 GyrA | *Mycobacterium intracellulare* ATCC 13950 | Taxon: 487521 |
| Mkas GyrA | *Mycobacterium kansasii* | taxon: 1768 |
| Mkas-ATCC12478 GyrA | *Mycobacterium kansasii* ATCC 12478 | Taxon: 557599 |
| Mle-Br4923 GyrA | *Mycobacterium leprae* Br4923 | Taxon: 561304 |
| Mle-TN DnaB | *Mycobacterium leprae*, strain TN | Human pathogen, taxon: 1769 |
| Mle-TN GyrA | *Mycobacterium leprae* TN | Human pathogen, STRAIN = TN, taxon: 1769 |
| Mle-TN RecA | *Mycobacterium leprae*, strain TN | Human pathogen, taxon: 1769 |
| Mle-TN SufB (Mle Pps1) | *Mycobacterium leprae* | Human pathogen, taxon: 1769 |
| Mma GyrA | *Mycobacterium malmoense* | taxon: 1780 |
| Mmag Magn8951 BIL | *Magnetospirillum magnetotacticum* MS-1 | Gram negative, taxon: 272627 |

TABLE 2-continued

Naturally Occurring Inteins

| Intein Name | Organism Name | Organism Description |
|---|---|---|
| Msh RecA | *Mycobacterium shimodei* | ATCC27962, taxon: 29313 |
| Msm DnaB-1 | *Mycobacterium smegmatis* MC2 155 | MC2 155, taxon: 246196 |
| Msm DnaB-2 | *Mycobacterium smegmatis* MC2 155 | MC2 155, taxon: 246196 |
| Msp-KMS DnaB | *Mycobacterium* species KMS | taxon: 189918 |
| Msp-KMS GyrA | *Mycobacterium* species KMS | taxon: 189918 |
| Msp-MCS DnaB | *Mycobacterium* species MCS | taxon: 164756 |
| Msp-MCS GyrA | *Mycobacterium* species MCS | taxon: 164756 |
| Mthe RecA | *Mycobacterium thermoresistibile* | ATCC19527, taxon: 1797 |
| Mtu SufB (Mtu Pps1) | *Mycobacterium tuberculosis* strains H37Rv & CDC1551 | Human pathogen, taxon: 83332 |
| Mtu-C RecA | *Mycobacterium tuberculosis* C | Taxon: 348776 |
| Mtu-CDC1551 DnaB | *Mycobacterium tuberculosis*, CDC1551 | Human pathogen, taxon: 83332 |
| Mtu-CPHL RecA | *Mycobacterium tuberculosis* CPHL_A | Taxon: 611303 |
| Mtu-Canetti RecA | *Mycobacterium tuberculosis* /strain = "*Canetti*" | Taxon: 1773 |
| Mtu-EAS054 RecA | *Mycobacterium tuberculosis* EAS054 | Taxon: 520140 |
| Mtu-F11 DnaB | *Mycobacterium tuberculosis*, strain F11 | taxon: 336982 |
| Mtu-H37Ra DnaB | *Mycobacterium tuberculosis* H37Ra | ATCC 25177, taxon: 419947 |
| Mtu-H37Rv DnaB | *Mycobacterium tuberculosis* H37Rv | Human pathogen, taxon: 83332 |
| Mtu-H37Rv RecA | *Mycobacterium tuberculosis* H37Rv, Also CDC1551 | Human pathogen, taxon: 83332 |
| Mtu-Haarlem DnaB | *Mycobacterium tuberculosis* str. Haarlem | Taxon: 395095 |
| Mtu-K85 RecA | *Mycobacterium tuberculosis* K85 | Taxon: 611304 |
| Mtu-R604 RecA-n | *Mycobacterium tuberculosis* '98-R604 INH-RIF-EM' | Taxon: 555461 |
| Mtu-So93 RecA | *Mycobacterium tuberculosis* So93/sub_species = "*Canetti*" | Human pathogen, taxon: 1773 |
| Mtu-T17 RecA-c | *Mycobacterium tuberculosis* T17 | Taxon: 537210 |
| Mtu-T17 RecA-n | *Mycobacterium tuberculosis* T17 | Taxon: 537210 |
| Mtu-T46 RecA | *Mycobacterium tuberculosis* T46 | Taxon: 611302 |
| Mtu-T85 RecA | *Mycobacterium tuberculosis* T85 | Taxon: 520141 |
| Mtu-T92 RecA | *Mycobacterium tuberculosis* T92 | Taxon: 515617 |
| Mvan DnaB | *Mycobacterium vanbaalenii* PYR-1 | taxon: 350058 |
| Mvan GyrA | *Mycobacterium vanbaalenii* PYR-1 | taxon: 350058 |
| Mxa RAD25 | *Myxococcus xanthus* DK1622 | Deltaproteobacteria |
| Mxe GyrA | *Mycobacterium xenopi* strain IMM5024 | taxon: 1789 |
| Naz-0708 RIR1-1 | *Nostoc azollae* 0708 | Taxon: 551115 |
| Naz-0708 RIR1-2 | *Nostoc azollae* 0708 | Taxon: 551115 |
| Nfa DnaB | *Nocardia farcinica* IFM 10152 | taxon: 247156 |
| Nfa Nfa15250 | *Nocardia farcinica* IFM 10152 | taxon: 247156 |
| Nfa RIR1 | *Nocardia farcinica* IFM 10152 | taxon: 247156 |
| Nosp-CCY9414 DnaE-n | *Nodularia spumigena* CCY9414 | Taxon: 313624 |
| Npu DnaB | *Nostoc punctiforme* | Cyanobacterium, taxon: 63737 |
| Npu GyrB | *Nostoc punctiforme* | Cyanobacterium, taxon: 63737 |
| Npu-PCC73102 DnaE-c | *Nostoc punctiforme* PCC73102 | Cyanobacterium, taxon: 63737, ATCC29133 |
| Npu-PCC73102 DnaE-n | *Nostoc punctiforme* PCC73102 | Cyanobacterium, taxon: 63737, ATCC29133 |
| Nsp-JS614 DnaB | *Nocardioides* species JS614 | taxon: 196162 |
| Nsp-JS614 TOPRIM | *Nocardioides* species JS614 | taxon: 196162 |
| Nsp-PCC7120 DnaB | *Nostoc* species PCC7120, (*Anabaena* sp. PCC7120) | Cyanobacterium, Nitrogen-fixing, taxon: 103690 |
| Nsp-PCC7120 DnaE-c | *Nostoc* species PCC7120, (*Anabaena* sp. PCC7120) | Cyanobacterium, Nitrogen-fixing, taxon: 103690 |
| Nsp-PCC7120 DnaE-n | *Nostoc* species PCC7120, (*Anabaena* sp. PCC7120) | Cyanobacterium, Nitrogen-fixing, taxon: 103690 |
| Nsp-PCC7120 RIR1 | *Nostoc* species PCC7120, (*Anabaena* sp. PCC7120) | Cyanobacterium, Nitrogen-fixing, taxon: 103690 |
| Oli DnaE-c | *Oscillatoria limnetica* str. 'Solar Lake' | Cyanobacterium, taxon: 262926 |
| Oli DnaE-n | *Oscillatoria limnetica* str. 'Solar Lake' | Cyanobacterium, taxon: 262926 |
| PP-PhiEL Helicase | *Pseudomonas aeruginosa* phage phiEL | Phage infects *Pseudomonas aeruginosa*, taxon: 273133 |
| PP-PhiEL ORF11 | *Pseudomonas aeruginosa* phage phiEL | phage infects *Pseudomonas aeruginosa*, taxon: 273133 |
| PP-PhiEL ORF39 | *Pseudomonas aeruginosa* phage phiEL | Phage infects *Pseudomonas aeruginosa*, taxon: 273133 |
| PP-PhiEL ORF40 | *Pseudomonas aeruginosa* phage phiEL | phage infects *Pseudomonas aeruginosa*, taxon: 273133 |

TABLE 2-continued

Naturally Occurring Inteins

| Intein Name | Organism Name | Organism Description |
|---|---|---|
| Pfl Fha BIL | *Pseudomonas fluorescens* Pf-5 | Plant commensal organism, taxon: 220664 |
| Plut RIR1 | *Pelodictyon luteolum* DSM 273 | Green sulfur bacteria, Taxon 319225 |
| Pma-EXH1 GyrA | *Persephonella marina* EX-H1 | Taxon: 123214 |
| Pma-ExH1 DnaE | *Persephonella marina* EX-H1 | Taxon: 123214 |
| Pna RIR1 | *Polaromonas naphthalenivorans* CJ2 | taxon: 365044 |
| Pnuc DnaB | *Polynucleobacter* sp. QLW-P1DMWA-1 | taxon: 312153 |
| Posp-JS666 DnaB | *Polaromonas* species JS666 | taxon: 296591 |
| Posp-JS666 RIR1 | *Polaromonas* species JS666 | taxon: 296591 |
| Pssp-A1-1 Fha | *Pseudomonas* species A1-1 | |
| Psy Fha | *Pseudomonas syringae* pv. tomato str. DC3000 | Plant (tomato) pathogen, taxon: 223283 |
| Rbr-D9 GyrB | *Raphidiopsis brookii* D9 | Taxon: 533247 |
| Rce RIR1 | *Rhodospirillum centenum* SW | taxon: 414684, ATCC 51521 |
| Rer-SK121 DnaB | *Rhodococcus erythropolis* SK121 | Taxon: 596309 |
| Rma DnaB | *Rhodothermus marinus* | Thermophile, taxon: 29549 |
| Rma-DSM4252 DnaB | *Rhodothermus marinus* DSM 4252 | Taxon: 518766 |
| Rma-DSM4252 DnaE | *Rhodothermus marinus* DSM 4252 | Thermophile, taxon: 518766 |
| Rsp RIR1 | *Roseovarius* species 217 | taxon: 314264 |
| SaP-SETP12 dpol | *Salmonella* phage SETP12 | Phage, taxon: 424946 |
| SaP-SETP3 Helicase | *Salmonella* phage SETP3 | Phage, taxon: 424944 |
| SaP-SETP3 dpol | *Salmonella* phage SETP3 | Phage, taxon: 424944 |
| SaP-SETP5 dpol | *Salmonella* phage SETP5 | Phage, taxon: 424945 |
| Sare DnaB | *Salinispora arenicola* CNS-205 | taxon: 391037 |
| Say RecG Helicase | *Streptomyces avermitilis* MA-4680 | taxon: 227882, ATCC 31267 |
| Sel-PC6301 RIR1 | *Synechococcus elongatus* PCC 6301 | taxon: 269084 Berkely strain 6301~equivalent name: Ssp PCC 6301~synonym: *Anacystis nudulans* |
| Sel-PC7942 DnaE-c | *Synechococcus elongatus* PC7942 | taxon: 1140 |
| Sel-PC7942 DnaE-n | *Synechococcus elongatus* PC7942 | taxon: 1140 |
| Sel-PC7942 RIR1 | *Synechococcus elongatus* PC7942 | taxon: 1140 |
| Sel-PCC6301 DnaE-c | *Synechococcus elongatus* PCC 6301 and PCC7942 | Cyanobacterium, taxon: 269084, "Berkely strain 6301~equivalent name: *Synechococcus* sp. PCC 6301~synonym: *Anacystis nudulans*" |
| Sel-PCC6301 DnaE-n | *Synechococcus elongatus* PCC 6301 | Cyanobacterium, taxon: 269084"Berkely strain 6301~equivalent name: *Synechococcus* sp. PCC 6301~synonym: *Anacystis nudulans*" |
| Sep RIR1 | *Staphylococcus epidermidis* RP62A | taxon: 176279 |
| ShP-Sfv-2a-2457T-n Primase | *Shigella flexneri* 2a str. 2457T | Putative bacteriphage |
| ShP-Sfv-2a-301-n Primase | *Shigella flexneri* 2a str. 301 | Putative bacteriphage |
| ShP-Sfv-5 Primase | *Shigella flexneri* 5 str. 8401 | Bacteriophage, isolation_source_epidemic, taxon: 373384 |
| SoP-SO1 dpol | *Sodalis* phage SO-1 | Phage/isolation_source = "*Sodalis glossinidius* strain GA-SG, secondary symbiont of *Glossina austeni* (Newstead)" |
| Spl DnaX | *Spirulina platensis*, strain C1 | Cyanobacterium, taxon: 1156 |
| Sru DnaB | *Salinibacter ruber* DSM 13855 | taxon: 309807, strain = "DSM 13855; M31" |
| Sru PolBc | *Salinibacter ruber* DSM 13855 | taxon: 309807, strain = "DSM 13855; M31" |
| Sru RIR1 | *Salinibacter ruber* DSM 13855 | taxon: 309807, strain = "DSM 13855; M31" |
| Ssp DnaB | *Synechocystis* species, strain PCC6803 | Cyanobacterium, taxon: 1148 |
| Ssp DnaE-c | *Synechocystis* species, strain PCC6803 | Cyanobacterium, taxon: 1148 |
| Ssp DnaE-n | *Synechocystis* species, strain PCC6803 | Cyanobacterium, taxon: 1148 |
| Ssp DnaX | *Synechocystis* species, strain PCC6803 | Cyanobacterium, taxon: 1148 |
| Ssp GyrB | *Synechocystis* species, strain PCC6803 | Cyanobacterium, taxon: 1148 |
| Ssp-JA2 DnaB | *Synechococcus* species JA-2-3B'a(2-13) | Cyanobacterium, Taxon: 321332 |

TABLE 2-continued

Naturally Occurring Inteins

| Intein Name | Organism Name | Organism Description |
|---|---|---|
| Ssp-JA2 RIR1 | *Synechococcus* species JA-2-3B'a(2-13) | Cyanobacterium, Taxon: 321332 |
| Ssp-JA3 DnaB | *Synechococcus* species JA-3-3Ab | Cyanobacterium, Taxon: 321327 |
| Ssp-JA3 RIR1 | *Synechococcus* species JA-3-3Ab | Cyanobacterium, Taxon: 321327 |
| Ssp-PCC7002 DnaE-c | *Synechocystis* species, strain PCC 7002 | Cyanobacterium, taxon: 32049 |
| Ssp-PCC7002 DnaE-n | *Synechocystis* species, strain PCC 7002 | Cyanobacterium, taxon: 32049 |
| Ssp-PCC7335 RIR1 | *Synechococcus* sp. PCC 7335 | Taxon: 91464 |
| StP-Twort ORF6 | *Staphylococcus* phage Twort | Phage, taxon 55510 |
| Susp-NBC371 DnaB intein | *Sulfurovum* sp. NBC37-1 | taxon: 387093 |
| Taq-Y51MC23 DnaE | *Thermus aquaticus* Y51MC23 | Taxon: 498848 |
| Taq-Y51MC23 RIR1 | *Thermus aquaticus* Y51MC23 | Taxon: 498848 |
| Tcu-DSM43183 RecA | *Thermomonospora curvata* DSM 43183 | Taxon: 471852 |
| Tel DnaE-c | *Thermosynechococcus elongatus* BP-1 | Cyanobacterium, taxon: 197221 |
| Tel DnaE-n | *Thermosynechococcus elongatus* BP-1 | Cyanobacterium, |
| Ter DnaB-1 | *Trichodesmium erythraeum* IMS101 | Cyanobacterium, taxon: 203124 |
| Ter DnaB-2 | *Trichodesmium erythraeum* IMS101 | Cyanobacterium, taxon: 203124 |
| Ter DnaE-1 | *Trichodesmium erythraeum* IMS101 | Cyanobacterium, taxon: 203124 |
| Ter DnaE-2 | *Trichodesmium erythraeum* IMS101 | Cyanobacterium, taxon: 203124 |
| Ter DnaE-3c | *Trichodesmium erythraeum* IMS101 | Cyanobacterium, taxon: 203124 |
| Ter DnaE-3n | *Trichodesmium erythraeum* IMS101 | Cyanobacterium, taxon: 203124 |
| Ter GyrB | *Trichodesmium erythraeum* IMS101 | Cyanobacterium, taxon: 203124 |
| Ter Ndse-1 | *Trichodesmium erythraeum* IMS101 | Cyanobacterium, taxon: 203124 |
| Ter Ndse-2 | *Trichodesmium erythraeum* IMS101 | Cyanobacterium, taxon: 203124 |
| Ter RIR1-1 | *Trichodesmium erythraeum* IMS101 | Cyanobacterium, taxon: 203124 |
| Ter RIR1-2 | *Trichodesmium erythraeum* IMS101 | Cyanobacterium, taxon: 203124 |
| Ter RIR1-3 | *Trichodesmium erythraeum* IMS101 | Cyanobacterium, taxon: 203124 |
| Ter RIR1-4 | *Trichodesmium erythraeum* IMS101 | Cyanobacterium, taxon: 203124 |
| Ter Snf2 | *Trichodesmium erythraeum* IMS101 | Cyanobacterium, taxon: 203124 |
| Ter ThyX | *Trichodesmium erythraeum* IMS101 | Cyanobacterium, taxon: 203124 |
| Tfus RecA-1 | *Thermobifida fusca* YX | Thermophile, taxon: 269800 |
| Tfus RecA-2 | *Thermobifida fusca* YX | Thermophile, taxon: 269800 |
| Tfus Tfu2914 | *Thermobifida fusca* YX | Thermophile, taxon: 269800 |
| Thsp-K90 RIR1 | *Thioalkalivibrio* sp. K90mix | Taxon: 396595 |
| Tth-DSM571 RIR1 | *Thermoanaerobacterium thermosaccharolyticum* DSM 571 | Taxon: 580327 |
| Tth-HB27 DnaE-1 | *Thermus thermophilus* HB27 | thermophile, taxon: 262724 |
| Tth-HB27 DnaE-2 | *Thermus thermophilus* HB27 | thermophile, taxon: 262724 |
| Tth-HB27 RIR1-1 | *Thermus thermophilus* HB27 | thermophile, taxon: 262724 |
| Tth-HB27 RIR1-2 | *Thermus thermophilus* HB27 | thermophile, taxon: 262724 |
| Tth-HB8 DnaE-1 | *Thermus thermophilus* HB8 | thermophile, taxon: 300852 |
| Tth-HB8 DnaE-2 | *Thermus thermophilus* HB8 | thermophile, taxon: 300852 |
| Tth-HB8 RIR1-1 | *Thermus thermophilus* HB8 | thermophile, taxon: 300852 |
| Tth-HB8 RIR1-2 | *Thermus thermophilus* HB8 | thermophile, taxon: 300852 |
| Tvu DnaE-c | *Thermosynechococcus vulcanus* | Cyanobacterium, taxon: 32053 |
| Tvu DnaE-n | *Thermosynechococcus vulcanus* | Cyanobacterium, taxon: 32053 |
| Tye RNR-1 | *Thermodesulfovibrio yellowstonii* DSM 11347 | taxon: 289376 |
| Tye RNR-2 | *Thermodesulfovibrio yellowstonii* DSM 11347 | taxon: 289376 |

Archaea

| | | |
|---|---|---|
| Ape APE0745 | *Aeropyrum pernix* K1 | Thermophile, taxon: 56636 |
| Cme-boo Pol-II | *Candidatus Methanoregula boonei* 6A8 | taxon: 456442 |

TABLE 2-continued

Naturally Occurring Inteins

| Intein Name | Organism Name | Organism Description |
|---|---|---|
| Fac-Fer1 RIR1 | *Ferroplasma acidarmanus*, taxon: 97393 and taxon 261390 | strain Fer1, eats iron |
| Fac-Fer1 SufB (Fac Pps1) | *Ferroplasma acidarmanus* | strain fer1, eats iron, taxon: 97393 |
| Fac-Type1 RIR1 | *Ferroplasma acidarmanus* type I, | Eats iron, taxon 261390 |
| Fac-typeI SufB (Fac Pps1) | *Ferroplasma acidarmanus* | Eats iron, taxon: 261390 |
| Hma CDC21 | *Haloarcula marismortui* ATCC 43049 | taxon: 272569, |
| Hma Pol-II | *Haloarcula marismortui* ATCC 43049 | taxon: 272569, |
| Hma PolB | *Haloarcula marismortui* ATCC 43049 | taxon: 272569, |
| Hma TopA | *Haloarcula marismortui* ATCC 43049 | taxon: 272569 |
| Hmu-DSM12286 MCM | *Halomicrobium mukohataei* DSM 12286 | taxon: 485914 (Halobacteria) |
| Hmu-DSM12286 PolB | *Halomicrobium mukohataei* DSM 12286 | Taxon: 485914 |
| Hsa-R1 MCM | *Halobacterium salinarum* R-1 | Halophile, taxon: 478009, strain = "R1; DSM 671" |
| Hsp-NRC1 CDC21 | *Halobacterium* species NRC-1 | Halophile, taxon: 64091 |
| Hsp-NRC1 Pol-II | *Halobacterium salinarum* NRC-1 | Halophile, taxon: 64091 |
| Hut MCM-2 | *Halorhabdus utahensis* DSM 12940 | taxon: 519442 |
| Hut-DSM12940 MCM-1 | *Halorhabdus utahensis* DSM 12940 | taxon: 519442 |
| Hvo PolB | *Haloferax volcanii* DS70 | taxon: 2246 |
| Hwa GyrB | *Haloquadratum walsbyi* DSM 16790 | Halophile, taxon: 362976, strain: DSM 16790 = HBSQ001 |
| Hwa MCM-1 | *Haloquadratum walsbyi* DSM 16790 | Halophile, taxon: 362976, strain: DSM 16790 = HBSQ001 |
| Hwa MCM-2 | *Haloquadratum walsbyi* DSM 16790 | Halophile, taxon: 362976, strain: DSM 16790 = HBSQ001 |
| Hwa MCM-3 | *Haloquadratum walsbyi* DSM 16790 | Halophile, taxon: 362976, strain: DSM 16790 = HBSQ001 |
| Hwa MCM-4 | *Haloquadratum walsbyi* DSM 16790 | Halophile, taxon: 362976, strain: DSM 16790 = HBSQ001 |
| Hwa Pol-II-1 | *Haloquadratum walsbyi* DSM 16790 | Halophile, taxon: 362976, strain: DSM 16790 = HBSQ001 |
| Hwa Pol-II-2 | *Haloquadratum walsbyi* DSM 16790 | Halophile, taxon: 362976, strain: DSM 16790 = HBSQ001 |
| Hwa PolB-1 | *Haloquadratum walsbyi* DSM 16790 | Halophile, taxon: 362976, strain: DSM 16790 = HBSQ001 |
| Hwa PolB-2 | *Haloquadratum walsbyi* DSM 16790 | Halophile, taxon: 362976, strain: DSM 16790 = HBSQ001 |
| Hwa PolB-3 | *Haloquadratum walsbyi* DSM 16790 | Halophile, taxon: 362976, strain: DSM 16790 = HBSQ001 |
| Hwa RCF | *Haloquadratum walsbyi* DSM 16790 | Halophile, taxon: 362976, strain: DSM 16790 = HBSQ001 |
| Hwa RIR1-1 | *Haloquadratum walsbyi* DSM 16790 | Halophile, taxon: 362976, strain: DSM 16790 = HBSQ001 |
| Hwa RIR1-2 | *Haloquadratum walsbyi* DSM 16790 | Halophile, taxon: 362976, strain: DSM 16790 = HBSQ001 |
| Hwa Top6B | *Haloquadratum walsbyi* DSM 16790 | Halophile, taxon: 362976, strain: DSM 16790 = HBSQ001 |
| Hwa rPol A" | *Haloquadratum walsbyi* DSM 16790 | Halophile, taxon: 362976, strain: DSM 16790 = HBSQ001 |
| Maeo Pol-II | *Methanococcus aeolicus* Nankai-3 | taxon: 419665 |
| Maeo RFC | *Methanococcus aeolicus* Nankai-3 | taxon: 419665 |
| Maeo RNR | *Methanococcus aeolicus* Nankai-3 | taxon: 419665 |
| Maeo-N3 Helicase | *Methanococcus aeolicus* Nankai-3 | taxon: 419665 |

TABLE 2-continued

Naturally Occurring Inteins

| Intein Name | Organism Name | Organism Description |
|---|---|---|
| Maeo-N3 RtcB | *Methanococcus aeolicus* Nankai-3 | taxon: 419665 |
| Maeo-N3 UDP GD | *Methanococcus aeolicus* Nankai-3 | taxon: 419665 |
| Mein-ME PEP | *Methanocaldococcus infernus* ME | thermophile, Taxon: 573063 |
| Mein-ME RFC | *Methanocaldococcus infernus* ME | Taxon: 573063 |
| Memar MCM2 | *Methanoculleus marisnigri* JR1 | taxon: 368407 |
| Memar Pol-II | *Methanoculleus marisnigri* JR1 | taxon: 368407 |
| Mesp-FS406 PolB-1 | *Methanocaldococcus* sp. FS406-22 | Taxon: 644281 |
| Mesp-FS406 PolB-2 | *Methanocaldococcus* sp. FS406-22 | Taxon: 644281 |
| Mesp-FS406 PolB-3 | *Methanocaldococcus* sp. FS406-22 | Taxon: 644281 |
| Mesp-FS406-22 LHR | *Methanocaldococcus* sp. FS406-22 | Taxon: 644281 |
| Mfe-AG86 Pol-1 | *Methanocaldococcus fervens* AG86 | Taxon: 573064 |
| Mfe-AG86 Pol-2 | *Methanocaldococcus fervens* AG86 | Taxon: 573064 |
| Mhu Pol-II | *Methanospirillum hungateii* JF-1 | taxon 323259 |
| Mja GF-6P | *Methanococcus jannaschii* (*Methanocaldococcus jannaschii* DSM 2661) | Thermophile, DSM 2661, taxon: 2190 |
| Mja Helicase | *Methanococcus jannaschii* (*Methanocaldococcus jannaschii* DSM 2661) | Thermophile, DSM 2661, taxon: 2190 |
| Mja Hyp-1 | *Methanococcus jannaschii* (*Methanocaldococcus jannaschii* DSM 2661) | Thermophile, DSM 2661, taxon: 2190 |
| Mja IF2 | *Methanococcus jannaschii* (*Methanocaldococcus jannaschii* DSM 2661) | Thermophile, DSM 2661, taxon: 2190 |
| Mja KlbA | *Methanococcus jannaschii* (*Methanocaldococcus jannaschii* DSM 2661) | Thermophile, DSM 2661, taxon: 2190 |
| Mja PEP | *Methanococcus jannaschii* (*Methanocaldococcus jannaschii* DSM 2661) | Thermophile, DSM 2661, taxon: 2190 |
| Mja Pol-1 | *Methanococcus jannaschii* (*Methanocaldococcus jannaschii* DSM 2661) | Thermophile, DSM 2661, taxon: 2190 |
| Mja Pol-2 | *Methanococcus jannaschii* (*Methanocaldococcus jannaschii* DSM 2661) | Thermophile, DSM 2661, taxon: 2190 |
| Mja RFC-1 | *Methanococcus jannaschii* (*Methanocaldococcus jannaschii* DSM 2661) | Thermophile, DSM 2661, taxon: 2190 |
| Mja RFC-2 | *Methanococcus jannaschii* (*Methanocaldococcus jannaschii* DSM 2661) | Thermophile, DSM 2661, taxon: 2190 |
| Mja RFC-3 | *Methanococcus jannaschii* (*Methanocaldococcus jannaschii* DSM 2661) | Thermophile, DSM 2661, taxon: 2190 |
| Mja RNR-1 | *Methanococcus jannaschii* (*Methanocaldococcus jannaschii* DSM 2661) | Thermophile, DSM 2661, taxon: 2190 |
| Mja RNR-2 | *Methanococcus jannaschii* (*Methanocaldococcus jannaschii* DSM 2661) | Thermophile, DSM 2661, taxon: 2190 |
| Mja RtcB (Mja Hyp-2) | *Methanococcus jannaschii* (*Methanocaldococcus jannaschii* DSM 2661) | Thermophile, DSM 2661, taxon: 2190 |
| Mja TFIIB | *Methanococcus jannaschii* (*Methanocaldococcus jannaschii* DSM 2661) | Thermophile, DSM 2661, taxon: 2190 |
| Mja UDP GD | *Methanococcus jannaschii* (*Methanocaldococcus jannaschii* DSM 2661) | Thermophile, DSM 2661, taxon: 2190 |
| Mja r-Gyr | *Methanococcus jannaschii* (*Methanocaldococcus jannaschii* DSM 2661) | Thermophile, DSM 2661, taxon: 2190 |
| Mja rPol A' | *Methanococcus jannaschii* (*Methanocaldococcus jannaschii* DSM 2661) | Thermophile, DSM 2661, taxon: 2190 |
| Mja rPol A" | *Methanococcus jannaschii* (*Methanocaldococcus jannaschii* DSM 2661) | Thermophile, DSM 2661, taxon: 2190 |
| Mka CDC48 | *Methanopyrus kandleri* AV19 | Thermophile, taxon: 190192 |
| Mka EF2 | *Methanopyrus kandleri* AV19 | Thermophile, taxon: 190192 |
| Mka RFC | *Methanopyrus kandleri* AV19 | Thermophile, taxon: 190192 |
| Mka RtcB | *Methanopyrus kandleri* AV19 | Thermophile, taxon: 190192 |
| Mka VatB | *Methanopyrus kandleri* AV19 | Thermophile, taxon: 190192 |

TABLE 2-continued

Naturally Occurring Inteins

| Intein Name | Organism Name | Organism Description |
|---|---|---|
| Mth RIR1 | Methanothermobacter thermautotrophicus (Methanobacterium thermoautotrophicum) | Thermophile, delta H strain |
| Mvu-M7 Helicase | Methanocaldococcus vulcanius M7 | Taxon: 579137 |
| Mvu-M7 Pol-1 | Methanocaldococcus vulcanius M7 | Taxon: 579137 |
| Mvu-M7 Pol-2 | Methanocaldococcus vulcanius M7 | Taxon: 579137 |
| Mvu-M7 Pol-3 | Methanocaldococcus vulcanius M7 | Taxon: 579137 |
| Mvu-M7 UDP GD | Methanocaldococcus vulcanius M7 | Taxon: 579137 |
| Neq Pol-c | Nanoarchaeum equitans Kin4-M | Thermophile, taxon: 228908 |
| Neq Pol-n | Nanoarchaeum equitans Kin4-M | Thermophile, taxon: 228908 |
| Nma-ATCC43099 MCM | Natrialba magadii ATCC 43099 | Taxon: 547559 |
| Nma-ATCC43099 PolB-1 | Natrialba magadii ATCC 43099 | Taxon: 547559 |
| Nma-ATCC43099 PolB-2 | Natrialba magadii ATCC 43099 | Taxon: 547559 |
| Nph CDC21 | Natronomonas pharaonis DSM 2160 | taxon: 348780 |
| Nph PolB-1 | Natronomonas pharaonis DSM 2160 | taxon: 348780 |
| Nph PolB-2 | Natronomonas pharaonis DSM 2160 | taxon: 348780 |
| Nph rPol A" | Natronomonas pharaonis DSM 2160 | taxon: 348780 |
| Pab CDC21-1 | Pyrococcus abyssi | Thermophile, strain Orsay, taxon: 29292 |
| Pab CDC21-2 | Pyrococcus abyssi | Thermophile, strain Orsay, taxon: 29292 |
| Pab IF2 | Pyrococcus abyssi | Thermophile, strain Orsay, taxon: 29292 |
| Pab KlbA | Pyrococcus abyssi | Thermophile, strain Orsay, taxon: 29292 |
| Pab Lon | Pyrococcus abyssi | Thermophile, strain Orsay, taxon: 29292 |
| Pab Moaa | Pyrococcus abyssi | Thermophile, strain Orsay, taxon: 29292 |
| Pab Pol-II | Pyrococcus abyssi | Thermophile, strain Orsay, taxon: 29292 |
| Pab RFC-1 | Pyrococcus abyssi | Thermophile, strain Orsay, taxon: 29292 |
| Pab RFC-2 | Pyrococcus abyssi | Thermophile, strain Orsay, taxon: 29292 |
| Pab RIR1-1 | Pyrococcus abyssi | Thermophile, strain Orsay, taxon: 29292 |
| Pab RIR1-2 | Pyrococcus abyssi | Thermophile, strain Orsay, taxon: 29292 |
| Pab RIR1-3 | Pyrococcus abyssi | Thermophile, strain Orsay, taxon: 29292 |
| Pab RtcB (Pab Hyp-2) | Pyrococcus abyssi | Thermophile, strain Orsay, taxon: 29292 |
| Pab VMA | Pyrococcus abyssi | Thermophile, strain Orsay, taxon: 29292 |
| Par RIR1 | Pyrobaculum arsenaticum DSM 13514 | taxon: 340102 |
| Pfu CDC21 | Pyrococcus furiosus | Thermophile, taxon: 186497, DSM3638 |
| Pfu IF2 | Pyrococcus furiosus | Thermophile, taxon: 186497, DSM3638 |
| Pfu KlbA | Pyrococcus furiosus | Thermophile, taxon: 186497, DSM3638 |
| Pfu Lon | Pyrococcus furiosus | Thermophile, taxon: 186497, DSM3638 |
| Pfu RFC | Pyrococcus furiosus | Thermophile, DSM3638, taxon: 186497 |
| Pfu RIR1-1 | Pyrococcus furiosus | Thermophile, taxon: 186497, DSM3638 |
| Pfu RIR1-2 | Pyrococcus furiosus | Thermophile, taxon: 186497, DSM3638 |
| Pfu RtcB (Pfu Hyp-2) | Pyrococcus furiosus | Thermophile, taxon: 186497, DSM3638 |
| Pfu TopA | Pyrococcus furiosus | Thermophile, taxon: 186497, DSM3638 |
| Pfu VMA | Pyrococcus furiosus | Thermophile, taxon: 186497, DSM3638 |
| Pho CDC21-1 | Pyrococcus horikoshii OT3 | Thermophile, taxon: 53953 |
| Pho CDC21-2 | Pyrococcus horikoshii OT3 | Thermophile, taxon: 53953 |
| Pho IF2 | Pyrococcus horikoshii OT3 | Thermophile, taxon: 53953 |
| Pho KlbA | Pyrococcus horikoshii OT3 | Thermophile, taxon: 53953 |
| Pho LHR | Pyrococcus horikoshii OT3 | Thermophile, taxon: 53953 |

TABLE 2-continued

Naturally Occurring Inteins

| Intein Name | Organism Name | Organism Description |
|---|---|---|
| Pho Lon | *Pyrococcus horikoshii* OT3 | Thermophile, taxon: 53953 |
| Pho Pol I | *Pyrococcus horikoshii* OT3 | Thermophile, taxon: 53953 |
| Pho Pol-II | *Pyrococcus horikoshii* OT3 | Thermophile, taxon: 53953 |
| Pho RFC | *Pyrococcus horikoshii* OT3 | Thermophile, taxon: 53953 |
| Pho RIR1 | *Pyrococcus horikoshii* OT3 | Thermophile, taxon: 53953 |
| Pho RadA | *Pyrococcus horikoshii* OT3 | Thermophile, taxon: 53953 |
| Pho RtcB (Pho Hyp-2) | *Pyrococcus horikoshii* OT3 | Thermophile, taxon: 53953 |
| Pho VMA | *Pyrococcus horikoshii* OT3 | Thermophile, taxon: 53953 |
| Pho r-Gyr | *Pyrococcus horikoshii* OT3 | Thermophile, taxon: 53953 |
| Psp-GBD Pol | *Pyrococcus* species GB-D | Thermophile |
| Pto VMA | *Picrophilus torridus*, DSM 9790 | DSM 9790, taxon: 263820, Thermoacidophile |
| Smar 1471 | *Staphylothermus marinus* F1 | taxon: 399550 |
| Smar MCM2 | *Staphylothermus marinus* F1 | taxon: 399550 |
| Tac-ATCC25905 VMA | Thermoplasma acidophilum, ATCC 25905 | Thermophile, taxon: 2303 |
| Tac-DSM1728 VMA | *Thermoplasma acidophilum*, DSM1728 | Thermophile, taxon: 2303 |
| Tag Pol-1 (Tsp-TY Pol-1) | *Thermococcus aggregans* | Thermophile, taxon: 110163 |
| Tag Pol-2 (Tsp-TY Pol-2) | *Thermococcus aggregans* | Thermophile, taxon: 110163 |
| Tag Pol-3 (Tsp-TY Pol-3) | *Thermococcus aggregans* | Thermophile, taxon: 110163 |
| Tba Pol-II | *Thermococcus barophilus* MP | taxon: 391623 |
| Tfu Pol-1 | *Thermococcus fumicolans* | Thermophilem, taxon: 46540 |
| Tfu Pol-2 | *Thermococcus fumicolans* | Thermophile, taxon: 46540 |
| Thy Pol-1 | *Thermococcus hydrothermalis* | Thermophile, taxon: 46539 |
| Thy Pol-2 | *Thermococcus hydrothermalis* | Thermophile, taxon: 46539 |
| Tko CDC21-1 | *Thermococcus kodakaraensis* KOD1 | Thermophile, taxon: 69014 |
| Tko CDC21-2 | *Thermococcus kodakaraensis* KOD1 | Thermophile, taxon: 69014 |
| Tko Helicase | *Thermococcus kodakaraensis* KOD1 | Thermophile, taxon: 69014 |
| Tko IF2 | *Thermococcus kodakaraensis* KOD1 | Thermophile, taxon: 69014 |
| Tko KlbA | *Thermococcus kodakaraensis* KOD1 | Thermophile, taxon: 69014 |
| Tko LHR | *Thermococcus kodakaraensis* KOD1 | Thermophile, taxon: 69014 |
| Tko Pol-1 (Pko Pol-1) | *Pyrococcus/Thermococcus kodakaraensis* KOD1 | Thermophile, taxon: 69014 |
| Tko Pol-2 (Pko Pol-2) | *Pyrococcus/Thermococcus kodakaraensis* KOD1 | Thermophile, taxon: 69014 |
| Tko Pol-II | *Thermococcus kodakaraensis* KOD1 | Thermophile, taxon: 69014 |
| Tko RFC | *Thermococcus kodakaraensis* KOD1 | Thermophile, taxon: 69014 |
| Tko RIR1-1 | *Thermococcus kodakaraensis* KOD1 | Thermophile, taxon: 69014 |
| Tko RIR1-2 | *Thermococcus kodakaraensis* KOD1 | Thermophile, taxon: 69014 |
| Tko RadA | *Thermococcus kodakaraensis* KOD1 | Thermophile, taxon: 69014 |
| Tko TopA | *Thermococcus kodakaraensis* KOD1 | Thermophile, taxon: 69014 |
| Tko r-Gyr | *Thermococcus kodakaraensis* KOD1 | Thermophile, taxon: 69014 |
| Tli Pol-1 | *Thermococcus litoralis* | Thermophile, taxon: 2265 |
| Tli Pol-2 | *Thermococcus litoralis* | Thermophile, taxon: 2265 |
| Tma Pol | *Thermococcus marinus* | taxon: 187879 |
| Ton-NA1 LHR | *Thermococcus onnurineus* NA1 | Taxon: 523850 |
| Ton-NA1 Pol | *Thermococcus onnurineus* NA1 | taxon: 342948 |
| Tpe Pol | *Thermococcus peptonophilus* strain SM2 | taxon: 32644 |
| Tsi-MM739 Lon | *Thermococcus sibiricus* MM 739 | Thermophile, Taxon: 604354 |
| Tsi-MM739 Pol-1 | *Thermococcus sibiricus* MM 739 | Taxon: 604354 |
| Tsi-MM739 Pol-2 | *Thermococcus sibiricus* MM 739 | Taxon: 604354 |
| Tsi-MM739 RFC | *Thermococcus sibiricus* MM 739 | Taxon: 604354 |
| Tsp AM4 RtcB | *Thermococcus* sp. AM4 | Taxon: 246969 |
| Tsp-AM4 LHR | *Thermococcus* sp. AM4 | Taxon: 246969 |
| Tsp-AM4 Lon | *Thermococcus* sp. AM4 | Taxon: 246969 |
| Tsp-AM4 RIR1 | *Thermococcus* sp. AM4 | Taxon: 246969 |
| Tsp-GE8 Pol-1 | *Thermococcus* species GE8 | Thermophile, taxon: 105583 |
| Tsp-GE8 Pol-2 | *Thermococcus* species GE8 | Thermophile, taxon: 105583 |
| Tsp-GT Pol-1 | *Thermococcus* species GT | taxon: 370106 |
| Tsp-GT Pol-2 | *Thermococcus* species GT | taxon: 370106 |
| Tsp-OGL-20P Pol | *Thermococcus* sp. OGL-20P | taxon: 277988 |
| Tthi Pol | *Thermococcus thioreducens* | Hyperthermophile |
| Tvo VMA | *Thermoplasma volcanium* GSS1 | Thermophile, taxon: 50339 |
| Tzi Pol | *Thermococcus zilligii* | taxon: 54076 |
| Unc-ERS PFL | uncultured archaeon GZfos13E1 | isolation_source = "Eel River sediment", clone = "GZfos13E1", taxon: 285397 |
| Unc-ERS RIR1 | uncultured archaeon GZfos9C4 | isolation_source = "Eel River sediment", taxon: 285366, clone = "GZfos9C4" |

TABLE 2-continued

Naturally Occurring Inteins

| Intein Name | Organism Name | Organism Description |
|---|---|---|
| Unc-ERS RNR | uncultured archaeon GZfos10C7 | isolation_source = "Eel River sediment", clone = "GZfos10C7", taxon: 285400 |
| Unc-MetRFS MCM2 | uncultured archaeon (Rice Cluster I) | Enriched methanogenic consortium from rice field soil, taxon: 198240 |

Inteins of the disclosed compositions or that can be used in the disclosed methods can be modified, or mutated, inteins. A modified intein can comprise additional amino acids at the N-terminus of a naturally occurring intein, or can be at the C-terminus, or within the intein. In a non-limiting example, there can be one, two, three, four, five, or more additional amino acids at the N-terminus of the naturally occurring intein. In some aspects, the first amino acid at the N-terminal end of the intein can be alanine, histidine, cysteine or glycine.

In addition to the modification of comprising a reversible ZBM, an intein can also include other modifications that can make it useful for various applications. In other words, an intein with a ZBM can also comprise other modifications. For example, an intein can comprise another tunable motif that is useful for modifying behavior. For example, inteins can be encoded by a temperature-sensitive intein allele (Adam et al. 2002, Mol. Microbiol. Biotechnol. 4 479-487; Cann et al. 2004, Appl. Environ. Microbiol. 70 3158-3162; Zeidler et al. 2004, Nat. Biotechnol. 22 871-876), inteins can incorporate nonnative amino acids whose activity is regulated by photolysis (Cook et al. 1995 Angew. Chem. Int. Ed. Engl. 34 1629-1630), or the activity of inteins can be ligand-controlled (Mills et al. 2001, J. Biol. Chem. 276 10832-10838; Mootz et al. 2002, J. Am. Chem. Soc. 124 9044-9045; Mootz et al. 2003, J. Am. Chem. Soc. 125 10561-10569). It has also been shown that controllable intein splicing in cis can be used for various applications that will be appreciated by those skilled in the art. In the first case, regulation of protein activity was accomplished with the isolation and use of temperature-sensitive variants of the *Saccharomyces cerevisiae* vacuolar ATPase subunit intein (Zeidler et al. 2004) and, in the second case, with the construction of a novel chimeric intein whose splicing activity is triggered by the addition of 4-hydroxytamoxifen (Buskirk et al. Proc. Natl. Acad. Sci. 101 10505-10510).

Another example of modified inteins is a protein engineering approach for generating inteins whose splicing activity is regulated in vivo by the presence of human thyroid hormone. Designed according to other engineered allosteric enzyme prototypes (Baird et al. 1999, Proc. Natl. Acad. Sci. 96 11241-11246; Doi et al. 1999, FEBS Lett. 453 305-307; Tucker et al. 2001, Nat. Biotechnol. 19 1042-1046; Guntas et al, 2004, J. Mol. Biol. 336 263-273), an artificial intein chimera was created by fusing a thyroid-hormone-binding domain within a previously engineered mini-intein. The insertion of the binding domain abolished the splicing activity of the intein but allowed it to be later restored by addition of thyroid hormone or synthetic analogs. The resulting allosteric intein was then used to conditionally activate a variety of different proteins in *Escherichia coli* in a dose-dependent manner. Finally, a combination of directed evolution and genetic selection was employed to engineer an additional controllable intein whose splicing activity is inhibited by the presence of an orthogonal set of synthetic estrogen ligands.

Further examples of modified inteins include, but are not limited to, those found in U.S. Pat. No. 7,026,526, such as mutated inteins of *Pyrococcus* species GB-D DNA polymerase, and those created artificially by removing the endonuclease domains from endonuclease containing inteins (Xu, M-Q & Perler, F. B. EMBO Journal, 1996, 15, 5146-5153; Chong, et al. J. Biol. Chem. 1997, 272, 15587-15590). In a further example, an intein can be selected so that it consists of the minimal number of amino acids needed to perform the splicing function, such as the intein from the *Mycobacterium xenopi* GyrA protein (Telenti, A., et al., J. Bacteriol. 1997, 179, 6378-6382). In another aspect, an intein without endonuclease activity can be selected, such as the intein from the *Mycobacterium xenopi* GyrA protein or the *Saccharaomyces cerevisiae* VMA intein that has been modified to remove endonuclease domains (Chong, 1997).

In some aspects, the first residue of the C-terminal extein is engineered to contain a glycine or alanine, a modification that was shown to prevent extein ligation with the *Pyrococcus* species GB-D DNA polymerase (Xu, M-Q & Perler, F. B. EMBO Journal, 1996, 15, 5146-5153). In this embodiment, preferred C-terminal exteins contain coding sequences that naturally contain a glycine or an alanine residue following the N-terminal methionine in the native amino acid sequence. Fusion of the glycine or alanine of the extein to the C-terminus of the intein can provide the native amino acid sequence after processing of the polypeptide. In another embodiment, an artificial glycine or alanine is created on the C-terminal extein either by altering the native sequence or by adding an additional amino acid residue onto the N-terminus of the native sequence. In this example, the native amino acid sequence of the protein is altered by one amino acid after polypeptide processing.

A further example of a modified intein includes the Pch PRP8 mini-intein of *Penicillium chrysogenum*, which was modified to include: 1) aminoglycoside phosphotransferase; 2) imidazoleglycerol-phosphate dehydratase, His5 from *S. pombe* 3) hygromycin B phosphotransferase; and 4) the transcriptional activator LexA-VP16 (Muller et al., BMC Biotechnology 2011, 11:71).

U.S. Pat. No. 5,834,247 teaches that modification of inteins can be accomplished in a number of ways and is hereby incorporated by reference in its entirety for its teaching of methods that can be used to modify inteins. For example, the sequence surrounding the amino acid residue to be modified may be altered to create a biological phosphorylation site allowing it to be a substrate for specific kinases and phosphatases. Examples of protein kinases include, for example, casein kinase II, cAMP-dependent protein kinase, cdc2, and pp60c-src (Pearson and Kemp, Methods in Enzymology 200:62 (1991)). Examples of phosphatases include, for example, protein phosphatase 2A, lambda phosphatase, and the yop phosphatase from *Yersinia* (Tonks, Current Opinion in Cell Biology, 2:1114 (1990)).

Additionally, critical splice junction residues can be modified chemically such that the splicing reaction is blocked until the modification is reversed. This can be accomplished by using, for example, unnatural amino acid mutagenesis (Noren, et al., Science 244:182 (1989); Ellman, et al., Methods in Enzymology 202:301 (1991)). Using this method, one of the amino acids involved in the splicing reaction can be replaced, during translation, by a synthetic derivative in which the side chain functionality of the side chain is "masked" by a chemically or photolytically removable group.

In another example, certain host cells may not be able to tolerate the gene product of the CIPS, and thus, in some embodiments it may be preferable to inactivate the endonuclease function. It has been shown that protein splicing can occur when the CIPS endonuclease function has been inactivated. Such inactivation can be accomplished in a variety of ways, including for example, random mutagenesis, deletion or insertional inactivation, or site directed mutagenesis. In one example, the endonuclease function is inactivated by site directed mutagenesis. 1-Tli-1 shares sequence similarity with other "homing endonucleases" in the pair of characteristic dodecapeptide motifs (Cummings et al., Curr. Gent. 16:381 (1989)). Inactivation of endonuclease function has been shown to increase the stability of constructs carrying modified proteins.

Also disclosed in U.S. Pat. No. 6,933,362 (herein incorporated by reference in its entirety for its teaching concerning mutated inteins), are various modified inteins. For example, U.S. Pat. No. 6,933,362 discusses a non-naturally occurring intein having splicing activity and controllable cleavage activity or a non-naturally occurring compound having cleaving and/or cleaving and splicing activity, which is controllable. The intein can comprise a truncated intein. The cleavage activity can be controllable by varying oxidative potential. The intein can be obtained from random mutagenesis of a truncated intein, followed by selection based on growth phenotype. The intein can have C-terminal cleavage. The intein can be a truncated Mtu intein. The intein can have the endonuclease domain deleted. The intein can be a truncated Mtu intein with the endonuclease domain deleted, and V67L and/or D422G mutation(s) (relative to full-length Mtu intein). The intein can contain the C-terminal histidine-asparagine. (The presence of the C-terminal histidine residue is believed to confer pH sensitivity and thus it is advantageous that the C-terminal histidine be present; the final asparagine is believed useful for cleavage activity.)

Furthermore, one of skill in the art can readily discern useful modified inteins by the use of an effective screen for linking intein activity to an easily observable or selectable phenotype. Such screens are known in the art, for example those found in U.S. Pat. No. 6,933,362. Furthermore, the screen can allow for selection of desired traits under conditions that are relevant for the proposed application. An intein derivative exhibiting controllable cleavage activity has been isolated using rational and random mutagenesis followed by a genetic screen.

Affinity Tags

Disclosed herein are modified peptides comprising a CIPS wherein the modified peptide comprises the structure: X1-CIPS, wherein X1 is an affinity tag, and wherein the CIPS comprises a reversible ZBM and an intein.

Affinity tags can be short peptide sequences or functional protein domains cloned in frame with protein coding sequences that change the protein's behavior. Affinity tags can be appended to the N- or C-terminus of proteins which can be used in methods of purifying a protein from cells. Cells expressing a peptide comprising an affinity tag can be pelleted, lysed, and applied to a column, resin or other solid support that displays a ligand to the affinity tags. The solid support can also be washed several times with buffer to eliminate unbound proteins. A protein of interest, if attached to an affinity tag, can be eluted from the solid support via a buffer that causes the affinity tag to dissociate from the ligand resulting in a purified protein.

Examples of affinity tags can be found in Kimple et al. Curr Protoc Protein Sci 2004 September; Arnau et al. Protein Expr Purif 2006 July; 48(1) 1-13; Azarkan et al. J Chromatogr B Analyt Technol Biomed Life Sci 2007 Apr. 15; 849(1-2) 81-90; and Waugh et al. Trends Biotechnol 2005 June; 23(6) 316-20, all hereby incorporated by reference in their entirety for their teaching of examples of affinity tags.

Examples of affinity include, but are not limited to, maltose binding protein, which can bind to immobilized maltose to facilitate purification of the fused target protein; Chitin binding protein, which can bind to immobilized chitin; Glutathione S transferase, which can bind to immobilized chitin; Poly-histidine, which can bind to immobilized chelated metals; FLAG octapeptide, which can bind to immobilized anti-FLAG antibodies.

Affinity tags can also be used to facilitate the purification of a protein of interest using the disclosed modified peptides through a variety of methods, including, but not limited to, selective precipitation, ion exchange chromatography, binding to precipitation-capable ligands, dialysis (by changing the size and/or charge of the target protein) and other highly selective separation methods.

In some aspects, affinity tags can be used that do not actually bind to a ligand. For example, an ELP tag, protein A or Protein G-binding domains can be used as affinity tags.

Linkers

The CIPSs disclosed herein can be attached to an affinity tag by a variety of means. For example, the CIPSs disclosed herein can be attached to an affinity tag through a linker sequence. The linker sequence can be designed to create distance between the intein and affinity tag, while providing minimal steric interference to the intein cleaving active site. It is generally accepted that linkers involve a relatively unstructured amino acid sequence, and the design and use of linkers are common in the art of designing fusion peptides. There is a variety of protein linker databases which one of skill in the art will recognize. This includes those found in Argos et al. J Mol Biol 1990 Feb. 20; 211(4) 943-58; Crasto et al. Protein Eng 2000 May; 13(5) 309-12; George et al. Protein Eng 2002 November; 15(11) 871-9; Arai et al. Protein Eng 2001 August; 14(8) 529-32; and Robinson et al. PNAS May 26, 1998 vol. 95 no. 11 5929-5934, hereby incorporated by reference in their entirety for their teaching of examples of linkers.

Examples of linkers include, but are not limited to: (1) poly-asparagine linker consisting of 4 to 15 asparagine residues, and (2) glycine-serine linker, consisting of various combinations and lengths of polypeptides consisting of glycine and serine. One of skill in the art can easily identify and use any linker that will successfully link the CIPS with an affinity tag.

Proteins of Interest

Proteins of interest, can include, for example, enzymes, toxins, cytokines, glycoproteins, growth factors, therapeutic proteins, such as antibodies as well as any other protein sought to be purified or used by one of skill in the art. The amino acid and nucleotide sequence of such proteins are easily available through many computer databases, for example, GenBank, EMBL and Swiss-Prot. Alternatively, the nucleotide or amino acid sequence of a protein of interest can be determined using routine procedures known in the art.

In some aspects disclosed herein, a protein of interest can be attached to a CIPS so that it can be purified. This is discussed in more detail herein. In some methods described herein, the protein of interest can be a protein that one wishes to purify and accumulate, such as an antibody.

Plasmids, Vectors, and Cell Lines

Disclosed herein are vectors comprising nucleic acids encoding the CIPSs disclosed herein, as well as cell lines comprising said vectors. Examples of CIPSs that can be encoded in the vectors disclosed herein can be found at least in FIG. 17, as well as throughout this disclosure.

As used herein, plasmid or viral vectors are agents that transport the disclosed nucleic acids, such as those encoding a CIPS and a peptide of interest, and/or an affinity tag, for example, into a cell without degradation and include a promoter yielding expression of the gene in the cells into which they can be delivered. In one example, a CIPS and peptide of interest are derived from either a virus or a retrovirus. Viral vectors can be, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also disclosed are any viral families which share the properties of these viruses which make them suitable for use as vectors. Retroviruses include Murine Maloney Leukemia virus, MMLV and retroviruses that express the desirable properties of MMLV as a vector. Retroviral vectors are able to carry a larger genetic payload, i.e., a transgene or marker gene, than other viral vectors and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes; they are thermostable and can be stored at room temperature. Disclosed herein is a viral vector which has been engineered so as to suppress the immune response of a host organism, elicited by the viral antigens. Vectors of this type can carry coding regions for Interleukin 8 or 10.

Viral vectors can have higher transaction (ability to introduce genes) abilities than chemical or physical methods to introduce genes into cells. Typically, viral vectors contain nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promoter cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

The fusion DNA encoding a modified peptide can be inserted into an appropriate expression vector, i.e., a vector which contains the necessary elements for the transcription and translation of the inserted protein-coding sequence. Depending on the host-vector system utilized, any one of a number of suitable transcription and translation elements can be used. For instance, when expressing a modified eukaryotic protein, it can be advantageous to use appropriate eukaryotic vectors and host cells. Expression of the fusion DNA results in the production of a modified protein.

Also disclosed herein are cell lines comprising the vectors or peptides disclosed herein. A variety of cells can be used with the vectors and plasmids disclosed herein. Non-limiting examples of such cells include somatic cells such as blood cells (erythrocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, thymic nurse cells, Schwann cells, etc.). Eukaryotic germ cells (spermatocytes and oocytes) can also be used, as can the progenitors, precursors and stem cells that give rise to the above-described somatic and germ cells. These cells, tissues and organs can be normal, or they can be pathological such as those involved in diseases or physical disorders, including, but not limited to, infectious diseases (caused by bacteria, fungi yeast, viruses (including HIV, or parasites); in genetic or biochemical pathologies (e.g., cystic fibrosis, hemophilia, Alzheimer's disease, schizophrenia, muscular dystrophy, multiple sclerosis, etc.); or in carcinogenesis and other cancer-related processes.

The eukaryotic cell lines disclosed herein can be animal cells, plant cells (monocot or dicot plants) or fungal cells, such as yeast. Animal cells include those of vertebrate or invertebrate origin. Vertebrate cells, especially mammalian cells (including, but not limited to, cells obtained or derived from human, simian or other non-human primate, mouse, rat, avian, bovine, porcine, ovine, canine, feline and the like), avian cells, fish cells (including zebrafish cells), insect cells (including, but not limited to, cells obtained or derived from *Drosophila* species, from *Spodoptera* species (e.g., Sf9 obtained or derived from *S. frugiperida*, or HIGH FIVE™ cells) or from *Trichoplusa* species (e.g., MG1, derived from *T. ni*)), worm cells (e.g., those obtained or derived from *C. elegans*), and the like. It will be appreciated by one of skill in the art, however, that cells from any species besides those specifically disclosed herein can be advantageously used in accordance with the vectors, plasmids, and methods disclosed herein, without the need for undue experimentation. Examples of useful cell lines include, but are not limited to, HT1080 cells (ATCC CCL 121), HeLa cells and derivatives of HeLa cells (ATCC CCL 2, 2.1 and 2.2), MCF-7 breast cancer cells (ATCC BTH 22), K-562 leukemia cells (ATCC CCL 243), KB carcinoma cells (ATCC CCL 17), 2780AD ovarian carcinoma cells (see Van der Buick, A. M. et al., Cancer Res. 48:5927-5932 (1988), Raji cells (ATCC CCL 86), Jurkat cells (ATCC TIB 152), Namalwa cells (ATCC CRL 1432), HL-60 cells (ATCC CCL 240), Daudi cells (ATCC CCL 213), RPMI 8226 cells (ATCC CCL 155), U-937 cells (ATCC CRL 1593), Bowes Melanoma cells (ATCC CRL 9607), WI-38VA13 subline 2R4 cells (ATCC CLL 75.1), and MOLT-4 cells (ATCC CRL 1582), as well as heterohybridoma cells produced by fusion of human cells and cells of another species. Secondary human fibroblast strains, such as WI-38 (ATCC CCL 75) and MRC-5 (ATCC CCL 171 can also be used. Other mammalian cells and cell lines can be used in accordance with the present invention, including, but not limited to CHO cells, COS cells, VERO cells, 293 cells, PER-C6 cells, M1 cells, NS-1 cells, COS-7 cells, MDBK cells, MDCK cells, MRC-5 cells, WI-38 cells, WEHI cells, SP2/0 cells, BHK cells (including BHK-21 cells); these and other cells and cell lines are available commercially, for example from the American Type Culture Collection (P.O. Box 1549, Manassas, Va. 20108 USA). Many other cell lines are known in the art and will be familiar to the ordinarily skilled artisan; such cell lines therefore can be used equally well.

Also disclosed herein are cell-free protein expression systems comprising the vectors or peptides disclosed herein, and which also include the required cellular components for expression of a protein from isolated DNA or mRNA molecules. A variety of available cell-free expression systems can be used with the vectors and plasmids disclosed herein. Non-limiting examples of such systems include the Thermo Scientific Pierce Human In Vitro Protein Expression System (based on human cells), Rabbit Reticulocyte Lysate Systems (commercially available from Life Technologies and other suppliers and based on rabbit cells), Wheat Germ Extract Systems (available from several suppliers, and based on wheat germ cells), E. coli Cell-Free Systems (based on E. coli cell lysates and available from several suppliers), and the EasyXpress Insect Kit (available from Qiagen, and based on Spodoptera frugiperda insect cell extracts, with other versions also available from other suppliers).

Once obtained, the proteins of interest can be separated and purified by appropriate combination of known techniques. These methods include, for example, methods utilizing solubility such as salt precipitation and solvent precipitation; methods utilizing the difference in molecular weight such as dialysis, ultra-filtration, gel-filtration, and SDS-polyacrylamide gel electrophoresis; methods utilizing a difference in electrical charge such as ion-exchange column chromatography; methods utilizing specific affinity such as affinity chromatography; methods utilizing a difference in hydrophobicity such as reverse-phase high performance liquid chromatography; and methods utilizing a difference in isoelectric point, such as isoelectric focusing electrophoresis. These are discussed in more detail below.

Methods of Purifying a Protein

Disclosed herein are methods of producing or purifying a protein of interest, the method comprising: producing a modified peptide with the structure:

X1-CIPS-X2 wherein X1 is an affinity tag, and X2 comprises a protein of interest. The modified peptide comprising the affinity tag, protein of interest, and CIPS can then be exposed to a concentration of zinc which inhibits splicing or cleavage by the CIPS. The modified peptide can then be isolated, such as by protein purification, and the zinc removed, thereby allowing for splicing or cleavage of the protein of interest, thereby producing the protein of interest. The CIPS can be isolated by using the affinity tag.

Disclosed herein are methods of producing a modified peptide comprising a CIPS, the method comprising: (a) preparing a nucleic acid that encodes one or more peptides comprising a CIPS; (b) transforming a host cell with the nucleic acid; and (c) culturing the transformed host cell under conditions suitable for the expression of the modified peptide comprising a CIPS encoded by the nucleic acid. Such methods can further comprise isolating the modified peptide comprising a CIPS.

A peptide or protein produced using the methods disclosed herein can be a peptide or protein of interest or a therapeutic peptide or protein. Cell lines that can be used with the methods disclosed herein, include, but are not limited to mammalian cells such as CHO cells.

Disclosed herein are methods of producing a modified peptide comprising a CIPS, the method comprising: (a) preparing a nucleic acid that encodes one or more peptides comprising a CIPS; (b) transforming a host cell with the nucleic acid; and (c) culturing the transformed host cell under conditions suitable for the expression of the modified peptide comprising a CIPS encoded by the nucleic acid, further comprising the additional step of (d) exposing the modified peptide comprising the CIPS to a chemical reagent which inhibits splicing or cleavage.

Disclosed herein are methods of producing a modified peptide comprising a CIPS, the method comprising: (a) preparing a nucleic acid that encodes one or more peptides comprising a CIPS; (b) transforming a host cell with the nucleic acid; and (c) culturing the transformed host cell under conditions suitable for the expression of the modified peptide comprising a CIPS encoded by the nucleic acid, further comprising (d) exposing the modified peptide comprising the CIPS to a chemical reagent, such as zinc, which inhibits splicing or cleavage and (e) exposing the modified peptide to a chelating agent, a change in pH, a change in temperature, dialysis, or dilution, thereby removing the chemical reagent, for instance zinc.

Disclosed herein are methods of producing a modified peptide comprising a CIPS, the method comprising: (a) forming a nucleic acid encoding a peptide comprising a CIPS; (b) transforming a host cell with the nucleic acid of step (a); and (c) culturing the transformed host cell under conditions suitable for the expression of the modified peptide comprising the CIPS.

Disclosed herein are methods of producing a protein of interest comprising: (a) preparing a nucleic acid that encodes a modified peptide comprising a CIPS wherein the modified peptide comprises the structure: X1-CIPS-X2, wherein X1 is an affinity tag, and wherein the CIPS comprises a reversible zinc-binding motif and an intein, and wherein X2 comprises the protein of interest; (b) transforming a host cell with the nucleic acid; (c) culturing the transformed host cell under conditions suitable for the expression of the modified peptide; (d) exposing the modified peptide to a concentration of zinc which inhibits splicing or cleavage by the CIPS; (e) isolating the modified peptide; and (f) removing the zinc, thereby allowing for cleavage of the protein of interest from the modified peptide, thereby producing the substantially purified protein of interest. The protein of interest can be a therapeutic protein.

Disclosed herein are methods of producing a protein of interest comprising: (a) preparing a nucleic acid that encodes a modified peptide comprising a CIPS wherein the modified peptide comprises the structure: X1-CIPS-X2, wherein X1 is an affinity tag, and wherein the CIPS comprises a reversible zinc-binding motif and an intein, and wherein X2 comprises the protein of interest; (b) transforming a host cell with the nucleic acid; (c) culturing the transformed host cell under conditions suitable for the expression of the modified peptide; (d) exposing the modified peptide to zinc at a concentration of 200 µM or greater; (e) isolating the modified peptide; and (f) removing the zinc, thereby allowing for splicing or cleavage of the protein of interest from the modified peptide, thereby producing the substantially purified protein of interest.

Disclosed herein are methods for binding and eluting a phage-displayed polypeptide from a protein of interest comprising: (a) producing a modified peptide with the structure: X1-CIPS-X2, wherein X1 is an affinity tag, the CIPS comprises a reversible zinc-binding motif and an intein and X2 comprises a protein of interest; (b) binding the modified peptide of step (a) to a solid support; (c) contacting a phage-displayed polypeptide with the support-bound peptide of step (b), thereby permitting binding of the phage-displayed polypeptide with the peptide comprising the CIPS; (d) removing unbound phage-displayed polypeptides; and, (e) eluting the bound phage-displayed polypeptide by inducing cleavage of the protein of interest by the CIPS.

Also disclosed herein are methods for binding and eluting a phage-displayed polypeptide from a protein of interest, comprising: producing a modified peptide with the structure:

X1-CIPS-X2 wherein X1 is an affinity tag, the CIPS comprises a reversible zinc-binding motif and an intein and X2 comprises a protein of interest. The modified peptide which comprises the CIPS can then be bound to a solid support. The phage-displayed polypeptide can then be contacted with the support-bound peptide (the peptide with the CIPS), thereby permitting binding of the phage-displayed polypeptide with the peptide comprising the CIPS. Any unbound phage-displayed polypeptide can then be removed, and the bound phage-displayed polypeptide is eluted by inducing cleavage of the protein of interest by the CIPS.

The modified peptide comprising the CIPS can be exposed to a chemical agent, such as zinc, which inhibits splicing or cleavage, until the phage-displayed polypeptide is bound.

The chemical agent (such as zinc) that inhibits splicing or cleavage can be removed by using a chelating agent, changing the temperature, changing the pH, dialysis, or dilution of the chemical agent. The phage-displayed polypeptide can comprise a library of at least two sequence variations of the displayed polypeptides. The phage can also be filamentous.

Fusion protein purification systems are well known to the skilled artisan. See, EPO 0 286 239 and N. M. Sassenfeld, TIBTECH, 8:88-93 (1990). Typically, in such systems, a binding protein and a target protein are joined by a linker having a protease recognition site. The fusion is then purified by affinity chromatography on a substrate having affinity for the binding protein. The binding protein and the target protein are then separated by contact with a protease, e.g., factor Xa. In these systems, in order to obtain a highly purified target protein, the protease must be separated from the target protein, thus adding an additional purification step, as well as the potential for contamination. The method disclosed herein, by using a CIPS, instead of a protease, avoids these and other problems encountered in currently used protein fusion purification systems.

Also disclosed are modified peptides comprising a fusion protein in which a CIPS is between the protein of interest and a protein or peptide having affinity for a substrate (binding protein or binding domain). Techniques for forming such fusion proteins are well known to the skilled artisan. See, EPO 0 286 239 and J. Sambrook, et al., Molecular Cloning: A Laboratory Manual (1989), Cold Spring Harbor Laboratory Press, Cold Spring Harbor, N.Y. p. 17.29-17.33.

Binding proteins which can be employed in the methods disclosed herein include, for example, sugar binding proteins, such as maltose or arabinose binding protein, receptor binding proteins, amino acid binding proteins and metal binding proteins. Another is a chitin binding protein, or the chitin binding domain of a chitinase. Other binding proteins are well known to the skilled artisan. See, EPO 0 286 239 and N. M. Sassenfeld, TIBTECH, supra.

A modified peptide can then be contacted with a substrate to which the binding protein has specific affinity, e.g., using affinity chromatography. A highly purified protein of interest can be liberated from the column by changing conditions, such as removing zinc, under which cleavage is initiated, for example, between the CIPS and the protein of interest. Alternatively, a purified fusion protein can be eluted from the column and liberated as above.

A CIPS disclosed herein can also be used to isolate modified peptides by use of affinity chromatography with antibodies specific to the CIPS. For example, monoclonal or polyclonal antibodies can be generated having binding affinity to a CIPS using standard techniques. These antibodies can then be utilized in affinity chromatography purification procedures to isolate a modified peptide. After purification, if desired, zinc can be removed, at which time the CIPS will undergo excision.

Methods of Producing a Peptide

Disclosed herein are methods of producing a modified peptide comprising a CIPS, the method comprising: forming a nucleic acid encoding a CIPS, and transforming a host cell with the nucleic acid; and culturing the transformed host cell under conditions suitable for the expression of the peptide comprising the CIPS. The modified protein can comprise a protein of interest, which can be a therapeutic protein, such as an antibody. The modified peptide can also comprise an affinity tag.

The methods disclosed herein can comprise the additional step of exposing the modified peptide comprising the CIPS to a chemical reagent which inhibits splicing or cleavage. This chemical reagent can be zinc, for example, and can be at a concentration below 1000 µM, for example. Additionally, the peptide comprising the CIPS can be exposed to a chelating agent, a change in pH, dialysis, or dilution, thereby removing zinc.

Kits

Disclosed herein are kits comprising a CIPS, or a CIPS linked to an affinity tag and/or a protein of interest. Also disclosed are kits comprising peptides comprising one or more of SEQ ID NOS: 11, 15, 19, 23, 27, or 31. Also disclosed are kits comprising nucleic acids, comprising one or more of SEQ ID NOS: 12, 16, 20, 24, 28, or 32. Also disclosed are kits comprising the vectors, plasmids, and/or the cell lines disclosed herein. In a further example, a kit can comprise zinc. Zinc, for example, can be at a concentration of 1000 µM or less.

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLES

Example 1—In Silico Design

Nearly all inteins end with a Histidine-Asparagine Dipeptide (FIG. 3). The histidine is believed to be involved in the cleaving reaction, and the fact that the pH sensitivity of the cleaving reaction follows the pKa titration curve for Histidine also suggests this. One additional piece of evidence is that metal ions, and especially zinc, can suppress intein cleaving at high concentrations. This is presumably due to their binding to the Histidine. The development of stronger zinc-binding to this particular Histidine residue formed the basis for the rational intein design.

The tested zinc-binding motifs (ZBMs) are computationally designed to have high potential zinc-binding affinity and to interrupt intein activity through coordination of critical intein active site histidine residue side chains. Considered in the design were (1) the position to insert zinc-binding motif into intein and (2) the sequences to bind zinc with or without using existing residues that occur near the intein active site. Conceptually the intention was to adapt a minimal portion of previously reported ZBMs that did not require cysteine residues (for example 1ZE9). The subdomain was engineered proximal to the activity site. This is substantially different from previously reported work where control attempts were made using insertions into the distal 'control loop' region of the intein or through random mutagenesis approaches. A panel of related designs having subtle variations in predicted zinc coordination behaviors was tested.

In a notable design that is exemplary of the six initial designs, the last two naturally occurring intein amino acids were replaced and the short sub-domain/motif 'xExHH' was further appended to the intein N-terminus to give for example . . . x(E-2)x(H0)(H1)(L2)AEGT. This form can act through metal-coordination with H439, inhibiting H439's interactions with N440 in the active site. The related motifs subtly alter the orientation and distances of metal coordination bonds within the switch subdomain. The specific amino acid sequences of the six core inventive designs are:

```
                                       (SEQ ID NO: 39)
LN001:  . . . xGEGHHLAEGT . . .

(SEQ ID NO: 40)
LN002:  . . . xGEGHCLAEGT . . .

(SEQ ID NO: 41)
LN003:  . . . xGEGHHALAEGT . . .

(SEQ ID NO: 42)
LN004:  . . . xGEGHGCLAEGT . . .

(SEQ ID NO: 43)
LN003B: . . . xGDGHGCLAEGT . . .

(SEQ ID NO: 44)
LN004B: . . . xGDGHGCLAEGT . . .
```

These sequences were subjected to computational modeling using Schrodinger Q-SITE and Impact packages run with explicit solvent and a quantum mechanical simulation set that included the zinc metal ion and the amino acid side chain, separated from the molecular modeling region using hydrogen caps between the alpha and beta carbons (See FIG. 5A-F). The simulations were run with and without a metal center to look for structures that were distorted upon insertion of the metal. The structures represented a range of conformations, all of which had potential to inhibit the intein active site upon zinc-binding.

Common wisdom predicted that the designs might result in a constitutively inactive intein due to steric and electronic disruption of the active site. However, it was shown that this was not the case for the disclosed amino acid sequences.

Example 2—In Vitro Testing

Previous attempts to modify the intein cleaving reaction and controllability through modifications to the body of the mini-intein ΔI-CM have been unsuccessful and generally lead to inactive inteins or inteins with very slow cleaving rates. For this reason, the focus of the disclosed inteins was on the sequence immediately preceding the N-terminus of the intein to generate a zinc-binding motif that includes the critical Histidine residue required for cleaving. This was done by appending the computationally designed sequences to the N-terminus of the mini intein ΔI-CM.

Figure 4:
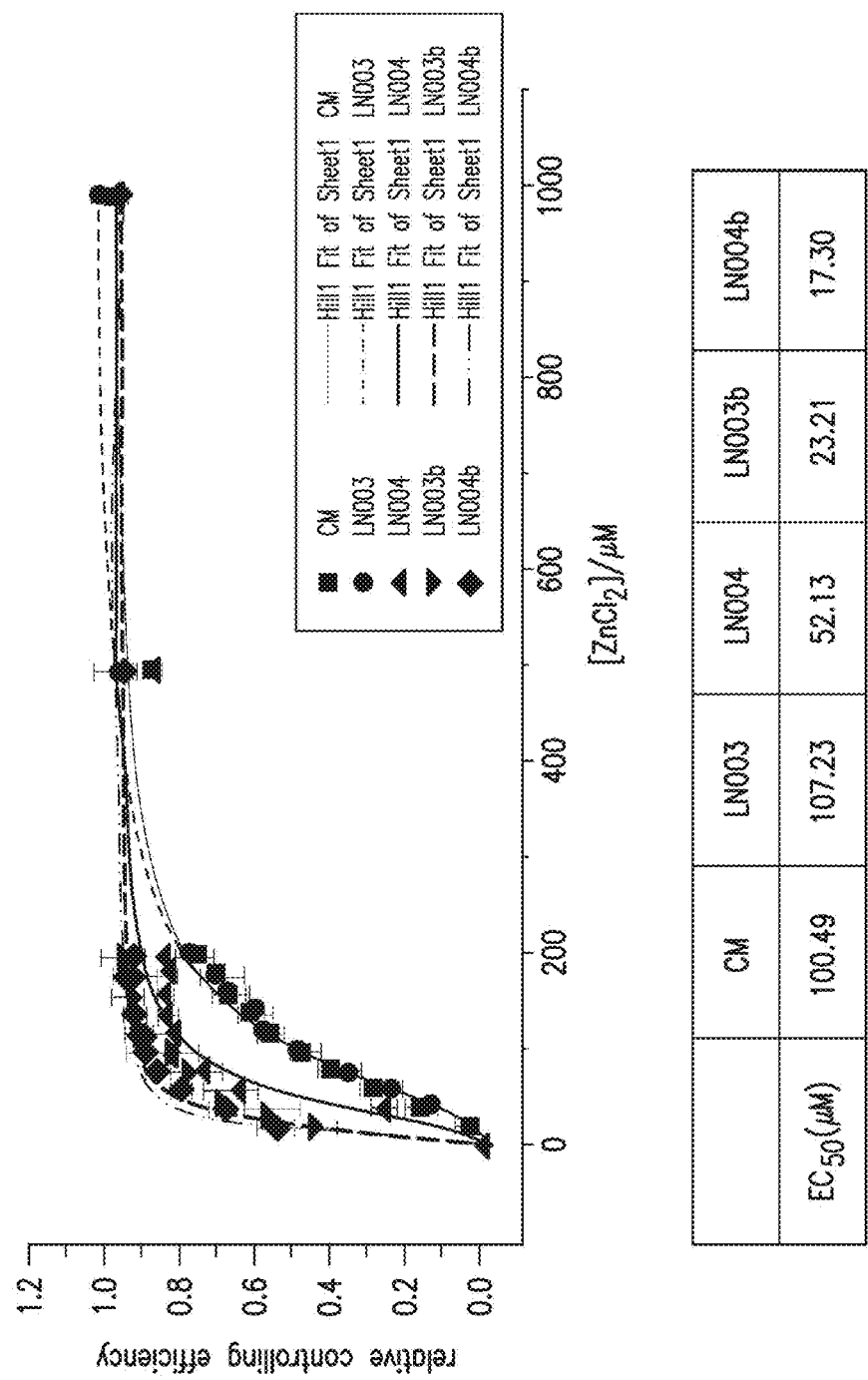
FIG. 4 shows the chemical control of intein cleavage. The zinc concentration required to decrease the cleavage rate by 50% decreased from 100 μM in the ΔI-CM intein to 17 μM in the LN-004b intein is shown. Thus, the concentration of zinc required to fully suppress intein cleaving also decreased by a factor of approximately 10 (from about 600 μM to less than 100 μM). This change allows the safe use of zinc to suppress intein cleaving in CHO cell culture because CHO cells can easily tolerate 100 μM zinc but suffer at 600 μM zinc.
Figure 5A:
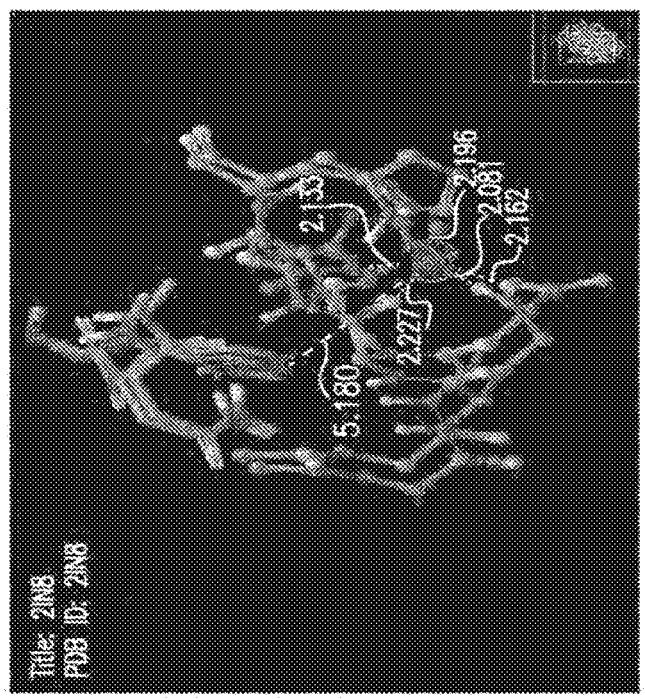
FIGS. 5A-F show Schrodinger Q-SITE and Impact structures of exemplary ZBMs that included the zinc metal ion and the amino acid side chain, separated from the molecular modeling region using hydrogen caps between the alpha and beta carbons. The simulations were run with and without a metal center to look for structures that are able to tightly bind to zinc ion in a way that the bound zinc will sequester the critical conserved histidine residue of the active site. The structures represented a range of conformations, all of which had potential to inhibit the intein active site upon zinc-binding. A) The top two sequences are SEQ ID NO:45. The bottom sequence is SEQ ID NO:46. B) The top sequence is SEQ ID NO:47. The bottom sequence is SEQ ID NO:46. C) The top two sequences are SEQ ID NO:45. The bottom sequence is SEQ ID NO:46. D) The top two sequences are SEQ ID NO:48. The bottom sequence is SEQ ID NO:46. E) The top sequence is SEQ ID NO:49. The bottom sequence is SEQ ID NO:46. F) The top two sequences are SEQ ID NO:50. The bottom sequence is SEQ ID NO:46.
Figure 5B:
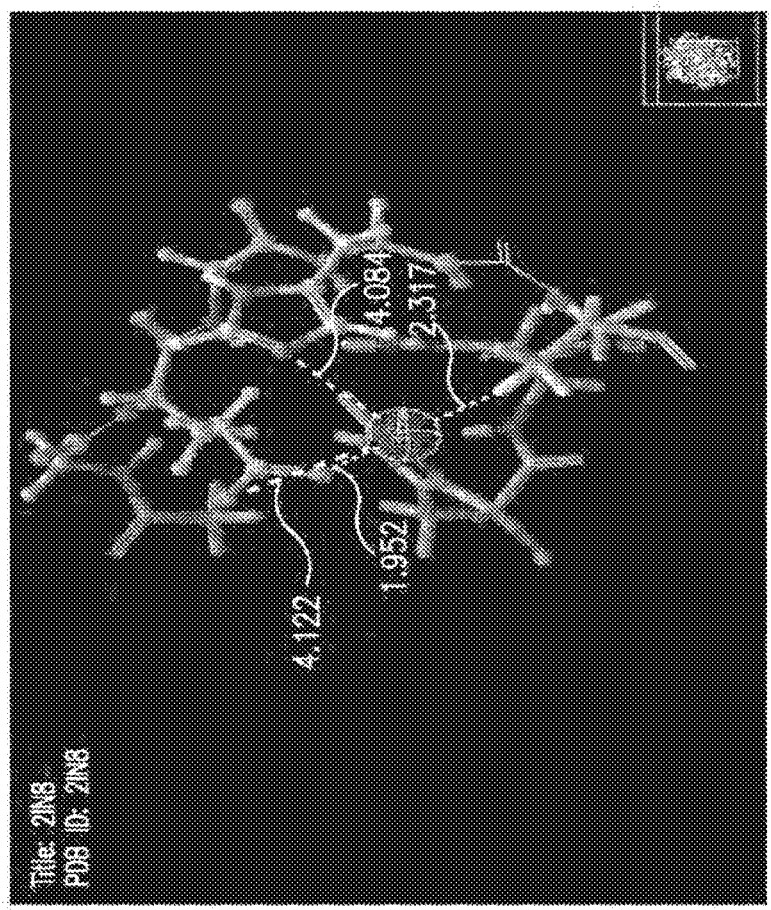
Figure 5C:
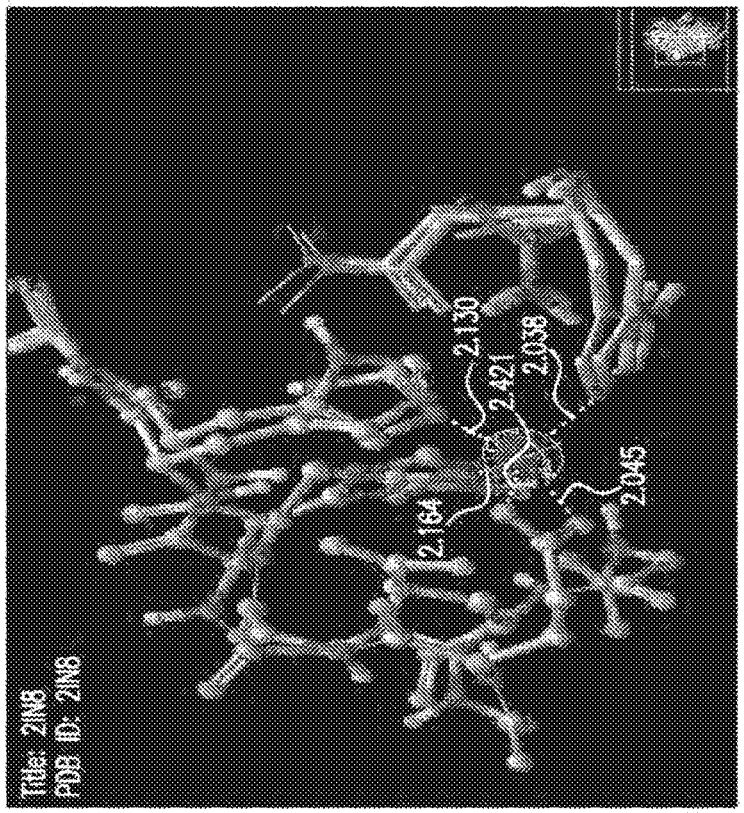
Figure 5D:
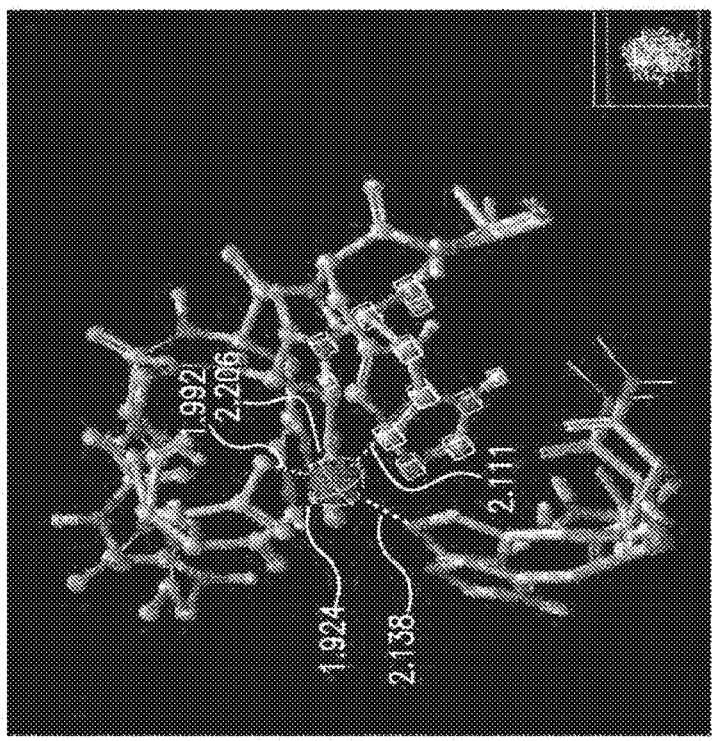
Figure 5E:
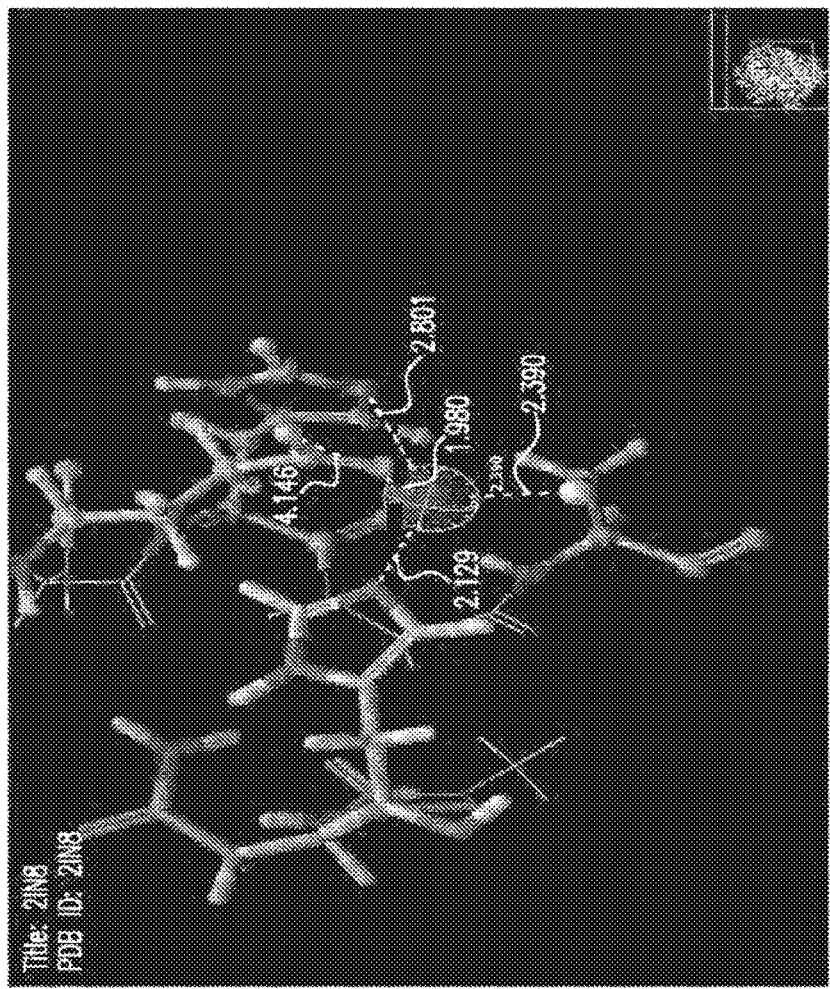
Figure 5F:
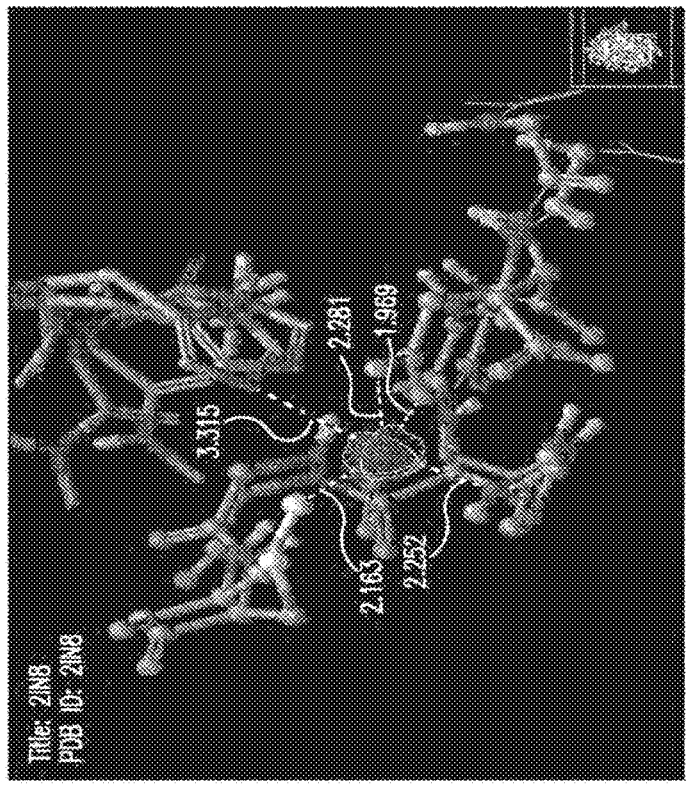

Several putative inteins were designed. Once tested, the most promising design was determined to be an intein that was denoted as LN-004b, for experimental purposes. This intein has a much stronger affinity for zinc than the original ΔI-CM intein, and the presence of zinc substantially suppressed the cleaving reaction, as shown in FIG. 4.

After extensive testing, it was determined that the zinc concentration required to decrease the cleaving rate by 50% had decreased from 100 μM in the ΔI-CM intein to 17 μM in the LN-004b intein. Thus, the concentration of zinc required to fully suppress intein cleaving also decreased by a factor of approximately 10 (from about 600 μM in FIG. 4 to less than 100 μM). This change allows the safe use of zinc to suppress intein cleaving in CHO cell culture because CHO cells can easily tolerate 100 μM zinc, but suffer at 600 μM zinc.

Example 3

Therapeutic proteins are currently produced in large manufacturing plants using in vitro cell culture, where recombinant cells are grown over multiple days or weeks in >1,000 liter bioreactors. The bioreactors are then harvested and the expressed proteins are recovered, purified, stabilized, and stored as an intermediate bulk drug substance. The drug substance is then formulated, filled into delivery devices and released by a quality assurance organization before shipment to a distribution warehouse for future delivery to the point-of-care. This is an enormously expensive, time consuming, and complex undertaking that takes months to execute. If starting from scratch, process development activities for a single therapeutic would ordinarily require 6 to 8 years per project to complete all of the characterization, process monitoring and validation activities, needed to meet regulatory authority approval. While companies continue to develop in vivo expression platforms for the manufacturing of proteins, there are no systems designed for the flexibility across proteins or the speed necessary for the rapid development of purification methods for arbitrary target proteins to be used in patient therapies. A novel mammalian in vitro protein expression technology and innovative purification technologies combined with advances in microfluidics and microelectronics to produce biologics on site can be used. Specifically, following technologies can be enhanced and integrated:

Protein Expression: Expression of the protein of interest can be made possible with a mammalian cell-free extract similar to the product currently commercialized by Thermo Scientific based on HeLa cell extracts. The Thermo Scientific 1-Step Human High-Yield In Vitro Translation (IVT) is a cell-free protein expression system that provides all of the essential components required for transcription and translation. The kits are optimized with Accessory Proteins and Reaction Mixes that support protein synthesis for up to 24 hours using a DNA template. The 1-Step Human High-Yield IVT Kits, with a continuous-feed device, enable the expression of functional proteins. The current system uses modified HeLa cell extracts to take advantage of the robust human translation machinery and generate functional full length proteins. The advantages of using the 1-Step Thermo High-Yield IVT Kits over traditional in vivo expression systems include (1) the ability to express toxic or insoluble proteins, (2) easily perform protein labeling with modified amino-acids, (3) reduce the time and cost of expressing human proteins in tissue culture cells, (4) 10 to 100 times greater expression than other mammalian IVT expression systems that are based on rabbit reticulocyte lysates, ability to carry out (5) post translational modifications (PTMs) including phosphorylation, and (6) lot-to-lot consistency as a cell culture based product. In this system, protein expression is performed in a proprietary mini dialysis device that allows a continuous supply of nucleotides, amino acids and energy generating substrates into the reaction while removing inhibitors of proteins synthesis.

Purification: A purification process platform can consist of two basic steps: (1) an affinity capture of the target protein and (2) a subsequent polishing step which the impurities present in the eluted product from the affinity step can be reduced to an acceptable level. The affinity capture step can be the use of a fusion product comprising an affinity tag, a self-cleaving intein, and a therapeutic target protein. This fusion is initially adsorbed onto a chromatography column and washed of impurities, after which the target protein is eluted by pH-induced self-cleavage of the intein-affinity tag. For the polishing step the use of membrane chromatography columns incorporating either conventional or mixed mode ligands used together with novel elution conditions can be used. The self-cleaving affinity tag used together with a suitable polishing step in this system represents a new platform for the purification of non-antibody proteins. A platform of this type has never been applied to general recombinant therapeutic proteins.

The intein purification method allows a product to be recovered directly from a cell free reactor and produce a purified therapeutic protein of interest in a form suitable for parenteral administration at a high product yield.

Figure 1:
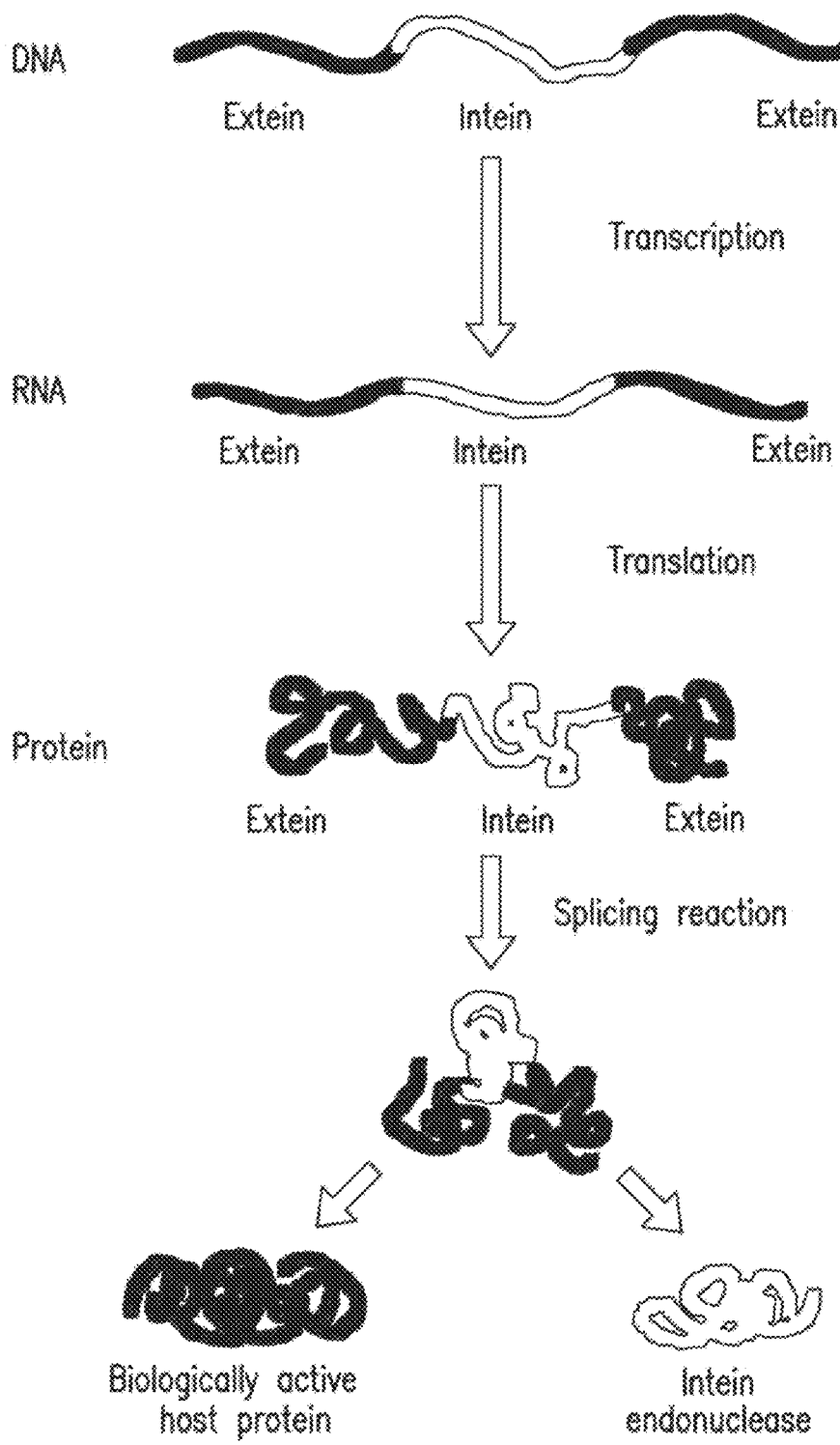
FIG. 1 shows natural intein function. Native inteins remove themselves from within host proteins in a self-splicing reaction.
Figure 2:
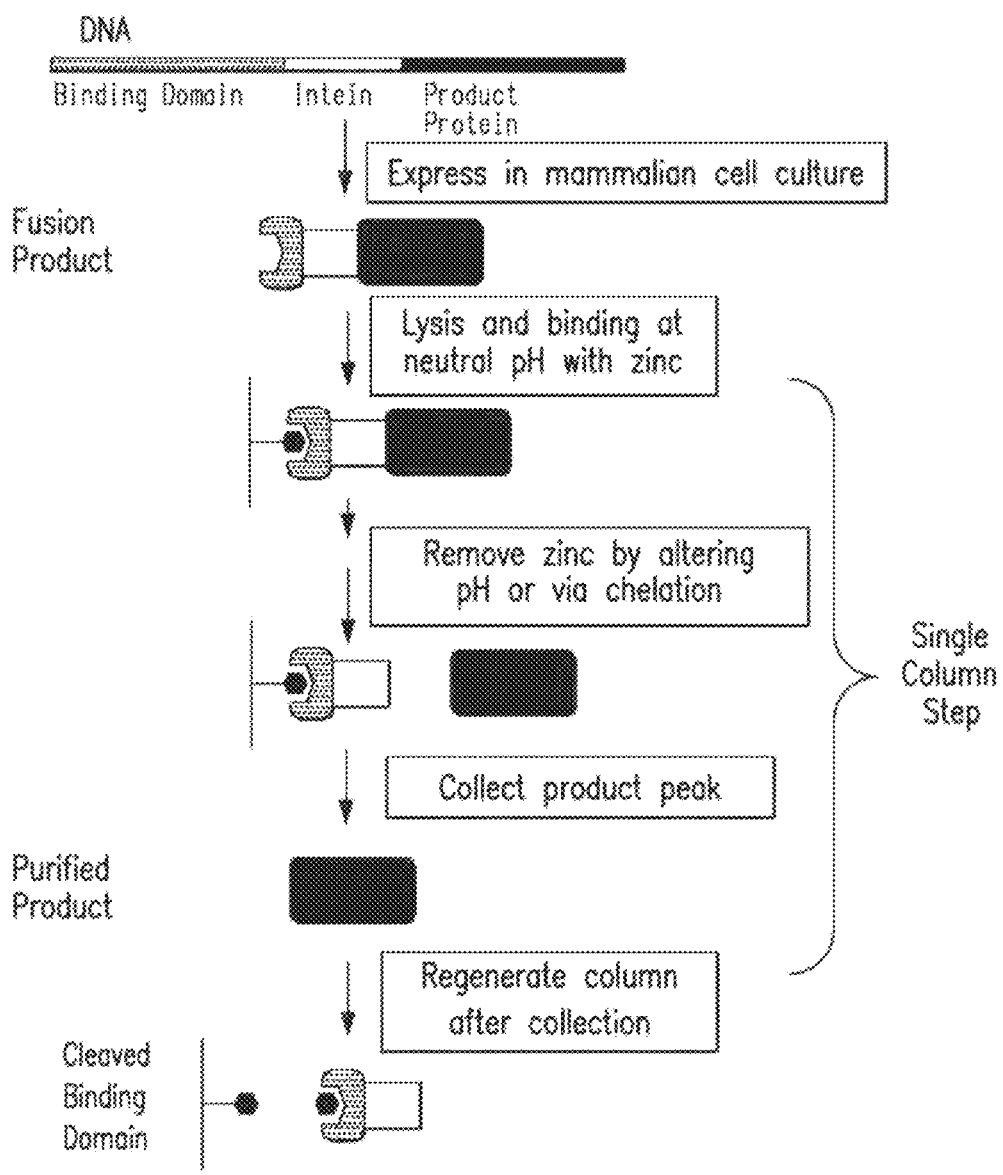
FIG. 2 shows a self-cleaving affinity tag method. The inteins or CIPSs disclosed herein can allow for efficient, single-column purification of target proteins by providing an effective means for tag self-cleaving.

Development of Capture Methods Using an Intein Fusion Product:

In order to accomplish the intein-based affinity capture method proposed here, gene fusions can be constructed using conventional PCR cloning methods. The fusions can include different combinations of affinity tag, self-cleaving intein and target protein. The basic strategy for the intein based method is shown in FIG. 2. Three initial tags can be evaluated, including the chitin-binding domain (CBD), an Fc domain, and a quaternary amine binding protein. The CBD tag has been chosen due to its small size and proven track record with intein technologies, as well as its strong binding to its corresponding ligand. These characteristics provide very high purification factors with this tag, along with minimal impacts on overall expression. A disadvantage of this tag is that no pre-validated affinity resins are available, and the binding capacity of available resins is somewhat low. The Fc domain tag has been selected due to its small size, tight binding, and potential to bind to conventional Protein A affinity chromatography resin. Because Protein A resins are the current industry standard for producing therapeutic antibodies, they have an extensive track record with the FDA and are easily validated. Further, available Protein A resins have extremely high binding capacities (50 milligrams of IgG antibody per milliliter of bed volume) and can be regenerated over 100 times. This combination of characteristics indicates that Protein A resins can be optimal for the proposed device, as they will be both durable and highly productive in a relatively small volume. Disadvantages for Protein A are that they have not yet been evaluated with intein technologies, and it is not clear which Fc domain will be appropriate for this application. Finally, a novel affinity tag with highly specific binding to quaternary amines can be investigated. These amines are very commonly used in conventional chromatography resins used in the biopharmaceutical industry, and are readily available in a pre-validated form (e.g., Q-Sepharose). Non-specific binding is a concern due to the charged nature of these resins, but a properly designed purification method may actually capitalize on this aspect to enhance the intein-mediated purification step with some ion-exchange character. These tags can be combined with a variety of self-cleaving intein modules, each selected for high controllability that is appropriate to the expression system. The base case inteins can be the previously reported ΔI-CM and ΔI-SM inteins, which are tightly controlled by a combination of pH and temperature. These inteins can have sufficient control to allow a highly effective purification of the target proteins with one of the three aforementioned affinity tags. The development of more rapidly cleaving and controllable inteins is also being investigated.

Evaluations of the intein performance can rely on small-scale expression and quantification using conventional assays. As stated above, particular attention can be paid to expression level (productivity), premature cleaving and cleaving efficiency during purification (yield), and purity. Assessments can be made using SDS-PAGE for early experiments, and HPLC during later optimization. Final assessments can include specific activity assays and more advanced bioequivalence assays.

Ultimately, a combination of tag and intein can be selected for each target protein such that expression, cleaving and purity are maximized for downstream polishing. Based on previous work, there is potential to acquire greater than 80% yield in the intein-based affinity steps, which combine initial capture and rough purification of the initial target. Specific minimal performance metrics can be determined for each therapeutic target protein, and the optimal designs can be incorporated into the device DNA and methodology libraries.

Example 4

Background and Significance

The importance of highly purified biopharmaceutical proteins and enzymes cannot be overstated. Well-known blockbuster examples from industry include Remicade® for the treatment of Rheumatoid Arthritis (RA), Avastin® for metastatic cancers, Rituxan® for RA and Non-Hodgkin's Lymphoma, and dozens of other lifesaving recombinant antibodies and glycoproteins. Although some progress has been made in the expression of glycoproteins in microbial and yeast hosts, the vast majority of complex biopharmaceutical glycoproteins are still expressed in mammalian cell culture, where the most commonly used host is Chinese Hamster Ovary (CHO) cells. Further, dramatic increases in mammalian cell culture productivity, due to newly engineered cell lines and well-designed fed-batch processes, are making CHO and other hosts highly efficient for glycoprotein production at both laboratory and manufacturing scales. Monoclonal antibodies, which make up a large percentage of biologics, can be purified using the Protein A affinity platform, but increasingly important non-antibody glycoproteins cannot. These proteins require individual methods to be developed (FIG. 27A), which can slow the discovery and development of new therapeutics, while increasing their eventual costs. These developments have shifted research and manufacturing bottlenecks to protein purification, and have thus created an urgent need for reliable platform methods to purify new glycoproteins from mammalian cell culture. This study creates the first generally applicable self-cleaving tag purification platform for proteins expressed in mammalian cell culture, and particularly for those proteins that cannot be purified with existing Protein A pla (FIG. 27B) tform methods. This platform can enable the rapid and inexpensive development of therapeutics at all scales. As such, it can have a critical impact on accessibility to personalized medicine, where small patient populations require development costs to be minimized. These methods can also enable high-throughput proteomic studies, which can accelerate the development of new pharmaceuticals. Moreover, the ability of this system to work with any given tag can facilitate the development of disposable technologies, which are becoming increasingly attractive for next generation multiproduct biopharmaceutical manufacturing facilities. Overall, this work can play a key role in the highly active field of high-capacity and low cost process development.

Figures 6A, 6B:
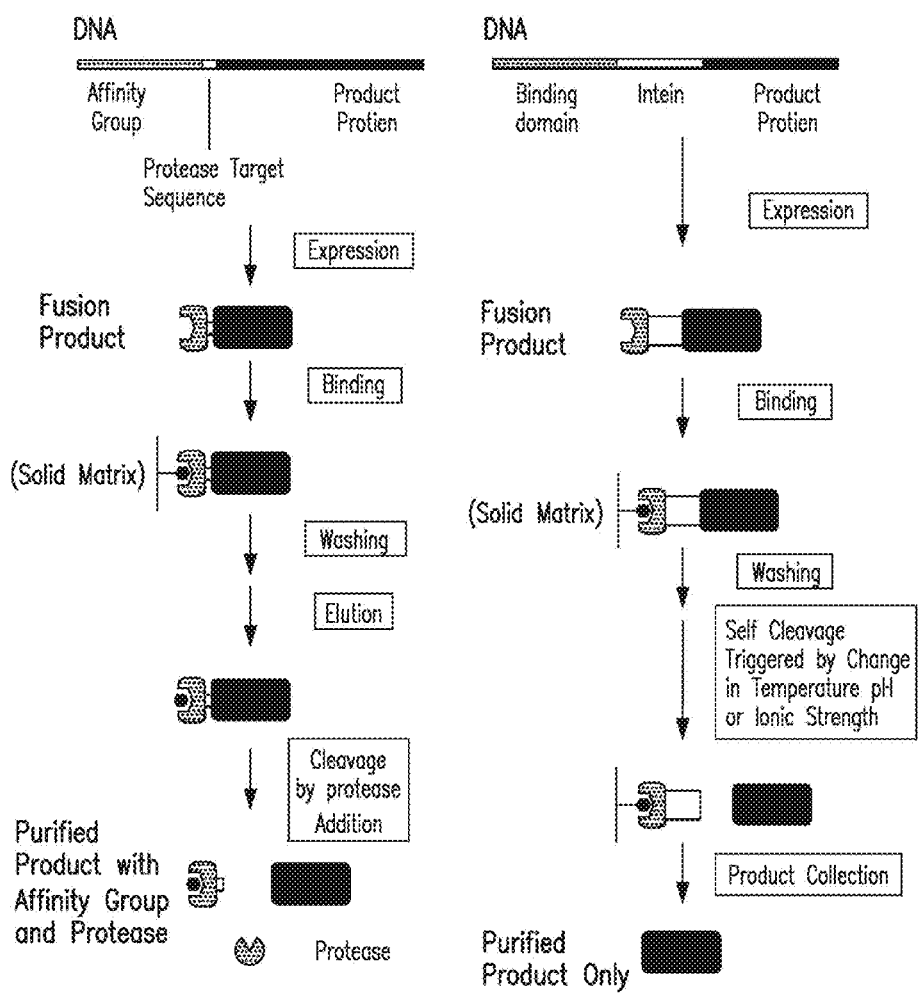
FIGS. 6A and 6B show the Affinity Fusion Technologies. (A) Conventional method (left) requires protease treatment to remove the affinity tag from the purified fusion protein. Subsequent purification is required to remove the protease and cleaved tag. (B) Inteins (right) allow self-cleaving of the affinity tag, providing a pure product in a single column step.

This approach is modeled after conventional affinity tag methods used ubiquitously in microbial recombinant protein expression. In this method, an easily purified affinity tag is genetically fused to the target protein to facilitate its purification (FIG. 6A). The purification method is then based entirely on the tag, and requires no target-dependent optimization, allowing virtually any target protein to be purified through a single, universal procedure. Thus, these methods lend themselves to the development of platform and high-throughput processes, and are potentially very appealing to the pharmaceutical industry. Commonly used tags include the maltose binding protein (MBP), glutathione S-transferase (GST), chitin binding protein (CBP), and the highly popular poly-histidine tag (His6). Each of these tags binds to its commercially available cognate affinity resin, allowing target proteins fused to the tag to be purified using a single, pre-optimized procedure. Although these methods are highly effective at laboratory scale, and are used in academic, government and industrial laboratories worldwide, they are never used in biopharmaceutical manufacturing, and are rarely used to purify products expressed in mammalian cell culture. This is primarily due to the potential immunogenicity of the tags, and the expense associated with removing them at multi-kilogram scale. In particular, the highly specific endopeptidases used for tag removal can add several thousand dollars per gram of purified target protein to their production cost, making these methods cost-prohibitive at even small biopharmaceutical manufacturing scales.

This study seeks to enable the use of tag methods for biopharmaceutical production by generating effective self-cleaving protein modules that can uniquely be used in mammalian cell culture (FIG. 6B). This controllable module can induce any conventional purification tag to self-cleave in response to a simple and innocuous process change (e.g., pH, temperature or ligand addition), allowing highly efficient tag removal at minimal expense. An important aspect of the proposed module is that its mechanism ensures precise cleavage of the target protein, so that unwanted or aberrant cleaving is impossible. The significance of this technology is evident from the number of self-cleaving modules that have been developed in the past several years. Each of these methods exhibits a variety of advantages and disadvantages, and unfortunately, none of them are universally applicable to mammalian cell culture products. Among the most significant disadvantages for many of these modules is a requirement for modification of the target protein amino acid sequence (Table 3, *Neisseria meningitides* FrpC protein, *Staph aureus* Sortase A transpeptidase, and *Vibrio cholerae* MARTX domain). These modifications are potentially immunogenic for therapeutic proteins, and can also interfere with protein activities in basic studies. The Classical Swine Fever Virus Npro Module requires a refolding procedure to induce cleaving, making this method impractical for mammalian cell culture as well. Two notable self-cleaving modules in this group belong to the commercially available IMPACT and IMPACTCN systems. These modules, currently marketed by New England Biolabs, are based on a naturally occurring self-splicing protein called an intein. These modified inteins have been combined with a chitin binding protein and chitin resin, and are induced to self-cleave at their N-terminus by addition of thiol compounds (e.g., dithiothreitol, 2-mercaptoethanol or 2-mercaptoethane sulfonate). In this case, the thiol compound chemically breaks a thioester intermediate bond between the target protein and tag, releasing the target protein from the intein and column-bound chitin binding tag. In the IMPACT-CN system, the peptide bonds at the N and C-termini of the intein are simultaneously induced to cleave by thiol addition. Unfortunately, disulfide bonds in antibodies and other therapeutic proteins are chemically similar to this labile thioester, causing them to also be broken by the IMPACT cleaving agent. This limitation effectively prevents the IMPACT system from being used with proteins containing disulfide bonds, which include all recombinant antibodies and a large majority of antibody fragments and other biologics currently in development. For these reasons, a controllable self-cleaving module with general applicability in eukaryotic host cells has yet to be found.

TABLE 3

Summary existing self-cleaving modules and relative advantages and disadvantages

| Cleaving Method | Cleaving Trigger | Primary Advantages | Primary Disadvantages |
| --- | --- | --- | --- |
| Conventional Protease | Protease Enzyme Addition, incubation conditions depend on protease used. | Well-established, with many optimized options available. No premature cleaving. | Expensive. Can require target modification. Can cleave target unexpectedly. Cleaving rate unpredictable. |
| N-cleaving intein (IMPACT ® System) | Thiol compounds at 30 to 100 mM. Incubation at 4° C. to 37° C. for 2 hr to O/N. | Most commonly used, commercially available. Very little premature cleaving. Good low temp cleaving rate. | Requires high concentrations of thiol compounds for cleaving. Breaks disulfide bonds in target. Expensive at large scale. |

TABLE 3-continued

Summary existing self-cleaving modules and relative advantages and disadvantages

| Cleaving Method | Cleaving Trigger | Primary Advantages | Primary Disadvantages |
| --- | --- | --- | --- |
| C-cleaving intein (This proposal) | pH below 7.0, incubation at room temp to 37° C., 4 to 24 hr. | Safe for most proteins. Most inexpensive and flexible cleaving trigger. Tag can aid solubility. | Substantial premature cleaving in vivo during expression. Slow cleaving at low temp. Cannot be used in CHO cells. |
| N + C cleaving intein (IMPACT-CN ® System) | Same as N-cleaving inteins. | Most commonly used, commercially available. Very little premature cleaving. | Requires high concentrations of thiol compounds for cleaving. Breaks disulfide bonds in target. Expensive at large scale. Requires dialysis after cleaving. |
| *Neisseria meningitides* FrpC protein (N-cleaving) | 10 mM $Ca^{2+}$, 4° C. to 37° C., 4 to 8 hr (higher temperatures accelerate cleaving) | Very little premature cleaving during expression. Fast cleaving upon $Ca^{2+}$ addition. | Requires addition of Asp residue to C-terminus of target protein. May require EDTA and DTT in purification buffers. |
| *Staph aureus* Sortase A transpeptidase (C-cleaving) | 5 mM $Ca^{2+}$, 10 mM Gly3, incubation at 25° C. for 4 to 6 hours. | Fast cleaving. Cleaving module appears to increase solubility of target protein. | Requires addition of Gly residue to N-terminus of target protein. Some premature cleaving. Unwanted cleaving in target (?). |
| *Vibrio cholerae* MARTX domain (N-cleaving) | 50-100 mM inositol hexakisphosphate ($InsP_6$), 4° C. to room temp for 1 to 2 hr. | Fast cleaving. Cleaving module appears to increase solubility of target increase solubility of target protein. | Requires 1 to 4 a.a. to be added to C-terminus of target protein. Small potential for unwanted cleaving in target. |
| Classical Swine Fever Virus $N^{pro}$ Module | In vitro refolding of fusion protein under kosmotropic conditions. | High-level expression. Protects target from protease. Good for toxic targets. Native target N-terminus. | Efficient refolding procedure for target must be available. |

The disclosed research effort has been the development of self-cleaving purification tags based on C-terminal cleaving inteins (FIG. 6B). These inteins are distinct from the N-terminal cleaving inteins of the IMPACT systems in that they are triggered to cleave by changes in pH and temperature alone, and most importantly, do not require thiol agents to induce thioester cleavage. These inteins are also capable of delivering a target protein without any additional amino acids on the N-terminus, allowing the production of fully native products. Further, the cleavage mechanism ensures that the cleavage reaction is strictly limited to the peptide bond immediately following the final conserved Asn residue of the intein. These aspects make C-terminal cleaving inteins uniquely attractive as a starting point for the development of self-cleaving tags that can be used with complex products produced in mammalian cell culture. The initial efforts produced an engineered mini-intein domain that cleaves cleanly at its C-terminus in response to a mild change in pH and/or temperature. This self-cleaving intein domain has been combined with a number of conventional and new nonchromatographic tags to create a set of powerful new methods for the purification of proteins expressed in *E. coli*.

Figure 7:
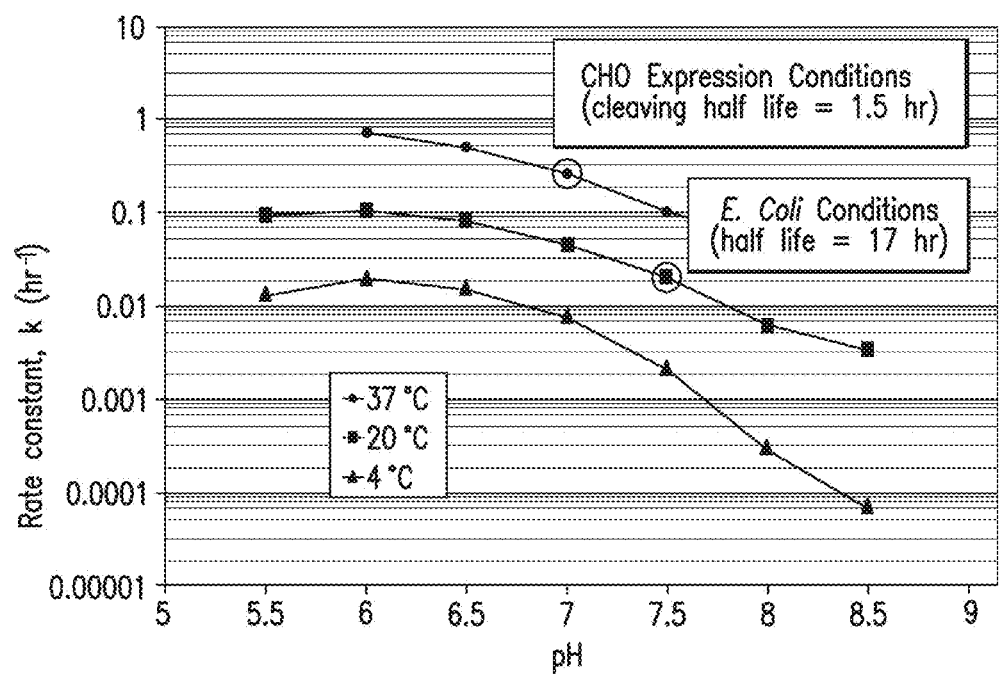
FIG. 7 shows the comparison of conditions experienced by proteins expressed in E. coli and CHO relative to the expected cleaving rate of the intein module. Rapid cleaving under CHO cell culture conditions leads to unacceptable levels of premature cleaving during expression in vivo.

Intein-tag fusion proteins have been expressed in CHO cells and *Pichia pastoris*. However, a major obstacle has become premature cleaving of the target protein during expression, which substantially decreases final yields of purified target. This is due to the fact that the cleaving reaction is solely dependent on pH and temperature. This dependence has been an asset in microbial expression hosts, but has become a liability when applying these systems to mammalian cell culture (FIG. 7). The primary difference between microbial and mammalian expression systems is that the intein cleavage rate is slow under conditions experienced in microbial expression, while microbial expression rates are high. Conversely, the intein cleavage rate is rapid under conditions experienced in mammalian cell culture, while mammalian expression rates are lower. This difference allows an uncleaved target protein to be purified from *E. coli*, but leads to substantial premature cleaving of the target protein before purification in mammalian hosts. This critical difference effectively prevents currently available self-cleaving tags from being applied to the production of therapeutic glycoproteins produced in mammalian hosts. This shortcoming is intrinsic to the cleaving mechanism of the intein, and thus is not trivial to overcome. Indeed, the development of a CHO-capable intein system has stymied several academic and industrial laboratories over the past decade. The disclosed approach combines rational protein engineering and directed evolution to create a next generation intein platform for the purification for complex biopharmaceutical glycoproteins at laboratory and manufacturing scales.

Potentially Transformative Aspects

The impact of this work is indicated by the success of two existing related technologies. The first is the use of conventional affinity tags in laboratories throughout the world for the purification of recombinant proteins expressed in microbial hosts. These methods have changed the way molecular biology is studied, and have impacted the development of countless therapeutic proteins on the market today. The second is the universal application of Protein A affinity methods to the manufacture and study of recombinant antibodies produced in mammalian cell culture. The popularity of this expensive, yet powerful method for antibody purification illustrates the appeal of simple affinity methods for the purification of mammalian cell culture products.

However, Protein A affinity methods cannot be applied to non-antibody products, and conventional affinity tag methods have yet to penetrate mammalian cell culture processes. Thus, the disclosed work lies at the intersection of these two technologies. It seeks to provide a new platform method, with the compelling appeal of Protein A for purification, but with the universal applicability of conventional microbial affinity tags for virtually any target. The resulting methods can have a similar impact to the now ubiquitous affinity tags used in microbial expression, but applied to the production of complex glycoproteins in mammalian and other eukaryotic hosts.

Development of Self-Cleaving Tags for Mammalian Cell Culture Applications Overall Approach:

Rational active-site redesign can be combined with a yeast display-based evolutionary approach to develop a highly controllable self-cleaving intein for mammalian cell expression systems. This is a deviation from previously published approaches, which have relied on random mutagenesis with in vivo genetic selections for controlled intein cleaving. A critical shortcoming of these previous approaches is that direct selections for inteins sensitive to metal ions, small-molecule ligands, pH changes, strong temperature shifts, or any non-physiological condition, are impossible because these conditions cannot generally be manipulated inside a growing cell. Further, the use of random mutagenesis greatly decreases the probability that critical combinations of mutations will ever be observed. Thus, the disclosed approach derives from the specific focus on residues and structural features that are known to be critical to intein cleaving function, and from the selection of the resulting mutants in a fully flexible in vitro environment. This strategy can generate optimized mutant inteins, designed to be stable and uncleaved at the physiological conditions of a desired expression host, but that cleave rapidly under convenient downstream process conditions in vitro.

Figures 8A, 8B:
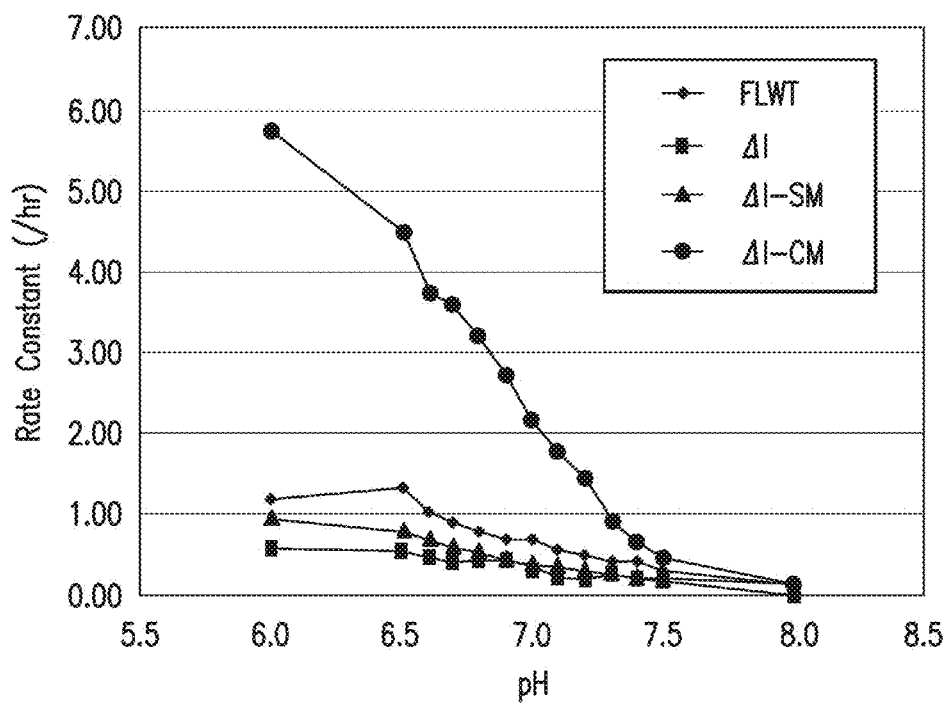
FIGS. 8A, 8B, and 8C show evidence that the penultimate histidine residue of the AI-CM intein plays a critical role in regulating the C-terminal cleaving reaction. (A) Protein sequence alignment of seven canonical inteins, showing the high degree of conservation of the penultimate histidine residue. SEQ ID NOs:51-64 are present in FIG. 8A. The sequences read from left to right and top to bottom. (B) The cleavage rate versus pH curve for the C-terminal cleaving reactions of several representative inteins, showing similarity to the pKa curve for the histidine side chain. (C) Extended position of the penultimate histidine (shown in ball-and-stick) in the ΔICM crystal structure.
Figure 8C:
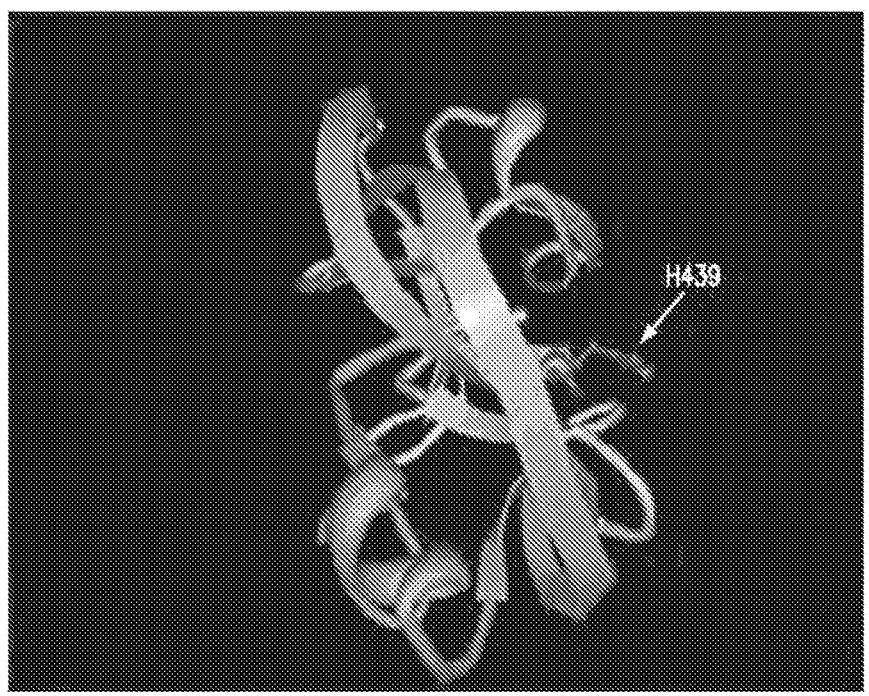

Introduction of engineered metal binding sites into the intein active center. Several lines of evidence indicate that intein cleavage can be controlled through the introduction of a metal binding site into the intein active center (FIG. 8). The first is that intein splicing domains end with a highly conserved histidine-asparagine dipeptide at their C-terminus (H439/N440 in previously developed ΔI-CM intein; FIG. 8A). Cyclization of the C-terminal asparagine to form a succinimide ring cleaves the C-terminal peptide bond during the self-cleaving reaction, releasing the fused target protein. Plots of intein cleavage rates versus pH closely resemble that of the pKa curve for the histidine side chain (pKa ~7.2), indicating that the protonation state of the highly conserved penultimate histidine residue can be critical for activation of intein cleaving (FIG. 8B). This is further supported by molecular simulations. Further, previous observations have shown that high concentrations of zinc ion can inhibit intein splicing and cleaving, indicating that this histidine residue is positioned to weakly bind divalent ions, and that binding can inhibit the cleaving reaction. Finally, crystallographic data indicate that the penultimate histidine residue of the previously developed ΔI-CM intein exists in an extended configuration, further indicating that this residue can be a target for allosteric intein control through metal binding (FIG. 8C). Based on these observations, a set of inteins with augmented metal binding sites can be assembled.

Figure 9:
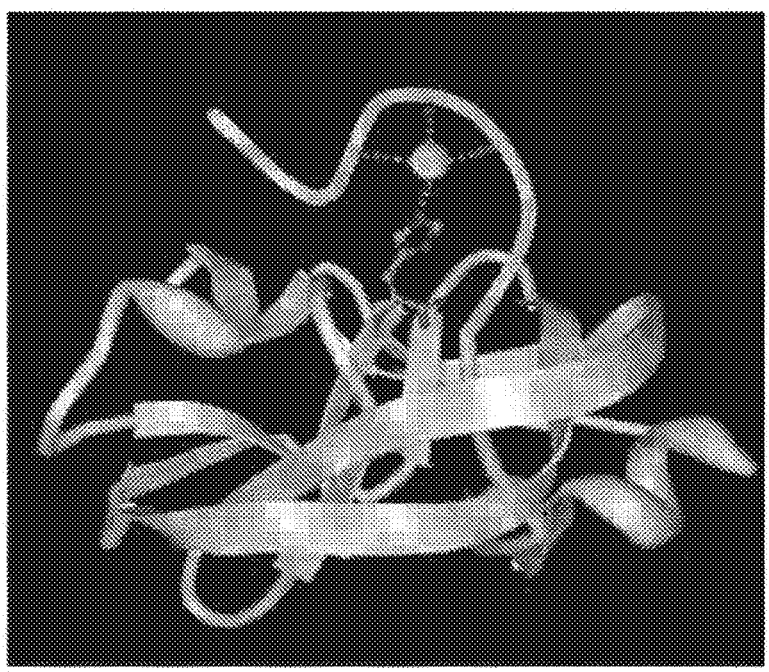
FIG. 9 shows the strategy for grafting a metal-binding motif (shown schematically in yellow) to the N-terminus of the mini-intein. The site is designed to sequester the catalytic H439 side chain.

Histidine residues H429 and H439 of the ΔI-CM mini intein (residue numbering is relative to the full-length Mtu RecA intein) are critical to the intein active site. A metal binding site that includes one or both of these residues could sequester the enzymatically active imidazole nitrogens and prevent their interactions with N440, thus interfering with the cleaving reaction. The Synechocystis sp. PCC6803 DnaE intein and the Mtu RecA intein splicing activities are naturally and reversibly inhibited by as little as 2 mM divalent zinc. A crystal structure of a minimized Mtu RecA splicing intein, in complex with divalent zinc, showed cross-protein metal binding interactions with active site residues H429, H439, E424, and the cyclized N440 succinimide (Protein Data Bank: 2IMZ). Interaction of a cleaving intein mutant alone in free solution with $Zn_{2+}$ was studied using isothermal titration calorimetry. The binding constant for zinc was reported to be 6.8 nM, and likely involves specific metal coordination to H429 and H438. Unfortunately, this naturally occurring zinc binding site recruits ligands from two intein molecules aligned in a dimer within the protein crystal structure. Inteins with a fused N-terminal affinity tag and a C-terminal target protein fail to form this dimer structure and bind zinc efficiently, and thus fail to be inhibited. It is this binding site that can be augmented through protein engineering. In particular, an additional peptide segment with several metal coordinating side chains can be appended onto the N-terminus of the intein sequence, thus taking advantage of the proximity of the N and C-termini of the intein to "graft" on a new metal binding center that includes critical residues of the intein active site (FIG. 9). Critically, this strategy does not interfere with the specific amino acids involved in the cleaving reaction, thereby maintaining the ability of the intein to release a native target protein after cleaving. Finally, release of the bound zinc, either by EDTA chelation or pH shift, can restore the histidine residues to their unbound state, thus allosterically activating the intein cleaving reaction.

Results

Figure 10A:
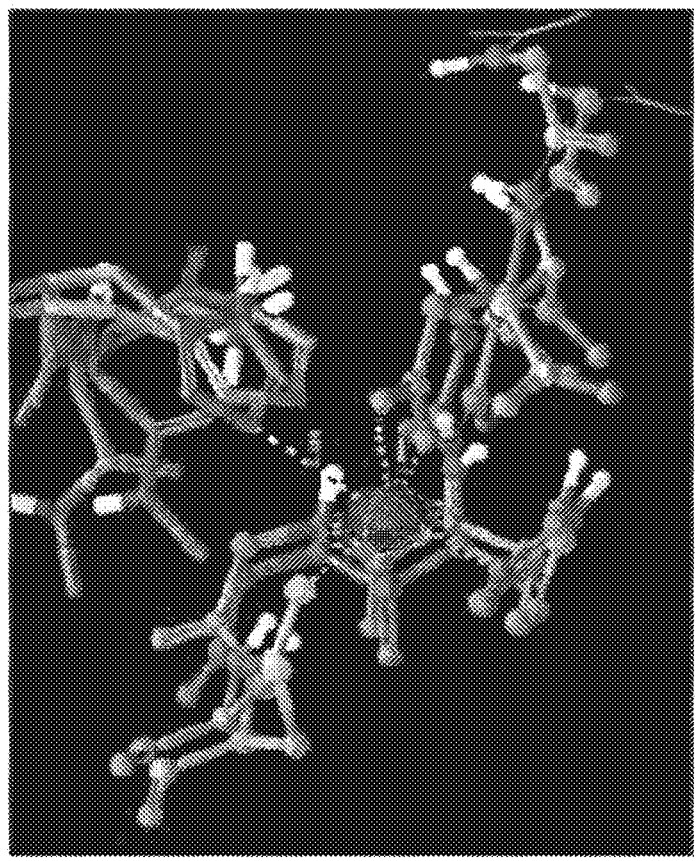
FIGS. 10A and 10B show the design and zinc binding characterization of the of the LN-004b intein mutant. A)
Figure 10B:
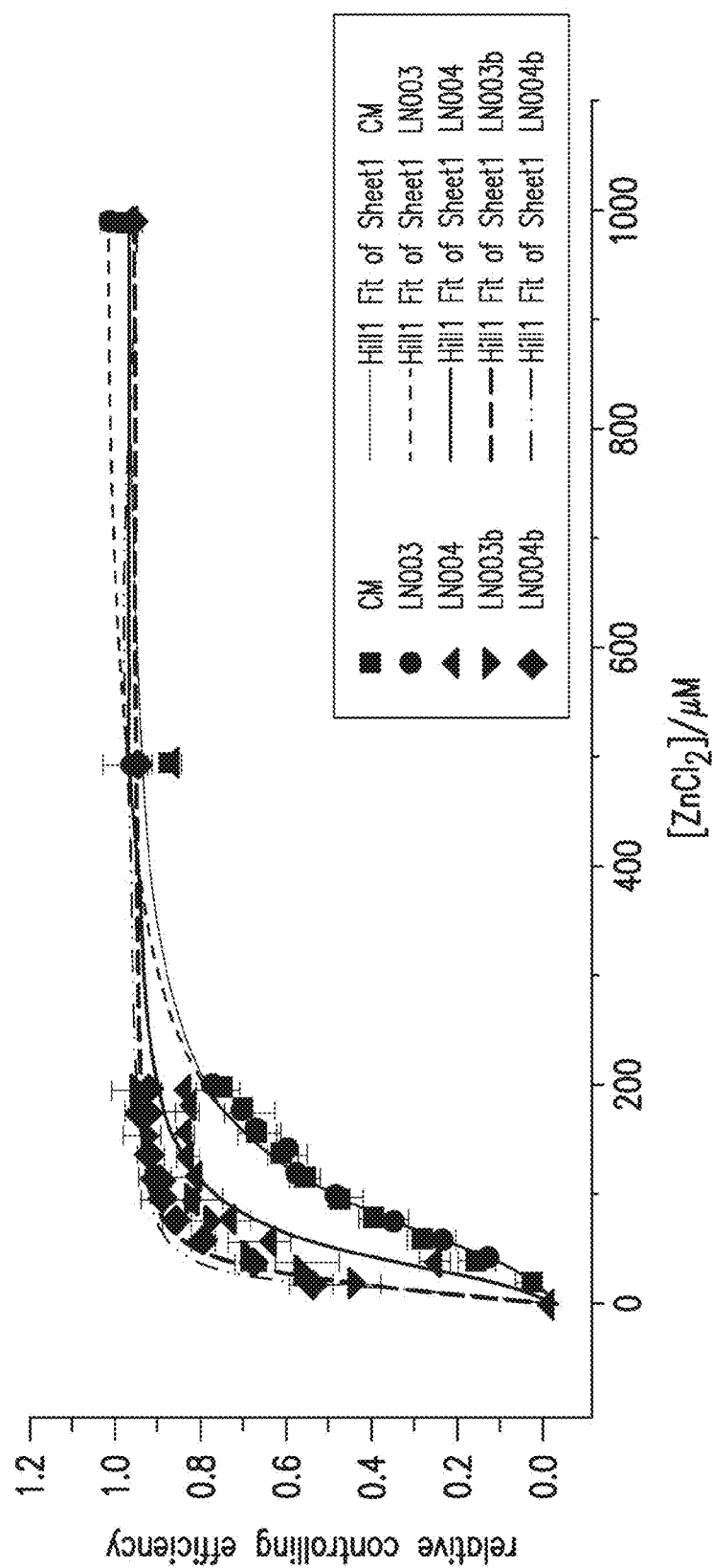

Rational protein design methods in conjunction with traditional template-driven PCR methods have been used to construct six Mtu RecA mutants in which divalent zinc binding sites recruit at least one critical active site residue. In each case, six or eight amino acids were added to the N-terminus of the intein to introduce the new metal-binding site. Once constructed, these engineered mutants were expressed in E. coli host cells for initial characterization of zinc binding and cleavage activity in vitro. Remarkably, several of these mutants exhibit significantly greater sensitivity to zinc than the original ΔI-CM parent intein. The most promising of these mutants, LN-004b (FIG. 10A), exhibits zinc binding almost an order of magnitude stronger than the original mini-intein (17.3 μM for LN-004b versus 100.3 μM for ΔI-CM), and surprisingly, exhibits significantly faster cleaving kinetics in the absence of zinc than the original mini-intein as well. In particular, the LN-004b intein exhibits no measurable cleaving over 24 hours at 37° C. and pH 7.0 in the presence of 100 μM zinc, while the original ΔI-CM intein requires fully 500 μM zinc to experience the same level of repression (FIG. 10B). Further, the zinc binding effect is abolished at pH lower than 6.8, allowing the zinc-binding inteins to be activated by a simple pH shift in a manner similar to the original mini-intein (without EDTA addition). Indeed, all of the constructed mutants exhibit pH sensitivity similar to the original ΔI-CM intein, with greatly enhanced controllability in the presence of zinc ion. Notably, some of the constructed mutants exhibit highly accelerated cleaving in vivo as well, and thus could not be well characterized in vitro since the uncleaved precursor could not be purified. Two of these inteins (LN-002 and LN-004b) are being expressed in CHO and cell-free expression systems in the presence of 300 μM zinc.

Experimental Plan

Stronger zinc binding can be beneficial for mammalian and other expression host applications. A two-pronged approach can be used to the optimization of the engineered intein mutants. The first approach can be to use the knowledge gained from the initial set of designs to inform a second round of rationally engineered metal binding centers. The initial six designed inteins have already been characterized and provide a clearer understanding of the strengths and weaknesses of the computational design methods. A reassuring result is that the LN-004b intein was predicted to have the strongest zinc binding, based on the angles and lengths of the predicted metal coordination bonds. These data indicate that an iterative rational approach, where each iteration is driven by experimental laboratory data, can generate highly optimized mutants. Another approach can be to target random mutagenesis of the residues surrounding the engineered binding center, coupled with the yeast display screen. In this case, beneficial random mutations can be screened, where the computational and structural models can be used to determine the specific residues targeted for mutagenesis.

Evolutionary methods can be applied to the optimization of the rationally designed inteins, as well as inteins designed for altered pH and temperature activity profiles. These approaches can include the development of an effective in vitro intein activity screening system based on yeast surface display, and a targeted mutant library, focused specifically on active site residues associated with control of the intein cleaving.

The impact of self-cleaving purification tags can be much greater if they can be used as a platform for biopharmaceutical manufacturing. To encourage their adoption, their performance can be demonstrated in the context of a cGMP process, with a focus on their incorporation into established conventional unit operations. Because CHO is the primary source of recombinant glycoproteins in the biopharmaceutical industry, it will be one of the primary targets. An important alternative is *Pichia pastoris*, which has recently been engineered to produce human glycosylation patterns on secreted protein products. The intein fusions can initially be evaluated for overall target expression and suppression of premature cleaving in these cells, with the goal of generating an optimized intein toolbox for various mammalian and eukaryotic host organisms. A critical aspect of this work is the choice of affinity tag. In particular, there are no manufacturing scale bulk sources for practically any conventional affinity resins (such as amylose, chitin or glutathione), largely due to the fact that they are never used at manufacturing scales. Further, these resins have typically not been optimized for binding capacity as conventional biopharmaceutical purification resins have, leaving them unacceptably inefficient at large scale. For this reason, alternate tags, with specific affinities for established industry standard purification resins, are studied. An important candidate tag in this area is the Choline Binding Domain of the major autolysin (C-lytA) from *Streptococcus pneumoniae*. This tag binds very tightly and specifically to the quaternary amine of choline, imparting it with strong and selective affinity for quaternary amine ion exchange resins. Most importantly, the Choline Binding Domain can bind strongly to Q-sepharose resins, even in the presence of 1.5 M NaCl. Most proteins will not bind Q-sepharose under these conditions, causing the choline binding tag to act effectively as an affinity tag for Q-sepharose, providing a very high degree of purity in a single column process (FIG. 11). Further, because Q-sepharose is a highly optimized industry standard resin, it exhibits extremely high binding capacity (up to 100 grams per liter of bed volume), and is available from many commercial sources in bulk.

Results

In previous work with eukaryotic host cells, expression of intein-tagged fusion proteins in both CHO and *Pichia* was attempted. The ELP and chitin binding tags were used in these experiments, where they were combined with cleaving and non-cleaving control inteins to determine overall expression levels and product losses due to premature tag cleaving. These experiences (described below) allow for the incorporation of new inteins into the existing characterization framework, as well as the new choline binding tag.

The data shows that in both CHO and *Pichia*, expression of intein-containing fusion proteins was possible with the original ΔI-CM intein, but unacceptable levels of premature cleaving were observed in both hosts. In CHO, an oncoM secretion leader sequence was used, followed by the ELP tag and intein genes, fused to secreted alkaline phosphatase as the target protein. A constitutive CMV promoter drove expression of the tagged fusion protein in a DG44 cell line, and in later experiments gene expression was amplified by methotrexate (MTX) addition. Gene expression could be amplified, although it typically reached only 10% to 50% of the untagged control protein. The use of a non-cleaving control intein with the ELP tag lead to the lowest observed levels, which were approximately 220 milligrams per liter of fusion protein, when expressed in shaker flask cultures at 400 nM MTX. The cleaving intein delivered approximately 800 mg/liter (by activity) under the same conditions. In *Pichia*, expression was induced by methanol addition, but no significant product was secreted with the ELP tag fused to either intein (cleaving or non-cleaving).

Chitin binding domain-tagged proteins expressed well in *Pichia*, and existing self-cleaving chitin-intein tags were used to purify both β-lactamase and β-galactosidase. In particular, the overall recovery of β-galactosidase using this method was 30% (by activity), with a 100-fold purification factor. Significant losses occurred due to excessive premature cleaving, however, leading to unacceptably low overall yields (milligrams per liter).

The choline binding tag exhibits excellent performance as a purification tag when expressed in *E. coli*, but the binding capacity of the Q-sepharose resins is typically on the order of 2 to 3 mg/ml of bed volume. This is unacceptably low, and additional process conditions to increase this capacity are being performed. The choline binding tag has been combined with several secretion leader sequences and expressed in CHO-S in transient transfection with several control inteins. The results have been mixed, indicating zinc can affect both cleaving and secretion.

It has been established that intein fusions can be expressed in two important biopharmaceutical expression hosts. The ability to express highly tractable test proteins in *Pichia* and CHO indicates that performance benchmarks will be fairly easy to establish as new inteins become available.

Experimental Plan

Existing ΔI-CM intein and future intein mutants can be adapted for cGMP manufacturing processes. Combining these inteins with the choline binding module and other conventional affinity tags that might be incorporated into a cGMP purification process with minimal validation effort can be performed. Quaternary amine ion exchange resins in particular have been optimized for extremely high binding capacities, and they can be recycled many times. Most notably, Q-resins have an established track record with the FDA, and extensive tests are available to determine their effectiveness for a given target protein. Therefore, this resin can be adapted to an intein process with minimal cGMP validation.

A broad variety of target proteins can be expressed which have been selected based on the availability of convenient activity assays and antibodies for Western blots. These proteins have included β-galactosidase, β-lactamase, secreted alkaline phosphatase, green fluorescent protein, maltose-binding protein, carbonic anhydrase, S824 protein, and others. By expressing these test target proteins in combination with a variety of tags and inteins, the impact of the tag, intein, intein cleaving rate, and expression system on overall process yields can be evaluated. Particular attention can be paid to the impact of the purification tag on protein expression and secretion, which can be evaluated through the use of various tags and untagged target proteins. The rapidly cleaving ΔI-CM intein is also available, along with noncleaving control inteins, to evaluate the effects of the mutant tag-intein fusion combination on overall expression and secretion of the target protein. These experiments in particular, can provide benchmarks on the effects of intein tags on overall protein expression, which will translate directly to the attractiveness of these expression systems and their likely process economics.

Summary

These experiments allow for the ability to directly select for controllable cleaving activity under fully flexible in vitro conditions and allowing selected mutants to be targeted to industrially important protein expression platforms. This is a significant deviation from previously published approaches, where intein reporter and selection systems have been developed for in vivo intein splicing. Additionally, a lack of selectable reporter proteins that are strongly affected by intein cleaving (as opposed to splicing) has resulted in few selection systems for intein cleaving. For these reasons, these previous methods have not been successful in generating fully controllable cleaving. By generating selection systems directly for intein cleaving in vitro, the conditions to which the intein is exposed during selection can be specified. Further, the design of these systems provides a strong and quantitative readout for intein cleaving and cleavage rate, as well as an efficient selection method for isolating desirable mutants. These aspects can allow for unprecedented control over the selection conditions, and therefore the ultimate behavior of the evolved inteins.

This work is focused on developing inteins that are directly relevant to industrially important protein expression systems and downstream processes. First and foremost among these is the CHO cell expression system, which is the main industry workhorse for producing recombinant antibodies and other therapeutic glycoproteins at multi-kilogram scales. Previous approaches have focused been primarily on controllability at laboratory scales, without consideration of eventual large-scale bioprocess development (as with IMPACT system). Although the work proposed here draws on established methods in molecular biology, it is unique in its focus on delivering a directly useful product for large-scale bioprocess engineering.

This work provides a metal binding site design strategy for controlling intein function, and the potential for this strategy to be adapted for other protein targets. In particular, the strategy indicates that an engineered metal binding motif can be used to sequester active site residues in inteins or other target proteins. By establishing a platform for reliably engineering various control mechanisms into the inteins, a means to study a range of potential control methods for additional proteins can be provided, which can also include pH and temperature variations in the presence of metal ions. This knowledge will find utility in many applications, ranging from the development of allosteric proteins for metabolic engineering, to therapeutic proteins that can be activated in situ.

The work in protein purification focused on the development of two self-cleaving tag-based nonchromatographic protein methods. One method is based on the production of polyhydroxybutyrate (PHB) granules in *E. coli* that act as affinity carriers for a co-expressed, tagged target protein. In this way, the cells provide both the affinity matrix and tagged target protein for purification. Once the granules are recovered and washed, the bound purified target protein is cleaved from their surface by the self-cleaving intein. This method has been demonstrated in *E. coli* and a highly productive *Ralstonia* strain. An initial analysis indicates a substantial economical advantage over conventional affinity separations. Another method relies on an intein fusion with an elastin-like peptide (ELP). In this case, the ELP portion of the tag is designed to reversibly precipitate upon gentle heating (about 30° C.) at salt concentrations in the 1M range. This highly specific reversible precipitation forms the basis for the separation, allowing the uncleaved precursor protein to be captured, concentrated and purified by simple cycles of heating and centrifugation or filtration (FIG. 12). Once the ELP fusion is purified, the intein is induced to cleave, releasing the native target protein from the intein-ELP tag. A final cycle of heating and centrifugation then precipitates and removes the cleaved tag, leaving the purified and native target alone in solution.

Example 5—A Self-Cleaving Purification Tag System for Use in Mammalian Cell Culture FIG. 7 is a graph of the rate constant vs. pH and temperature for the ΔI-CM mini intein. It illustrates that the cleaving rate at pH 7.5 and about 20° C., which is seen inside *E. coli* cells during expression, is sufficiently slow enough to produce an uncleaved precursor. At the conditions of CHO cell culture (pH 7.0 and 37° C.), however, the cleaving rate is much faster, which causes the tag to cleave before the protein can be recovered and purified.

FIGS. 18-20 show a structure of the ΔI-CM mini intein, and the location on the structure of the conserved His residue that is involved in cleaving. These figures show the overall structure of the intein. FIG. 19 shows the conserved His residue in ball-and-stick, to give its relative position to the cleavage site. FIG. 20 shows how zinc could bind to the conserved His residue to inhibit cleaving. Since the binding involves only one interaction with the His residue, it is weak, and thus requires a high concentration of zinc to inhibit cleaving.

FIG. 21 shows that the parent ΔI-CM intein is slightly sensitive to zinc at pH 7.0 or above, but the zinc here is added at 1 mM concentration. This concentration can significantly decrease CHO cell productivity and viability. At low pH, the zinc has no effect since the His residue is protonated at this pH and will not bind zinc at all.

FIG. 22 is a close up of ΔI-CM intein, showing the location of the His residue. FIG. 22A shows how the zinc binding motif could be added to the N-terminus of the intein (blue end), and could partially surround the conserved His residue. FIG. 22B illustrates the logic and goal of designing a zinc binding motif at the N-terminus of the intein, that will not affect the C-terminus, except that it provides a multivalent binding motif for zinc ion. If properly designed, this motif will greatly increase the affinity for zinc by the intein, allowing a much higher sensitivity to zinc and suppressing cleaving at a much lower zinc concentration. This formed the basic strategy that was later realized through computer modeling.

FIG. 23 indicates that a platform purification system can be developed using this intein to create a self-cleaving tag. This platform is very similar to the Protein A platform that is used to purify pretty much every antibody therapeutic on the market today, but no equivalent platform exists for non-antibody products.

What is claimed is:

1. A modified peptide comprising a controllable intervening protein sequence (CIPS), wherein the modified peptide comprises the structure:

$X_1$-CIPS wherein $X_1$ is an affinity tag, wherein the CIPS comprises the amino acid sequence of a reversible zinc-binding motif and an intein, wherein the reversible zinc-binding motif is appended to the N-terminus of the intein, and wherein the reversible zinc-binding motif comprises G-E-G-H (SEQ ID NO: 1) or G-D-G-H (SEQ ID NO: 2).

2. The modified peptide of claim 1, wherein the modified peptide comprises the structure $X_1$-CIPS-$X_2$ wherein $X_2$ comprises a protein of interest.

3. The modified peptide of claim 1, wherein the reversible zinc-binding motif comprises the sequence G-E-G-H-H (SEQ ID NO: 3).

4. The modified peptide of claim 1, wherein the reversible zinc-binding motif comprises the sequence G-E-G-H-G (SEQ ID NO: 4).

5. The modified peptide of claim 1, wherein the reversible zinc-binding motif comprises the sequence G-D-G-H-H (SEQ ID NO: 5).

6. The modified peptide of claim 1, wherein the reversible zinc-binding motif comprises the sequence G-D-G-H-G (SEQ ID NO: 6).

7. The modified peptide of claim 1, wherein the CIPS comprises SEQ ID NO: 11, 15, 19, 23, 27, or 31.

8. The modified peptide of claim 1, wherein the nucleic acid encoding the CIPS comprises SEQ ID NO: 12, 16, 20, 24, 28, or 32.

9. The modified peptide of claim 1, wherein the cleavage rate of the intein is reduced by 10% or more when compared to the modified peptide of claim 1 lacking the reversible zinc-binding domain.

10. A method for binding and eluting a phage-displayed polypeptide from a protein of interest, wherein said method comprises:
(a) producing the modified peptide of claim 2;
(b) binding the modified peptide of step (a) to a solid support;
(c) contacting a phage-displayed polypeptide with the support-bound modified peptide of step (b), thereby permitting binding of the phage-displayed polypeptide to the support-bound modified peptide of step (b);
(d) removing any unbound phage-displayed polypeptide; and
(e) eluting the bound phage-displayed polypeptide by inducing cleavage of the protein of interest.

11. The method of claim 10, wherein the modified peptide is exposed to a chemical agent which inhibits splicing or cleavage of the protein of interest until step (d).

12. The method of claim 11, wherein after step (d), the chemical agent which inhibits splicing or cleavage is removed, thereby allowing splicing or cleavage of the protein of interest.

13. The method of claim 11, wherein the chemical agent is zinc.

* * * * *